United States Patent [19]

Gopalan

[11] Patent Number: 5,373,008
[45] Date of Patent: Dec. 13, 1994

[54] PHENYLAMIDINE AND PHENYLGUANIDINE DERIVATIVES AND THEIR USE AS ANTI-DIABETIC AGENTS

[75] Inventor: Balasubramanian Gopalan, Bombay, India

[73] Assignee: The Boots Compant plc., England

[21] Appl. No.: 9,807

[22] Filed: Jan. 27, 1993

Related U.S. Application Data

[62] Division of Ser. No. 458,237, Dec. 28, 1989, Pat. No. 5,223,498.

[30] Foreign Application Priority Data

Feb. 16, 1989 [GB] United Kingdom ............... 8903592

[51] Int. Cl.$^5$ ............... A61K 31/535; A61K 31/54; C07D 401/10; C07D 403/10; C07D 413/10; C07D 417/10
[52] U.S. Cl. .................. 514/227.8; 514/212; 514/228.2; 514/231.8; 514/235.2; 514/235.5; 514/235.8; 514/252; 514/253; 514/316; 514/318; 514/323; 514/326; 514/343; 514/414; 514/422; 540/597; 540/598; 540/602; 544/60; 544/62; 544/86; 544/111; 544/121; 544/129; 544/141; 544/143; 544/357; 544/360; 544/372; 544/373; 546/191; 546/194; 546/200; 546/208; 546/264; 548/465; 548/523
[58] Field of Search ............... 544/129, 86, 111, 121; 544/141, 60, 357, 360, 372, 62, 143, 373; 514/235.5, 231.8, 235.8, 252, 227.8, 212, 316, 318, 326, 343, 228.2, 235.2, 253, 323, 414, 422; 540/597, 598, 602; 546/191, 194, 208, 264, 200; 548/465, 523

[56] References Cited

U.S. PATENT DOCUMENTS

| | | | |
|---|---|---|---|
| 3,867,448 | 2/1975 | Duerr et al. | 260/564 R |
| 4,281,004 | 7/1981 | Ives | 424/263 |

FOREIGN PATENT DOCUMENTS 2029299 12/1971 Germany .

*Primary Examiner*—Mukund J. Shah
*Assistant Examiner*—P. I. Datlow
*Attorney, Agent, or Firm*—Ostrolenk, Faber, Gerb & Soffen

[57] ABSTRACT

Compounds of formula I

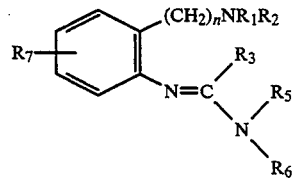

and their salts in which n=0 or 1, $R_1$ and $R_2$ are each aliphatic or cycloalkyl or $NR_1R_2$ is an optionally substituted heterocyclic ring, $R_3$ is alkyl, cycloalkyl or optionally substituted amino, $R_5$ is an aliphatic group, $R_6$ is H, an optionally substituted aliphatic group or a cycloalkyl group, or $R_3$ and $R_5$ together with the nitrogen and carbon atoms to which they are attached form an optionally substituted heterocyclic ring or $R_5$ and $R_6$ together with the nitrogen to which they are attached form a heterocyclic ring optionally substituted by alkyl and $R_7$ is optionally substituted alkyl, alkoxy, alkylthio, alkylsulphinyl, alkylsulphonyl, alkoxycarbonyl, trifluoromethyl or cyano have utility as hypoglycemic agents.

33 Claims, No Drawings

PHENYLAMIDINE AND PHENYLGUANIDINE DERIVATIVES AND THEIR USE AS ANTI-DIABETIC AGENTS

This is a division of application Ser. No. 07/458,237, filed Dec. 28, 1989 now U.S. Pat. No. 5,223,498.

This invention relates to novel therapeutic agents useful as antidiabetic agents, particularly as hypoglycemic agents, to processes for the preparation of such agents and to pharmaceutical compositions containing them.

The present invention provides compounds of formula I:

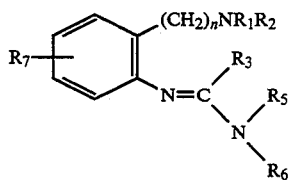

and their pharmaceutically acceptable salts in which n=0 or 1;

in which $R_1$ and $R_2$, which are the same or different, are (a) an aliphatic group containing 1 to 3 carbon atoms, said aliphatic group being optionally substituted by methoxy (b) a cycloalkyl group containing 3 to 7 carbon atoms or (c) $R_1$ and $R_2$ together with the nitrogen atom to which they are attached form an optionally substituted heterocyclic ring of formula II

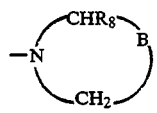

in which $R_8$ represents H or an alkyl group containing 1 to 3 carbon atoms and B represents an alkylene group of 2 to 4 carbon atoms optionally interrupted by oxygen, sulphur, sulphinyl or nitrogen optionally substituted by an alkyl group containing 1 to 3 carbon atoms, said alkylene group being optionally substituted by one or more alkyl groups containing 1 to 3 carbon atoms or the substituents on two adjacent carbon atoms of the alkylene group form a benzene ring or B represents an alkenylene group of 3 carbon atoms;

$R_3$ is a straight or branched alkyl group containing 1 to 7 carbon atoms or a cycloalkyl group containing 3 to 7 carbon atoms or a group of formula III

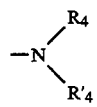

in which $R_4$ and $R'_4$, which are the same or different, are H or an alkyl group containing 1 to 4 carbon atoms;

in which $R_5$ is H or a straight or branched aliphatic group of 1 to 4 carbon atoms, said aliphatic group being optionally substituted by methoxy;

in which $R_6$ is (a) H, (b) a straight or branched aliphatic group of 1 to 6 carbon atoms optionally substituted by hydroxy or an acylated derivative thereof, by an alkoxy group containing 1 to 3 carbon atoms, by an alkylthio group containing 1 to 3 carbon atoms, by an optionally alkylated amino group, by a carbocyclic group containing 3 to 7 carbon atoms or by cyano or (c) a cycloalkyl ring containing 3 to 7 carbon atoms;

or the group $R_3$ and the group $R_5$ together with the carbon and nitrogen atoms to which they are attached form a heterocyclic ring of formula IV

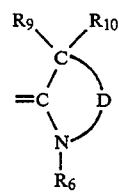

in which $R_6$ is as hereinbefore defined, $R_9$ and $R_{10}$, which are the same or different, are H or an alkyl group of 1 to 4 carbon atoms optionally substituted by methoxy and D is an oxyethylene group in which the oxygen atom is bonded to the carbon atom carrying the groups $R_9$ and $R_{10}$ or an alkylene group of 2 to 5 carbon atoms optionally substituted by one or more alkyl groups of 1 to 3 carbon atoms;

or the group $R_3$ and the group $R_5$ together with the carbon and nitrogen atoms to which they are attached form a heterocyclic ring of formula V

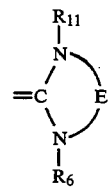

in which $R_6$ is as hereinbefore described, in which $R_{11}$ is H or an alkyl group containing 1 or 2 carbon atoms, and E is an alkylene group of 2 to 4 carbon atoms optionally substituted by one or more alkyl groups containing 1 to 3 carbon atoms;

or $R_5$ and $R_6$ together with the nitrogen atom to which they are attached form a heterocyclic ring of formula VI

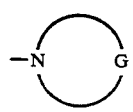

in which G is an alkylene group of 4 or 5 carbon atoms optionally interrupted by oxygen, sulphur or nitrogen optionally substituted by an alkyl group containing 1 to 3 carbon atoms, said alkylene group being optionally substituted by one or more alkyl groups containing 1 to 3 carbon atoms; and $R_7$ represents H or one or more optional substituents selected from halo, alkyl groups containing 1 to 4 carbon, atoms optionally substituted by methylthio, alkoxy groups containing 1 to 3 carbon atoms, alkylthio groups containing 1 to 3 carbon atoms, alkylsulphinyl groups containing 1 to 3 carbon atoms, alkylsulphonyl groups containing 1 to 3 carbon atoms, alkoxycarbonyl groups containing a total of 2 or 3 carbon atoms, trifluoromethyl or cyano.

In preferred compounds of formula I in which n=0, $R_1$ and $R_2$, which may be the same or different, are selected from (a) alkyl groups of 1 to 3 carbon atoms optionally substituted by methoxy (b) allyl groups or (c) cyclohexyl groups. In particularly preferred compounds of formula I in which n=0, $R_1$ and $R_2$ are both alkyl, allyl or 2-methoxyethyl or $R_1$ is methyl and $R_2$ is 2-methoxyethyl or cyclohexyl. In especially preferred compounds of formula I in which n=0, the group $NR_1R_2$ is dimethylamino, diethylamino, diallylamino, (2-methoxyethyl)methylamino, cyclohexylmethylamino or bis(2-methoxyethyl)amino.

In preferred compounds of formula I in which n=0 and in which the group $NR_1R_2$ is a heterocyclic ring represented by formula II, $R_8$ represents H or methyl and B represents a group selected from —$(CH_2)_2$—, —$CHMeCH_2$—, o-phenylene, —$(CH_2)_3$—, —$CH_2CH$-$MeCH_2$—, —$(CH_2)_4$—, —$CH_2OCH_2$—, —$CH$-$MeOCHMe$—, —$CH_2SCH_2$—, —$CH_2S(O)CH_2$—, —$CH_2NMeCH_2$— or —$CH=CHCH_2$—. In especially preferred compounds of formula I in which n=0 and the group $NR_1R_2$ is a group of formula II, the group $NR_1R_2$ is 1-pyrrolidinyl, 2-methyl-1-pyrrolidinyl, piperidino, 4-methylpiperidino, 1-hexahydroazepinyl, morpholino, 2,6-dimethylmorpholino, thiamorpholino, thiamorpholino 1oxide, 2-isoindolinyl, 4-methyl-1-piperazinyl or 1-(1,2,5,6-tetrahydro)pyridyl. In preferred compounds of formula I in which n=1, the group $NR_1R_2$ is morpholino or thiamorpholino.

In preferred compounds of formula I in which $R_3$ is an alkyl group, the group $R_3$ contains 1 to 5 carbon atoms (e.g. methyl, ethyl, propyl, isopropyl, butyl, t-butyl or pentyl). In preferred compounds of formula I in which the group $R_3$ is a cycloalkyl group, the cycloalkyl group is cyclohexyl.

In preferred compounds of formula I in which $R_3$ is a group of formula III, $R_4$ and $R_4'$ are H, methyl or ethyl (for example $R_3$ is amino, methylamino, dimethylamino or ethylamino).

In preferred compounds of formula I in which the group $R_5$ does not form part of a heterocyclic ring, the group $R_5$ is H or an alkyl group containing 1 to 3 carbon atoms (e.g. methyl or ethyl) optionally substituted by methoxy (e.g. $R_5$ is methoxyethyl) or allyl.

In preferred compounds of formula I, $R_6$ is H or a straight or branched alkyl group containing 1 to 5 carbon atoms (e.g. methyl, ethyl, propyl, isopropyl, butyl, isobutyl, sec-butyl, tert-butyl or pentyl) optionally substituted by hydroxy (e.g. $R_6$ is 2-hydroxyethyl, 3-hydroxypropyl, 2-hydroxypropyl, 2-hydroxybutyl, 2-hydroxy-2-methylpropyl, or 2,3-dihydroxypropyl), by an acylated derivative of hydroxy such as acetyloxy or benzoyloxy (e.g. $R_6$ is 2-acetyloxyethyl or 2-benzoyloxyethyl) by methoxy (e.g. $R_6$ is 2-methoxyethyl), by methylthio (e.g. $R_6$ is 2-methylthioethyl), by dimethylamino (e.g. $R_6$ is 2dimethylaminoethyl), by phenyl (e.g. $R_6$ is benzyl or 2-phenylethyl) or by cyano (e.g. $R_6$ is 2-cyanoethyl) or $R_6$ is a straight or branched alkylene group containing 3 to 6 carbon atoms (e.g. $R_6$ is allyl or 2-methylallyl).

In preferred compounds of formula I in which $R_6$ is a cycloalkyl group, $R_6$ contains 5 or 6 carbon atoms (e.g. $R_6$ is cyclopentyl or cyclohexyl).

In particularly preferred compounds of formula I in which the groups $R_3$ and $R_5$ together with the nitrogen and carbon atoms to which they are attached do not form a heterocyclic ring, the group —$N=C(R_3)NR_5R_6$ is:

acetamidino,
N-methylacetamidino,
N,N-dimethylacetamidino,
N,N-diethylacetamidino,
N-(2-acetyloxyethyl)acetamidino,
N-butylacetamidino,
N-pentylacetamidino,
N-methylpropionamidino,
N,N-dimethylpropionamidino
N-ethylpropionamidino,
butyramidino,
N-methylbutyramidino,
N,N-dimethylbutyramidino,
N-ethylbutyramidino,
isobutyramidino,
N-methylisobutyramidino,
N,N-dimethylisobutyramidino,
valeramidino,
N-methylvaleramidino,
N,N-dimethylvaleramidino,
pivalamidino,
N-methylpivalamidino,
N,N-dimethylpivalamidino,
N-methylcaproamidino
N-methylcyclohexanecarboxamidino,
diaminomethyleneamino,
N-methylguanidino,
N,N-dimethylguanidino,
N,N'-dimethylguanidino,
N-ethylguanidino,
N-butylguanidino,
N-ethyl-N-methylguanidino,
N,N-diethylguanidino,
N,N'-diethylguanidino,
N,N',N'-trimethylguanidino,
1,1,3,3-tetramethylguanidino,
N-ethyl-N'-methylguanidino,
1-ethyl-1,3,3-trimethylguanidino,
1-butyl-1,3,3-trimethylguanidino,
N-methyl-N-propylguanidino,
N-butyl-N-methylguanidino,
N-sec-butyl-N'-methylguanidino,
N-tert-butyl-N'-methylguanidino,
N-isobutyl-N'-methylguanidino,
N-butyl-N'-methylguanidino,
N-butyl-N'-ethylguanidino,
N-methyl-N'-pentylguanidino,
N-cyclopentyl-N'-methylguanidino,
N-(2-methoxyethyl)guanidino
N-(2-methoxyethyl)-N-methylguanidino,
N-(2-methoxyethyl)-N'-methylguanidino,
N-ethyl-N-(2-methoxyethyl)guanidino,
N,N-bis(2-methoxyethyl)guanidino,
N-methyl-N-(2-methylthioethyl)guanidino,
N-allyl-N-methylguanidino,
N-allyl-N'-methylguanidino,
1-allyl-1,3,3-trimethylguanidino,
N,N-diallylguanidino, In one group of preferred compounds of formula I in which the groups $R_3$ and $R_5$ together with the carbon and nitrogen atoms to which they are attached form a heterocyclic ring of formula IV, $R_9$ and $R_{10}$, which may be the same or different, are H or alkyl groups containing 1 to 3 carbon atoms (for example methyl, ethyl or isopropyl) optionally substituted by methoxy (eg $R_9$ and/or R$_{10}$ are methoxyethyl), D is selected from —(CH$_2$)$_2$—, —(CH$_2$)$_3$—, —(CH$_2$)$_4$—, —(CH$_2$)$_5$—, —CH$_2$CMe$_2$— or —O(CH$_2$)$_2$— and the group R$_6$ is preferably H, methyl, ethyl, isopropyl, cyclohexyl, 2-cyanoethyl, 2-acetoxyethyl or 2-methoxyethyl. In particularly preferred compounds of formula I, formula IV represents:

2-pyrrolidinylidene,
1-methyl-2-pyrrolidinylidene,
3-methyl-2-pyrrolidinylidene,
1-ethyl-2-pyrrolidinylidene,
1-isopropyl-2-pyrrolidinylidene,
1-cyclohexyl-2-pyrrolidinylidene,
1-(2-methoxyethyl)-2-pyrrolidinylidene,
1,3-dimethyl-2-pyrrolidinylidene,
5,5-dimethyl-2-pyrrolidinylidene,
1,3,3-trimethyl-2-pyrrolidinylidene,
1,5,5-trimethyl-2-pyrrolidinylidene,
3-isopropyl-1-methyl-2-pyrrolidinylidene,
1-ethyl-3,3-dimethyl-2-pyrrolidinylidene,
3,3-diethyl-1-methyl-2-pyrrolidinylidene,
2-piperidinylidene,
1-methyl-2-piperidinylidene,
1,3-dimethylpiperidinylidene,
1-ethyl-2-piperidinylidene,
1-isopropyl-2-piperidinylidene,
1-(2-cyanoethyl)-2-piperidinylidene,
1-(2-acetoxyethyl)-2-piperidinylidene,
3-(2-methoxyethyl)-1-methyl-2-piperidinylidene,
2-hexahydroazepinylidene,
1-methyl-2-hexahydroazepinylidene,
2-octahydroazocinylidene or
3-morpholinylidene.

In a second group of preferred compounds of formula I in which the groups R$_3$ and R$_5$ together with the carbon and nitrogen atoms to which they are attached form a heterocyclic ring of formula V, E is —CH$_2$CH$_2$—, —CMe$_2$CH$_2$—, —CHMeCHMe—, —(CH$_2$)$_3$—, CHMeCH$_2$— or —(CH$_2$)$_4$—, R$_{11}$ is H, methyl or ethyl and R$_6$ is H, methyl, ethyl, propyl, isopropyl, butyl, isobutyl, pentyl, allyl, 2-methylallyl, 2-hydroxyethyl, 2-acetoxyethyl, 2-benzoyloxyethyl, 2-methoxyethyl, cyclohexyl, benzyl, phenethyl, 3-hydroxypropyl, 2-hydroxypropyl, 2-hydroxy-2-methylpropyl, 2-hydroxybutyl, 2,3-dihydroxypropyl or 2-dimethylaminoethyl. In particularly preferred compounds of formula I, formula V represents:

2-imidazolidinylidene,
1-methyl-2-imidazolidinylidene,
4-methyl-2-imidazolidinylidene,
4,4-dimethyl-2-imidazolidinylidene,
4,5-dimethyl-2-imidazolidinylidene,
1-ethyl-2-imidazolidinylidene,
1-propyl-2-imidazolidinylidene,
1-isopropyl-2-imidazolidinylidene,
1-(n-butyl)-2-imidazolidinylidene,
1-isobutyl-2-imidazolidinylidene,
1-pentyl-2-imidazolidinylidene,
1-allyl-2-imidazolidinylidene,
1-(2-methylallyl)-2-imidazolidinylidene,
1-(2-hydroxyethyl)-2-imidazolidinylidene,
1-(2-hydroxyethyl)-3-methyl-2-imidazolidinylidene,
1-(2-acetoxyethyl)-2-imidazolidinylidene,
1-(2-benzoyloxyethyl)-2-imidazolidinylidene,
1-(2-benzoyloxyethyl)-3-methyl-2-imidazolidinylidene,
4,5-dimethyl-1-(2-hydroxyethyl)-2-imidazolidinylidene,
1-(2-methoxyethyl)-2-imidazolidinylidene,
1-(2-methoxyethyl)-3-methyl-2-imidazolidinylidene,
1-cyclohexyl-2-imidazolidinylidene,
1-benzyl-2-imidazolidinylidene,
1-(2-phenylethyl)-2-imidazolidinylidene,
1-(2-dimethylaminoethyl)-2-imidazolidinylidene,
1-(3-hydroxypropyl)-2-imidazolidinylidene,
1-(2-hydroxypropyl)-2-imidazolidinylidene,
1-(2-hydroxy-2-methylpropyl)-2-imidazolidinylidene,
1-(2-hydroxybutyl)-2-imidazolidinylidene,
1-(2,3-dihydroxypropyl)-2-imidazolidinylidene,
1,3-dimethyl-2-imidazolidinylidene,
1,3-diethyl-2-imidazolidinylidene,
1-ethyl-3-methyl-2-imidazolidinylidene,
1-butyl-3-methyl-2-imidazolidinylidene,
1-isopropyl-4,4-dimethyl-2-imidazolidinylidene,
1-methyl-2-perhydropyrimidinylidene or
1,3-diazacycloheptane.

In preferred compounds of formula I in which R$_5$ and R$_6$ together with the nitrogen atom to which they are attached form a heterocyclic ring of formula VI, G represents a group selected from —(CH$_2$)$_4$—, —(CH$_2$)$_5$—, —(CH$_2$)$_2$O(CH$_2$)$_2$—, —(CH$_2$)$_2$S(CH$_2$)$_2$—, —(CH$_2$)$_2$NMe(CH$_2$)$_2$—, —(CH$_2$)$_2$CHMe(CH$_2$)$_2$— or —CH$_2$CHMeOCHMeCH$_2$—. In particularly preferred compounds, the group NR$_5$R$_6$ is 1-pyrrolidinyl, piperidino, 4-methylpiperidino, morpholino, 2,6-dimethylmorpholino, thiamorpholino or 4-methyl-1-piperazinyl. In particularly preferred compounds of formula I in which R$_5$ and R$_6$ together with the nitrogen atom to which they are attached form a heterocyclic ring of formula VI, the group —N=C(R$_3$)NR$_5$R$_6$ is:

N,N-(3-oxapentamethylene)guanidino,
1,1-dimethyl-3,3-(3-oxapentamethylene)guanidino,
N,N-(2,4-dimethyl-3-oxapentamethylene)guanidino,
N,N-(3-thiapentamethylene)guanidino,
N,N-(3-methylpentamethylene)guanidino,
N,N-(N-methyl-3-azapentamethylene)guanidino,
N-methyl-N',N'-tetramethyleneguanidine,
N,N-pentamethyleneguanidino,
1,1-dimethyl-3,3-pentamethyleneguanidino.

In preferred compounds of formula I, R$_7$ represents H or one or more substituents (preferably one or two substituents) selected from fluoro, chloro, methyl, ethyl, isobutyl, methylthiomethyl, methoxy, dimethoxy, methoxycarbonyl, methylthio, methylsulphinyl, methylsulphonyl, trifluoromethyl or cyano.

Specific compounds of formula I are
4-[2-(2-piperidinylideneamino)phenyl]morpholine
4-[2-(1-methyl-2-piperidinylideneamino)phenyl]morpholine
4-[2-(1-ethyl-2-piperidinylideneamino)phenyl]morpholine
4-[2-(1-isopropyl-2-piperidinylideneamino)phenyl]morpholine
4-[2-(2-hexahydroazepinylideneamino)phenyl]morpholine
4-[2-(1-methyl-2-hexahydroazepinylideneamino)phenyl]morpholine
4-[2-(2-octahydroazocinylideneamino)phenyl]morpholine
4-[2-(2-pyrrolidinylideneamino)phenyl]morpholine
4-[2-(1-methyl-2-pyrrolidinylideneamino)phenyl]morpholine
4-[2-(1,3-dimethyl-2-pyrrolidinylideneamino)phenyl]morpholine
4-[2-(1,3,3-trimethyl-2-pyrrolidinylideneamino)phenyl]morpholine 4-[2-(1-ethyl-2-pyrrolidinylideneamino)phenyl]morpholine
4-(2-[1-(2-methoxyethyl)-2-pyrrolidinylideneamino]phenyl)morpholine
4-[2-(1-cyclohexyl-2-pyrrolidinylideneamino)phenyl]morpholine
4-[2-(3,3-dimethyl-1-ethyl-2-pyrrolidinylideneamino)phenyl]morpholine
4-[2-(3,3-diethyl-1-methyl-2-pyrrolidinylideneamino)phenyl]morpholine
4-[2-(3-isopropyl-1-methyl-2-pyrrolidinylideneamino)phenyl]morpholine
4-[2-(1,3-dimethyl-2-piperidinylideneamino)phenyl]morpholine
4-[3-methyl-2-(2-piperidinylideneamino)phenyl]morpholine
4-[3-methyl-2-(1-methyl-2-piperidinylideneamino)phenyl]morpholine
4-[4-methyl-2-(2-piperidinylideneamino)phenyl]morpholine
4-[4-methyl-2-(1-methyl-2-piperidinylideneamino)phenyl]morpholine
4-[5-methyl-2-(2-piperidinylideneamino)phenyl]morpholine
4-[6-methyl-2-(2-piperidinylideneamino)phenyl]morpholine
4-[4-ethyl-2-(2-piperidinylideneamino)phenyl]morpholine
4-[3-chloro-2-(2-piperidinylideneamino)phenyl]morpholine
4-[4-chloro-2-(2-piperidinylideneamino)phenyl]morpholine
4-[4-chloro-2-(1-methyl-2-piperidinylideneamino)phenyl]morpholine
4-[5-chloro-2-(2-piperidinylideneamino)phenyl]morpholine
4-[6-chloro-2-(2-piperidinylideneamino)phenyl]morpholine
4-[4-fluoro-2-(2-piperidinylideneamino)phenyl]morpholine
4-[4-fluoro-2-(1-methyl-2-piperidinylideneamino)phenyl]morpholine
4-[4-methoxy-2-(2-piperidinylideneamino)phenyl]morpholine
4-[4-methoxycarbonyl-2-(2-piperidinylideneamino)phenyl]morpholine
4-[4-methylsulphonyl-2-(2-piperidinylideneamino)phenyl]morpholine
4-(2-[1-(2-acetoxyethyl)-2-piperidinylideneamino]phenyl)morpholine
4-(2-[1-methyl-3-(2-methoxyethyl)-2-piperidinylideneamino]phenyl)morpholine
4-[2-(3-methyl-2-pyrrolidinylideneamino)phenyl]morpholine
N-methyl-N'-(2-morpholinophenyl)acetamidine
N-(2-morpholinophenyl)-N'-propylacetamidine
N-(n-butyl)-N'-(2-morpholinophenyl)acetamidine
N-(n-pentyl)-N'-(2-morpholinophenyl)acetamidine
N-(2-acetoxyethyl)-N'-(2-morpholinophenyl)acetamidine
N,N-dimethyl-N'-(2-morpholinophenyl)acetamidine
N,N-diethyl-N'-(2-morpholinophenyl)acetamidine
N-methyl-N'-(2-morpholinophenyl)propionamidine
N-ethyl-N'-(2-morpholinophenyl)propionamidine
N,N-dimethyl-N'-(2-morpholinophenyl)propionamidine
N-methyl-N'-(2-morpholinophenyl)butyramidine
N-ethyl-N'-(2-morpholinophenyl)butyramidine
N,N-dimethyl-N'-(2-morpholinophenyl)butyramidine
N-methyl-N'-(2-morpholinophenyl)-2-methylpropionamidine
N,N-dimethyl-N'-(2-morpholinophenyl)-2-methylpropionamidine
N-methyl-N'-(2-morpholinophenyl)valeramidine
N,N-dimethyl-N'-(2-morpholinophenyl)valeramidine
N-methyl-N'-(2-morpholinophenyl)pivalamidine
N,N-dimethyl-N'-(2-morpholinophenyl)pivalamidine
N-methyl-N'-(2-morpholinophenyl)hexanamidine
N-methyl-N'-[2-(1-pyrrolidinyl)phenyl]butyramidine
N-methyl-N'-[2-(1-pyrrolidinyl)phenyl]pivalamidine
N-methyl-N'-(2-morpholinophenyl)cyclohexane carboxamidine
N-methyl-N'-(2-piperidinophenyl)pivalamidine
1-[2-(2-piperidinylideneamino)phenyl]pyrrolidine
1-[2-(1-methyl-2-piperidinylideneamino)phenyl]pyrrolidine
1-[2-(1-ethyl-2-piperidinylideneamino)phenyl]pyrrolidine
1-[4-chloro-2-(1-methyl-2-piperidinylideneamino)phenyl]pyrrolidine
1-[3-methyl-2-(1-methyl-2-piperidinylideneamino)phenyl]pyrrolidine
1-[2-(1-methyl-2-pyrrolidinylideneamino)phenyl]pyrrolidine
1-[2-(1,3-dimethyl-2-pyrrolidinylideneamino)phenyl]pyrrolidine
1-[2-(1-methyl-2-hexahydroazepinylideneamino)phenyl]pyrrolidine
1-[4-methyl-2-(2-piperidinylideneamino)phenyl]pyrrolidine
1-[4-chloro-2-(2-piperidinylideneamino)phenyl]pyrrolidine
1-[3-methyl-2-(2-piperidinylideneamino)phenyl]pyrrolidine
1-[6-methyl-2-(2-piperidinylideneamino)phenyl]pyrrolidine
4-[2-(2-piperidinylideneamino)phenyl]thiamorpholine
1-[2-(2-piperidinylideneamino)phenyl]piperidine
1-[2-(1-methyl-2-piperidinylideneamino)phenyl]piperidine
1-[2-(2-piperidinylideneamino)phenyl]hexahydroazepine
2,6-dimethyl-4-[2-(2-piperidinylideneamono)phenyl]morpholine
4-methyl-1-[2-(2-piperidinylideneamino)phenyl]piperidine
1-[2-(2-piperidinylideneamino)phenyl]-1,2,5,6-tetrahydropyridine
2-methyl-1-[2-(2-piperidinylideneamino)phenyl]pyrrolidine
2-[2-(2-piperidinylideneamino)phenyl]isoindoline
4-[2-(1-methyl-2-piperidinylideneamino)phenyl]thiamorpholine
4-[4-methyl-2-(2-piperidinylideneamino)phenyl]thiamorpholine
N-(2methoxyethyl)-N-[2-(2-piperidinylideneamino)phenyl]methylamine
N-[2-(2-piperidinylideneamino)phenyl]dimethylamine
N-[2-(2-piperidinylideneamino)phenyl]diallylamine
N-cyclohexyl-N-[2-(2-piperidinylideneamino)phenyl]methylamine
N-[2-(2-piperidinylidineaminophenyl)-bis-(2-methoxyethyl)amine 4-[2-(1,3,3-trimethyl-2-pyrrolidinylidineamino)-
phenyl]thiamorpholine
1-[2-(1,3,3-trimethyl-2-pyrrolidinylidineamino)-
phenyl]piperidine
1-[2-(1,3,3-trimethyl-2-pyrrolidinylidineamino)-
phenyl]4-methylpiperazine
1-[2-(1,3,3-trimethyl-2-pyrrolidinylidineamino)-
phenyl]pyrrolidine
4-[4-methyl-2-(1,3,3-trimethyl-2-pyr-
rolidinylideneamino)phenyl]morpholine
1-[2-(1-methyl-2-pyrrolidinylideneamino)phenyl]-
piperidine
1-[2-(1,3-dimethyl-2-pyrrolidinylideneamino)-
phenyl]piperidine
4-[2-(5,5-dimethyl-2-pyrrolidinylideneamino)-
phenyl]morpholine
4-[1,5,5-trimethyl-2-pyrrolidinylideneamino)phenyl]-
morpholine
N-[2-(1,3,3-trimethyl-2-pyrrolidinylideneamino)-
phenyl]bis-(2-methoxyethyl)amine
N-(2-morpholinophenyl)acetamidine
N-(5-methyl-2-morpholinophenyl)acetamidine
N-(2-morpholinophenyl)propionamidine
N-(2-morpholinophenyl)butyramidine
N-(2-morpholinophenyl)isobutyramidine
N-(5-methylthio-2-morpholinophenyl)isobutyrami-
dine
N-(5-fluoro-2-morpholinophenyl)isobutyramidine
N-(2-morpholinophenyl)valeramidine
N-(2-morpholinophenyl)pivalamidine
4-(2-[1-(cyanoethyl)-2-piperidinylideneamino]-
phenyl)morpholine
4-[2-(3-morpholinylideneamino)phenyl]morpholine
4-[2-(2-piperidinylideneamino)benzyl]morpholine
4-[2-(1-methyl-2-pyrrolidinylideneamino)benzyl]-
morpholine
4-[4-chloro-2-(2-piperidinylideneamino)benzyl]mor-
pholine
4-[2-(1,3,3-trimethyl-2-pyrrolidinylideneamino)ben-
zyl]morpholine
N-methyl-N'-(2-morpholinomethylphenyl)pivalami-
dine
4-[2-(1,3-dimethyl-2-imidazolidinylideneamino)-
phenyl]morpholine
4-[2-(1,3-dimethyl-2-imidazolidinylideneamino)-4-
fluorophenyl]morpholine
4-[2-(1,3-dimethyl-2-imidazolidinylideneamino)-3-
methylphenyl]morpholine
4-[2-(1,3-dimethyl-2-imidazolidinylideneamino)-4-
methylphenyl]morpholine
4-[2-(1,3-dimethyl-2-imidazolidinylideneamino)-5-
methylphenyl]morpholine
4-[4-chloro-2-(1,3-dimethyl-2-
imidazolidinylideneamino)phenyl]morpholine
4-[2-(1,3-dimethyl-2-imidazolidinylideneamino)-4-
methoxyphenyl]morpholine
4-[4,5-dimethoxy-2-(1,3-dimethyl-2-
imidazolidinylideneamino)phenyl]morpholine
1-[2-(1,3-dimethyl-2-imidazolidinylideneamino)-
phenyl]pyrrolidine
1-[2-(1,3-dimethyl-2-imidazolidinylideneamino)-3-
methylphenyl]pyrrolidine
1-[2-(1,3-dimethyl-2-imidazolidinylideneamino)-
phenyl]piperidine
4-[2-(1,3-dimethyl-2-imidazolidinylideneamino)-
phenyl]thiamorpholine
2,6-dimethyl-4-[2-(1,3-dimethyl-2-
imidazolidinylideneamino)phenyl]morpholine
N-[2-(1,3-dimethyl-2-imidazolidinylideneamino)-
phenyl]diethylamine
1-[2-(1,3-dimethyl-2-imidazolidinylideneamino)-
phenyl]-2-methylpyrrolidine
4-[3-chloro-2-(1,3-dimethyl-2-
imidazolidinylideneamino)phenyl]morpholine
1-[2-(1,3-dimethyl-2-imidazolidinylideneamino)-4-
methylphenyl]pyrrolidine
N-[2-(1,3-dimethyl-2-imidazolidinylideneamino)-
phenyl]-bis-(2-methoxyethyl)amine
4-[2-(1,3-diethyl-2-imidazolidinylideneamino)-
phenyl]morpholine
4-[2-(1,3-dimethyl-2-imidazolidinylideneamino)-6-
methylphenyl]pyrrolidine
4-[2-(1-ethyl-3-methyl-2-imidazolidinylideneamino)-
phenyl]morpholine
4-[2-(1-n-butyl-3-methyl-2-
imidazolidinylideneamino)phenyl]morpholine
4-{2-[1-(2-benzoyloxyethyl)-3-methyl-2-
imidazolinylideneamino]phenyl}morpholine
2-(2-morpholinophenyl)-1,1,3,3-tetramethylguani-
dine
1-ethyl-2-(2-morpholinophenyl)-1,3,3-trimethyl-
guanidine
1-allyl-2-(2-morpholinophenyl)-1,3,3-trimethylguani-
dine
1-n-butyl-2-(2-morpholinophenyl)-1,3,3-trimethyl-
guanidine
1-pentyl-2-(2-morpholinophenyl)-1,3,3-trimethyl-
guanidine
4-{2-[1-methyl-3-(2-methoxyethyl)-2-
imidazolidinylideneamino]phenyl}morpholine
4-{2-[1-methyl-3-(2-hydroxyethyl)-2-
imidazolidinylideneamino]phenyl}morpholine
N,N-dimethyl-N'-(2-morpholinophenyl)morpholine-
4-carboxamidine
N,N-dimethyl-N'-(2-morpholinophenyl)piperidine-1-
carboxamidine
4-[2-(1,3-dimethyl-2-imidazolidinylideneamino)-
phenyl]thiamorpholine-1-oxide
4-[2-(2-imidazolidinylideneamino)phenyl]morpholine
4-[2-(1-methyl-2-imidazolidinylideneamino)phenyl]-
morpholine
4-[2-(1-ethyl-2-imidazolidinylideneamino)phenyl]-
morpholine
4-[2-(1-n-propyl-2-imidazolidinylideneamino)-
phenyl]morpholine
4-[2-(1-isopropyl-2-imidazolidinylideneamino)-
phenyl]morpholine
4-[2-(1-n-butyl-2-imidazolidinylideneamino)phenyl]-
morpholine
4-[2-(1-isobutyl-2-imidazolidinylamino)phenyl]mor-
pholine
4-[2-(1-pentyl-2-imidazolidinylamino)phenyl]mor-
pholine
4-[2-(1-allyl-2-imidazolidinylideneamino)phenyl]
4-{2-[1-(2-hydroxyethyl)-2-
imidazolidinylideneamino]phenyl}morpholine
4-{2-[1-(2-hydroxyethyl)-2-
imidazolidinylideneamino]-3-methylphenyl}mor-
pholine
4-{2-[1-(2-methoxyethyl)-2-
imidazolidinylideneamino]phenyl}morpholine
4-[2-(1-cyclohexyl-2-imidazolidinylideneamino)-
phenyl]morpholine
4-[2-(1-benzyl-2-imidazolidinylideneamino)phenyl]-
morpholine 4-{2-[1-(2-phenylethyl)-2-imidazolidinylideneamino]phenyl}morpholine
4-{2-[1-(2-dimethylaminoethyl)-2-imidazolidinylideneamino]phenyl}morpholine
4-{2-[1-(2,3-dihydroxypropyl)-2-imidazolidinylideneamino]phenyl}morpholine
4-{2-[1-(2-methylallyl)-2-imidazolidinylideneamino]phenyl}morpholine
N-[2-(1-methyl-2-imidazolidinylideneamino)phenyl]-bis(2-methoxyethyl)amine
N-{2-[1-(2-hydroxyethyl)-2-imidazolidinylideneamino]phenyl}bis-(2-methoxyethyl)amine
4-[2-(1-methyl-2-imidazolidinylideneamino)phenyl]thiamorpholine
1-[2-(1-methyl-2-imidazolidinylideneamino)phenyl]pyrrolidine
4-[2-(1-n-butyl-2-imidazolidinylideneamino)phenyl]thiamorpholine
4-[2-(1-methyl-2-imidazolidinylideneamino)-3-methylphenyl]morpholine
4-[2-(1-methyl-2-imidazolidinylideneamino)-4-methylphenyl]morpholine
1-{2-[1-(2-hydroxyethyl)-2-imidazolindinylideneamino]phenyl}pyrrolidine
1-{2-[1-(2-hydroxyethyl)-2-imidazolindinylideneamino]phenyl}-2-methylpyrrolidine
4-[4-methyl-2-(1-n-butyl-2-imidazolidinylidene)phenyl]morpholine
1-[2-(2-imidazolidinylideneamino)phenyl]piperidine
1-[2-(1-methyl-2-imidazolidinylideneamino)phenyl]
1-[2-(1-methyl-2-imidazolidinylideneamino)-3-methylphenyl]piperidine
4-{2-[1-(2-hydroxyethyl)-2-imidazolidinylideneamino]phenyl}thiamorpholine
1-{2-[1-(2-hydroxyethyl)-2-imidazolidinylideneamino]phenyl}piperidine
4-{2-[1-(3-hydroxypropyl)-2-imidazolidinylideneamino]phenyl}morpholine
4-{2-[1-(2-hydroxypropyl)-2-imidazolidinylideneamino]phenyl}morpholine
4-{2-[1-(2-hydroxybutyl)-2-imidazolidinylideneamino]phenyl}morpholine
4-{2-[1-(2-hydroxy-2-methylpropyl)-2-imidazolidinylideneamino]phenyl}morpholine
4-[2-(4-methyl-2-imidazolidinylideneamino)phenyl]morpholine
4-[2-(4,5-dimethyl-2-imidazolidinylideneamino)phenyl]morpholine
4-{2-[4,5-dimethyl-1-(2-hydroxyethyl)-2-imidazolidinylideneamino]phenyl}morpholine
4-[2-(1-isopropyl-4,4-dimethyl-2-imidazolidinylideneamino)phenyl]morpholine
4-[2-(1-methylperhydropyrimidin-2-ylideneamino)phenyl]morpholine
2-(2-morpholinophenylimino)-1,3-diazacycloheptane
1,1-dimethyl-2-(2-morpholinophenyl)guanidine
1,3-dimethyl-2-(2-morpholinophenyl)guanidine
1,3,3-trimethyl-2-(2-morpholinophenyl)guanidine
1-ethyl-2-(2-morpholinophenyl)-3-methylguanidine
1,3-diethyl-2-(2-morpholinophenyl)guanidine
4-{2-[1-(2-acetyloxyethyl)-2-imidazolidinylideneamino]phenyl}morpholine
4-{2-[1-(2-benzoyloxyethyl)-2-imidazolidinylideneamino]phenyl}morpholine
1-(n-butyl)-2-(2-morpholinophenyl)-3-methylguanidine
1-(2-methoxyethyl)-2-(2-piperidinophenyl)guanidine
1-(2-methylthioethyl)-2-(2-morpholinophenyl)guanidine
1-(2-methoxyethyl)-2--morpholinephenyl)guanidine
1-(n-propyl)-2-(2-morpholinophenyl)-3-methylguanidine
1-(2-methoxyethyl)-3-methyl-2-(2-morpholinophenyl)guanidine
1-cyclopentyl-2-(2-morpholinophenyl)-3-methylguanidine
N-methyl-N'-(2-morpholinophenyl)pyrrolidine-1-carboxamidine
1-(n-butyl)-2-(2-morpholinophenyl)-3-ethylguanidine
1,3-dimethyl-2-(5-chloro-2-morpholinophenyl)guanidine
1-allyl-2-[2-(1-pyrrolidinyl)phenyl]-3-methylguanidine
1,3-dimethyl-2-(5-methyl-2-morpholinophenyl)guanidine
4-{2-[1-(2-hydroxyethyl)-2-imidazolidinylideneamino]-4-methylphenyl}morpholine
1-methyl-2-(2-morpholinophenyl)-3-(n-pentyl)guanidine
1-(n-butyl)-2-(5-methyl-2-morpholinophenyl)-3-methylguanidine
1-(n-butyl)-2-(6-methyl-2-morpholinophenyl)-3-methylguanidine
1-(n-butyl)-2-(5-fluoro-2-morpholinophenyl)3-methylguanidine
1-(n-butyl)-2-(5-methylthio-2-morpholinophenyl)-3-methylguanidine
1-isobutyl-2-(2-morpholinophenyl)-3-methylguanidine
1-sec-butyl-2-(2-morpholinophenyl)-3-methylguanidine
1-tert-butyl-2-(2-morpholinophenyl)-3-methylguanidine
1-allyl-2-(2-morpholinophenyl)-3-methylguanidine
1-(n-butyl)-2-(2-thiamorpholinophenyl)-3-methylguanidine
1,1-dimethyl-2-(2-morpholino-5-trifluoromethylphenyl)guanidine
1,1-dimethyl-2-(5-cyano-2-morpholinophenyl)guanidine
1,3-di-(n-propyl)-2-(2-morpholinophenyl)gaunidine
2-(2-morpholinophenyl)guanidine
1,1-dimethyl-2-(5-methyl-2-morpholinophenyl)guanidine
1,1-dimethyl-2-(6-methyl-2morpholinophenyl)guanidine
1,1-dimethyl-2-(4-chloro-2-morpholinophenyl)guanidine
1,1-dimethyl-2-(3-chloro-2-morpholinophenyl)guanidine
1,1-dimethyl-2-(5-methoxy-2-morpholinophenyl)guanidine
1,1-dimethyl-2-(5-methylthio-2-morpholinophenyl)guanidine
1,1-dimethyl-2-(4-methyl-2-morpholinophenyl)guanidine
1,1-dimethyl-2-(5-ethyl-2-morpholinophenyl)guanidine
1,1-dimethyl-2-(5-methylthiomethyl-2-morpholinophenyl)guanidine
1,1-diethyl-2-(2-morpholinophenyl)guanidine
1-(n-butyl)-1-methyl-2-(2-morpholinophenyl)guanidine 1,1-bis(2-methoxyethyl)-2-(2-morpholinophenyl)-
  guanidine
N-(2-morpholinophenyl)morpholine-4-carboxami-
  dine
N-(2-morpholinophenyl)pyrrolidine-1-carboxami-
  dine
1,1-dimethyl-2-(2-piperidinophenyl)guanidine
1,1-dimethyl-2-[2-(1-pyrrolidinyl)phenyl]guanidine
1,1-dimethyl-2-(2-thiamorpholinophenyl)guanidine
1,1-dimethyl-2-(2-dimethylaminophenyl)guanidine
1,1-dimethyl-2-{2-[N-(2-methoxyethyl)-N-
  methylamino]phenyl}guanidine
1,1-dimethyl-2-[2-(4-methyl-1-piperazinyl)phenyl]-
  guanidine
N-(2-piperidinophenyl)morpholine-4-carboxamidine
N-(2-piperidinophenyl)piperidine-1-carboxamidine
1,1-dimethyl-2-(5-methoxycarbonyl-2-morpholino-
  phenyl)guanidine
1-methyl-2-(2-morpholinophenyl)guanidine
1-ethyl-2-(2-morpholinophenyl)guanidine
1-butyl-2-(2-morpholinophenyl)guanidine
1-ethyl-1-methyl-2-(2-morpholinophenyl)guanidine
1-methyl-1-(2-methylthioethyl)-2-(2-morpholino-
  phenyl)guanidine
1-(2-methoxyethyl)-1-methyl-2-(2-morpholino-
  phenyl)guanidine
1-allyl-1-methyl-2-(2-morpholinophenyl)guanidine
1-ethyl-1-(2-methoxyethyl)-2-(2-morpholinophenyl)-
  guanidine
1,1-diallyl-2-(2-morpholinophenyl)guanidine
N-(2-morpholinophenyl)-4-methylpiperazine-1-car-
  boxamidine
N-(2-morpholinophenyl)-2,6-dimethylmorpholine-4-
  carboxamidine
N-(2-morpholinophenyl)thiamorpholine-4-carbox-
  amidine
N-(2-morpholinophenyl)-4-methylpiperidine-1-car-
  boxamidine
N-(2-morpholiniphenyl)thiamorpholine-1-carbox-
  amidine
1,1-dimethyl-2-(5-chloro-2-morpholinophenyl)guani-
  dine
1,1-dimethyl-2-(5-fluoro-2-morpholinophenyl)guani-
  dine
1,1-dimethyl-2-(3-methyl-2-morpholinophenyl)guani-
  dine
1,1-dimethyl-2-(4-methoxy-2-morpholinophenyl)-
  guanidine
1,1-dimethyl-2-(5-isobutyl-2-morpholinophenyl)
  guanidine
1,1-dimethyl-2-(5-methylsulphinyl-2-morpholino-
  phenyl)guanidine
4-[2-(1,3-dimethyl-2-imidazolidinylideneamino)ben-
  zyl]morpholine
4-[4-chloro-2-(1,3-dimethyl-2-
  imidazolidinylideneamino)benzyl]morpholine
N,N-dimethyl-N'-(2-morpholinomethylphenyl)-
  guanidine
N-(2-morpholinomethylphenyl)morpholine-4-car-
  boxamidine
and pharmaceutically acceptable salts thereof.

One group of preferred compounds of formula I includes compounds of formula I in which n=0, —NR$_1$R$_2$ is morpholino, thiamorpholino, piperidino or 1-pyrrolidinyl, R$_3$ is —NH$_2$, R$_5$ is an aliphatic group containing 1 to 4 carbon atoms (eg methyl, ethyl or allyl), R$_6$ is an aliphatic group of 1 to 4 carbon atoms optionally substituted by methoxy or methylthio (eg methyl, ethyl, allyl, methoxyethyl or methylthioethyl) or R$_5$ and R$_6$ together with the nitrogen atom to which they are attached form a heterocyclic ring of formula VI (e.g. morpholino or thiamorpholino) and R$_7$ is H, fluoro, chloro, methyl, ethyl, methylthiomethyl or methylthio.

Specific compounds falling within this one group of preferred compounds include:
  1,1-dimethyl-2-(2-morpholinophenyl)guanidine
  1,1-dimethyl-2-(5-fluoro-2-morpholinophenyl)guani-
    dine
  1,1-dimethyl-2-(5-chloro-2-morpholinophenyl)guani-
    dine
  1,1-dimethyl-2-(5-methyl-2-morpholinophenyl)guani-
    dine
  1,1-dimethyl-2-(6-methyl-2-morpholinophenyl)guani-
    dine
  1,1-dimethyl-2-(5-ethyl-2-morpholinophenyl)guani-
    dine
  1,1-dimethyl-2-(5-methylthiomethyl-2-morpholino-
    phenyl)guanidine
  1,1-dimethyl-2-(5-methylthio-2-morpholinophenyl)
    guanidine
  1-ethyl-1-methyl-2-(2-morpholinophenyl)guanidine
  1,1-diethyl-2-(2-morpholinophenyl)guanidine
  1-(2-methoxyethyl)-1-methyl-2-(2-morpholino-
    phenyl)guanidine
  1-methyl-1-(2-methylthioethyl)-2-(2-morpholino-
    phenyl)guanidine
  1,1-dimethyl-2-(2-thiamorpholinophenyl)guanidine
  1,1-dimethyl-2-(2-piperidinophenyl)guanidine
  1,1-dimethyl-2-[2-(1-pyrrolidinyl)phenyl]guanidine
  N-(2-morpholinophenyl)morpholine-4-carboxami-
    dine
  N-(2-morpholinophenyl)thiamorpholine-4-carbox-
    amidine
and pharmaceutically acceptable salts thereof.

A second group of preferred compounds of formula I includes compounds of formula I in which n=0, —NR$_1$R$_2$ is morpholino or thiamorpholino, R$_3$ is a group of formula III in which R$_4$ is an alkyl group containing 1 to 4 carbon atoms (eg methyl) and R$_4'$ is H, R$_5$ is H, R$_6$ is an aliphatic group containing 1 to 4 carbon atoms (eg methyl, butyl or t-butyl) optionally substituted by methoxy (e.g. R$_6$ is methoxyethyl) and R$_7$ is H, fluoro, methyl, methylthio or methylthiomethyl.

Specific compounds falling within this second group of preferred compounds include:
  1-butyl-3-methyl-2-(2-morpholinophenyl)guanidine
  1-methyl-3-tert-butyl-2-(2-morpholinophenyl)guani-
    dine
  1-methyl-3-tert-butyl-2-(4-fluoro-2-morpholino-
    phenyl)guanidine
  1-methyl-3-tert-butyl-2-(4-methyl-2-morpholino-
    phenyl)guanidine
  1-methyl-3-tert-butyl-2-(4-methylthio-2-morpholino-
    phenyl)guanidine
  1-methyl-3-tert-butyl-2-(4-methylthiomethyl-2-mor-
    pholinophenyl)guanidine
  1-(2-methoxyethyl)-3-methyl-2-(2-morpholino-
    phenyl)guanidine
  1,3-dimethyl-2-(2-thiamorpholinophenyl)guanidine
  1-methyl-3-tert-butyl-2-(2-thiamorpholinophenyl)
    guanidine
and pharmaceutically acceptable salts thereof A further group of preferred compounds of formula I includes compounds of formula I in which n=0, —NR$_1$R$_2$ is morpholino, thiamorpholino, morpholinomethyl or thiamorpholinomethyl, $R_3$ is an alkyl group of 1 to 4 carbon atoms (eg methyl and t-butyl), $R_5$ and $R_6$ are H and $R_7$ is H, fluoro, methyl, methylthio or methylthiomethyl.

Specific compounds falling within this further group of preferred compounds include:

N-(2-morpholinophenyl)acetamidine
N-(4-fluoro-2-morpholinophenyl)acetamidine
N-(4-methyl-2-morpholinophenyl)acetamidine
N-(4-methylthio-2-morpholinophenyl)acetamidine
N-(4-methylthiomethyl-2-morpholinophenyl-)acetamidine
N-(2-thiamorpholinophenyl)acetamidine
N-(2-morpholinomethylphenyl)acetamidine
N-(2-morpholinophenyl)pivalamidine
N-(2-morpholinomethylphenyl)pivalamidine
and pharmaceutically acceptable salts thereof.

Compounds of formula I may exist as salts with pharmaceutically acceptable acids. Examples of such salts include hydrochlorides, hydrobromides, hydroiodides, sulphates, nitrates, maleates, acetates, citrates, fumarates, tartrates, succinates, benzoates, pamoates and salts with acidic amino acids such as glutamic acid. Compounds of formula I and their salts may exist in the form of solvates (for example hydrates).

Some compounds of formula I contain one or more asymmetric carbon atoms and exist in different optically active forms. When the compounds of formula I contain one chiral centre the compounds exist in two enantiomeric forms and the present invention includes both enantiomeric forms and mixtures thereof. When the compounds of formula I contain more than one chiral centre, the compounds may exist in diastereoisomeric forms. The present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 50 to 500 mg of the active compound. Other compositions for oral administration include, for example, aqueous solutions containing the active compound, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat hyperglycemia in human beings. In such treatment the amount of the compound of formula I administered per day is in the range 50 to 3000 mg. The preferred administration route is oral administration.

Processes for the preparation of compounds of formula I will now be described. These processes form a further aspect of the present invention.

Compounds of formula I may be prepared by the reaction of an aminophenyl compound of formula VII

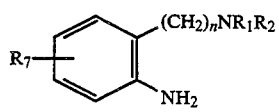

with an amide or a urea of formula $R_3.CO.NR_5R_6$ in the presence of a condensing agent such as phosphorus oxychloride, thionyl chloride, phosgene, phosphorus pentachloride or benzenesulphonyl chloride.

Compounds of formula I in which the groups $R_3$ and $R_5$ together with the carbon and nitrogen atoms to which they are attached form a ring represented by formula IV may be prepared by the reaction of an aminophenyl compound of formula VII with a) a lactam of formula VIII

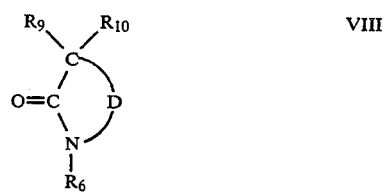

in the presence of a condensing agent such as phosphorus oxychloride, thionyl chloride, cyanuric chloride, phosgene, carbon tetrachloride/triphenylphosphine, phosphorus pentachloride or benzenesulphonyl chloride.

b) a compound of formula IX

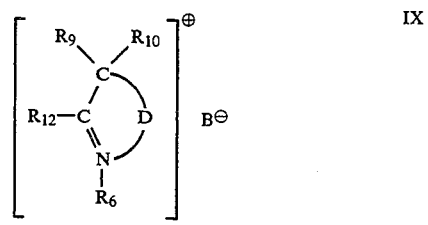

in which $R_{12}$ is chloro, $-O-POCl_2$, $-O-SOCl$, $-O-COCl$ or $-OSO_2Ph$ and $B^-$ is an anion such as halo (e.g. $Cl^-$) or $POCl_4^-$, c) a compound of formula X

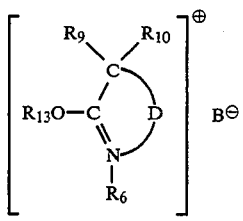

in which $R_{13}$ is an alkyl group and $B^-$ is an anion such as fluoroborate or methosulphate.

d) when $R_6$ is H, a ketoxime of formula XI

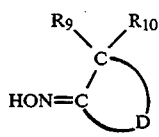

in the presence of a sulphonyl chloride (for example benzene sulphonyl chloride).

Compounds of formula I in which the groups $R_3$ and $R_5$ together with the carbon and nitrogen atoms to which they are attached form a ring represented by formula V may be prepared by the reaction of an aminophenyl compound of formula VII with a urea of formula XII

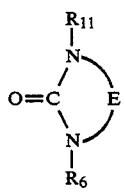

in the presence of a condensing agent such as phosphorus oxychloride, thionyl chloride, phosgene, phosphorus pentachloride or benzenesulphonyl chloride.

Compounds of formula I in which the groups $R_3$ and $R_5$ together with the carbon and nitrogen atoms to which they are attached form a ring represented by formula V may be prepared by the reaction of a compound of formula XIII

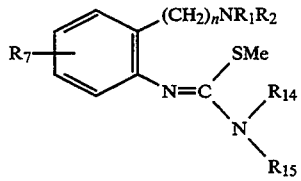

optionally in the form of a salt (e.g. a hydroiodide salt) in which $R_{14}$ and $R_{15}$ are H with a diamine of formula XIV

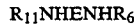

Compounds of formula I in which $R_3$ is a straight or branched alkyl group of 1 to 7 carbon atoms or a cycloalkyl group of 3 to 7 carbon atoms and the group $NR_5R_6$ is $NH_2$ may be prepared by the reaction of a compound of formula VII optionally in the form of a salt (e.g. a hydrochloride salt) with a cyano compound of formula $R_3CN$, optionally in the presence of aluminium chloride.

Compounds of formula I in which the group $R_3$ is $NH_2$ may be prepared by the reaction of a compound of formula VII optionally in the form of a salt (e.g. a hydrochloride salt) with a cyanamide compound of formula $R_5R_6NCN$. The reaction may be performed in a liquid reaction medium (for example m-cresol) or by heating the reactants together in the absence of a liquid carrier.

Compounds of formula I in which the group $R_3$ is $NH_2$ may be prepared by the reaction of compounds of formula XV

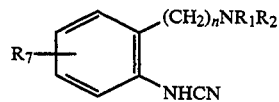

with amines of formula $NHR_5R_6$ optionally in a liquid reaction medium (for example ethanol).

Compounds of formula I in which $R_3$ is a group of formula III in which $R_4$ is alkyl and $R_4'$ is H or alkyl may be prepared by the reaction of a compound of formula XIII in which $R_{14}$ is the group $R_4$ and $R_{15}$ is the group $R_4'$ with an amine of formula $HNR_5R_6$. The reaction may be performed in an alcoholic medium (e.g. ethanol or n-butanol) optionally in the presence of a base such as pyridine or triethylamine or in the presence of potassium hydroxide and lead acetate. When $HNR_5R_6$ is ammonia, the ammonia may be dissolved in the alcoholic medium and the reaction may be performed under elevated pressure in a sealed reaction vessel.

Compounds of formula I in which $R_3$ is a group of formula III in which $R_4$ is alkyl and $R_4'$ is H or alkyl may be prepared by the reaction of a thiourea of formula XVI

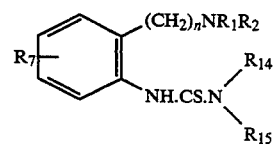

in which $R_{14}$ is the group $R_4$ and $R_{15}$ is the group $R_4'$ with an amine of formula $HNR_5R_6$. The reaction may be performed in the presence of a base (such as potassium hydroxide or potassium carbonate) and lead acetate. When $HNR_5R_6$ is ammonia, the ammonia may be dissolved in an alcoholic medium (e.g. ethanol) and the reaction may be performed under elevated pressure in a sealed reaction vessel.

Compounds of formula I in which $R_3$ is a group of formula III in which $R_4$ is alkyl and $R_4'$ is H and in which $R_5$ is H may be prepared by the reaction of a carbodiimide of formula XVII

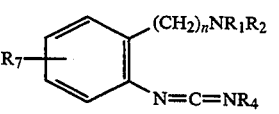

with an amine of formula $H_2NR_6$.

Compounds of formula I in which $n=0$ and $NR_1R_2$ is a morpholino, thiamorpholino, 1-pyrrolidinyl or piperidino group may be prepared by the reaction of a compound of formula XVIII

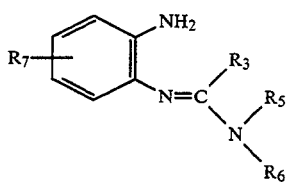

with a disubstituted compound of formula XIX

K(CH$_2$)$_2$L(CH$_2$)$_2$K      XIX in which K is a leaving group such as halo (e.g. bromo or chloro) or tosyloxy and L is —O—, —S—, a direct bond or —CH$_2$—.

Compounds of formula I in which R$_3$ is a group of formula III in which R$_4$ is propyl and R$_4'$ is H and in which R$_5$ is H and R$_6$ is propyl may be prepared by the reaction of an amine of formula H$_2$NR$_6$ in which R$_6$ is propyl with a thiourea of formula XVI in which R$_{14}$ and R$_{15}$ are both methyl in the presence of potassium hydroxide and lead acetate. In this reaction the amino group —NHR$_6$ replaces both the thioxo group and the dimethylamino group.

Compounds of formula I in which R$_3$ is a group of formula III and in which R$_4$ is methyl and R$_4'$ is H and in which R$_5$ is H and R$_6$ is methyl may be prepared by the reaction of an amine of formula H$_2$NR$_6$ in which R$_6$ is methyl with a compound of formula XIII in which the group NR$_{14}$R$_{15}$ is butylamino. In this reaction the amino group —NHR$_6$ replaces both the methylthio group and the amino group —NR$_{14}$R$_{15}$.

Compounds of formula I in which NR$_1$R$_2$ is a thiamorpholino-1-oxide group may be prepared by the oxidation (for example using sodium metaperiodate) of a compound of formula I in which —NR$_1$R$_2$ is thiamorpholino.

Compounds of formula I in which R$_6$ is substituted by an acyloxy group may be prepared by acylation (e.g. acetylation or benzoylation) of the corresponding compound of formula I in which R$_6$ is substituted by hydroxy.

Compounds of formula I in which R$_7$ is an alkylsulphinyl group may be prepared by oxidation (for example using sodium metaperiodate) of compounds of formula I in which R$_7$ is an alkylthio group.

Compounds of formula VII may be prepared by the reduction of the nitro group in a compound of formula XX

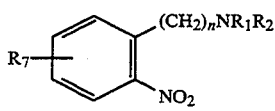

for example (a) using hydrogen and a Raney nickel catalyst, (b) hydrogen and a palladium/carbon catalyst, (c) sodium sulphide, (d) stannous chloride dihydrate in hydrochloric acid, ethyl acetate or ethanol or (e) iron in the presence of acid.

Compounds of formula IX in which R$_{12}$ is a group of formula OPOCl$_2$, OSOCl, OCOCl and OSO$_2$Ph may be prepared by the reaction of compounds of formula VIII with phosphorus oxychloride, thionyl chloride, phosgene or benzenesulphonyl chloride respectively.

Compounds of formula X may be prepared by the reaction of compounds of formula VIII with alkylating agents such as dialkylsulphate, trialkyloxonium fluoroborate or borontrifluoride etherate/diazoalkanes followed by basification with sodium carbonate or sodium hydroxide solution.

Compounds of formula XIII may be prepared by the reaction of methyl iodide with thioureas of formula XVI.

Compounds of formula XV may be prepared by the reaction of potassium hydroxide with compounds of formula XIII in which R$_{14}$ and R$_{15}$ are both H or in which R$_{14}$ is benzoyl and R$_{15}$ is H in the presence of lead acetate.

Compounds of formula XV may be prepared by the reaction of thioureas of formula XVI in which R$_{14}$ and R$_{15}$ are H with sodium chlorite in the presence of a base such as sodium carbonate and a copper catalyst such as a mixture of cuprous and cupric chlorides.

Thioureas of formula XVI in which R$_{14}$ and R$_{15}$ are H may be prepared by the reaction of ammonia with an isothiocyanate of formula XXI

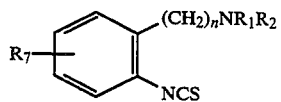

Compounds of formula XVI in which R$_{14}$ is an alkyl group and R$_{15}$ is H may be prepared by the reaction of an aminophenyl of formula VII with an alkylisothiocyanate of formula R$_{14}$NCS.

Carbodiimides of formula XVII may be prepared by the reaction of thiourea of formula XVI in which R$_{14}$ is the group R$_4$ and R$_{15}$ is H with sodium chlorite.

Compounds of formula XVIII may be prepared by the reduction for example by hydrogen and Raney nickel of compounds of formula XXII

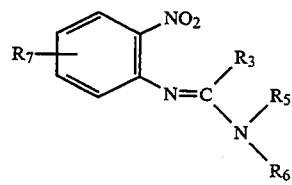

Compounds of formula XX in which n=0 and NR$_1$R$_2$ is a morpholino, thiamorpholino, 1-pyrrolidinyl or piperidino group may be prepared by the reaction of a 2-nitroaniline with a compound of formula XIX. Compounds of formula XX in which n=0 and —NR$_1$R$_2$ is morpholino, thiamorpholino, 1-pyrrolidinyl, piperidino, 1-hexa-hydroazepinyl or 4-methyl-1-piperazinyl may be prepared by the reaction of morpholine, thiamorpholine, pyrrolidine, piperidine, 1-hexahydroazepine and 4-methyl-1-piperazine respectively with a halonitrobenzene (e.g. 2-fluoronitrobenzene or 2-chloronitrobenzene) in the absence or presence of a solvent such as benzene, ethanol or acetonitrile.

Compounds of formula XXI may be prepared by the reaction of a compound of formula VII with thiophosgene in a liquid reaction medium such as dioxan.

Compounds of formula XXII may be prepared by the reaction of an amide or urea of formula R$_3$.CO.NR$_5$R$_6$ with a 2-nitroaniline in the presence of a condensing agent (such as phosphorus oxychloride or thionylchloride). Compounds of formula XXII may be prepared by the reaction of an amidine or guanidine of formula $R_3.CNH.NR_5R_6$ with a 2-halonitrobenzene (e.g. 2-fluoronitrobenzene or 2-chloronitrobenzene).

The hypoglycemic activity of the compounds of formula I which are given in the following Examples has been demonstrated by the following test. Rats weighing between 150 and 200 g were fasted for 18 hours and then were subcutaneously injected with glucose (800 mg/4 ml/kg) followed by an oral dose of the compound to be tested (x mg in either 4 or 5 ml of 0.2% Agar/kg). After 2 and 4 hours blood was collected by orbital bleeding and the plasma glucose estimated on a Beckman glucose analyser using the specific glucose oxidase method (Kadish A. H., Little R. L. and Sternberg J. C., Clin chem 14 116 [1968]). The percentage reduction of plasma glucose when compared to control animals which had not been given the compound to be tested, but which had been given 0.2% Agar homogenate, was then calculated. Compounds are considered to have hypoglycaemic activity in this test if they show a 15% or greater reduction in plasma glucose at any value of x up to 200 at either or both of 2 and 4 hours.

The results obtained at any value of x in the above tests were then reviewed and the hypoglycaemic activity of each compound was classified on the following scale. Where more than one set of results is available at a particular value of x, the mean value of the % reduction is used to classify the activity of the compounds.

A greater than 25% reduction at both 2 and 4 hours.
B greater than 25% reduction at 2 hours but less than 25% reduction at 4 hours.
C reduction in the range 15 to 25% at 2 hours but greater than 25% reduction at 4 hours.
D reduction in the range 15 to 25% at both 2 and 4 hours.
E reduction in the range 15 to 25% at 2 hours but less than 15% reduction at 4 hours.
F less than 15% reduction at 2 hours but greater than 15% reduction at 4 hours.

The activities of the compounds described in the Examples given hereinafter are given below in Table A.

TABLE A

| Example | x | Activity | Example | x | Activity |
|---|---|---|---|---|---|
| 1 | 25 | A | 2 | 25 | B |
| 3 | 25 | B | 4 | 25 | B |
| 5 | 25 | A | 6 | 25 | E |
| 7 | 25 | B | 8 | 36 | B |
| 9 | 200 | E | 10 | 25 | B |
| 11 | 25 | A | 12 | 25 | A |
| 13 | 50 | D | 14 | 200 | A |
| 15 | 100 | E | 16 | 25 | D |
| 17 | 50 | B | 18 | 25 | E |
| 19 | 40 | A | 20 | 25 | A |
| 21 | 25 | C | 22 | 25 | B |
| 23 | 50 | A | 24 | 25 | B |
| 25 | 25 | D | 26 | 25 | B |
| 27 | 25 | A | 28 | 25 | A |
| 29 | 25 | E | 30 | 25 | D |
| 31 | 50 | D | 32 | 25 | D |
| 33 | 25 | B | 34 | 25 | B |
| 35 | 25 | D | 36 | 200 | F |
| 37 | 200 | E | 38 | 200 | D |
| 39 | 200 | A | 40 | 200 | A |
| 41 | 200 | A | 42 | 36 | D |
| 43 | 25 | B | 44 | 200 | A |
| 45 | 200 | D | 46 | 36 | B |
| 47 | 37 | B | 48 | 200 | A |
| 49 | 38 | E | 50 | 36 | A |
| 51 | 200 | D | 52 | 36 | B |
| 53 | 36 | B | 54 | 37 | B |
| 55 | 36 | A | 56 | 35 | A |
| 57 | 25 | A | 58 | 25 | B |
| 59 | 35 | A | 60 | 37 | E |
| 61 | 36 | D | 62 | 25 | C |
| 63 | 100 | A | 64 | 25 | B |
| 65 | 25 | A | 66 | 36 | D |
| 67 | 200 | A | 68 | 25 | C |
| 69 | 43 | D | 70 | 36 | A |
| 71 | 36 | A | 72 | 25 | B |
| 73 | 25 | A | 74 | 25 | A |
| 75 | 50 | F | 76 | 25 | D |
| 77 | 25 | E | 78 | 25 | F |
| 79 | 200 | A | 80 | 25 | D |
| 81 | 200 | D | 82 | 50 | E |
| 83 | 25 | A | 84 | 25 | E |
| 85 | 25 | D | 86 | 25 | F |
| 87 | 200 | D | 88 | 200 | F |
| 89 | 200 | C | 90 | 25 | E |
| 91 | 200 | A | 92 | 25 | B |
| 93 | 25 | C | 94 | 200 | C |
| 95 | 25 | E | 96 | 25 | F |
| 97 | 50 | D | 98 | 50 | A |
| 99 | 25 | A | 100 | 25 | B |
| 101 | 25 | B | 102 | 200 | A |
| 103 | 25 | B | 104 | 27 | A |
| 105 | 37 | E | 106 | 37 | E |
| 107 | 25 | B | 108 | 25 | B |
| 109 | 25 | B | 110 | 36 | B |
| 111 | 25 | B | 112 | 36 | B |
| 113 | 25 | D | 114 | 25 | E |
| 115 | 25 | D | 116 | 25 | B |
| 117 | 25 | B | 118 | 25 | A |
| 119 | 25 | D | 120 | 25 | B |
| 121 | 25 | E | 122 | 25 | A |
| 123 | 38 | B | 124 | 37 | B |
| 125 | 36 | B | 126 | 200 | A |
| 127 | 25 | E | 128 | 25 | A |
| 129 | 25 | B | 130 | 100 | B |
| 131 | 50 | B | 132 | 200 | A |
| 133 | 25 | B | 134 | 25 | A |
| 135 | 25 | A | 136 | 25 | B |
| 137 | 25 | B | 138 | 25 | B |
| 139 | 25 | B | 140 | 100 | A |
| 141 | 25 | E | 142 | 25 | A |
| 143 | 25 | B | 144 | 25 | B |
| 145 | 25 | C | 146 | 200 | A |
| 147 | 36 | D | 148 | 25 | D |
| 149 | 36 | D | 150 | 68 | F |
| 151 | 25 | C | 152 | 25 | D |
| 153 | 25 | B | 154 | 39 | D |
| 155 | 133 | B | 156 | 25 | D |
| 157 | 25 | A | 158 | 25 | A |
| 159 | 50 | D | 160 | 26 | D |
| 161 | 34 | A | 162 | 35 | B |
| 163 | 25 | B | 164 | 25 | D |
| 165 | 200 | B | 166 | 25 | D |
| 167 | 25 | B | 168 | 25 | B |
| 169 | 25 | A | 170 | 25 | A |
| 171 | 25 | D | 172 | 25 | D |
| 173 | 25 | D | 174 | 25 | B |
| 175 | 25 | B | 176 | 35 | C |
| 177 | 25 | B | 178 | 200 | A |
| 179 | 25 | D | 180 | 25 | E |
| 181 | 43 | D | 182 | 25 | D |
| 183 | 25 | D | 184 | 34 | F |
| 185 | 200 | D | 186 | 25 | A |
| 187 | 25 | A | 188 | 25 | B |
| 189 | 25 | A | 190 | 25 | A |
| 191 | 36 | D | 192 | 25 | B |
| 193 | 25 | A | 194 | 200 | C |
| 195 | 12.5 | A | 196 | 25 | A |
| 197 | 25 | D | 198 | 25 | A |
| 199 | 25 | B | 200 | 25 | A |
| 201 | 25 | E | 202 | 25 | B |
| 203 | 100 | A | 204 | 200 | A |
| 205 | 200 | A | 206 | 200 | C |
| 207 | 50 | A | 208 | 30 | D |
| 209 | 25 | B | 210 | 30 | D |

TABLE A-continued

| Example | x | Activity | Example | x | Activity |
|---|---|---|---|---|---|
| 211 | 36 | A | 212 | 25 | F |
| 213 | 50 | D | 214 | 25 | E |
| 215 | 25 | E | 216 | 35 | A |
| 217 | 30 | E | 218 | 200 | D |
| 219 | 200 | D | 220 | 36 | A |
| 221 | 200 | A | 222 | 35 | A |
| 223 | 35 | D | 224 | 35 | C |
| 225 | 25 | B | 226 | 200 | A |
| 227 | 25 | F | 228 | 35 | A |
| 229 | 35 | A | 230 | 35 | C |
| 231 | 35 | F | 232 | 25 | B |
| 233 | 25 | B | 234 | 25 | B |
| 235 | 34 | A | 236 | 38 | C |
| 237 | 35 | A | 238 | 35 | A |
| 239 | 35 | A | 240 | 36 | A |
| 241 | 34 | A | 242 | 200 | A |
| 243 | 200 | B | 244 | 200 | E |
| 245 | 25 | B | 246 | 200 | D |
| 247 | 37 | A | 248 | 36 | A |
| 249 | 36 | B | 250 | 25 | E |
| 251 | 35 | E | 252 | 200 | A |
| 253 | 35 | A | 254 | 36 | B |
| 255 | 36 | A | 256 | 34 | B |
| 257 | 36 | A | 258 | 35 | E |
| 259 | 34 | D | 260 | 35 | B |
| 261 | 36 | C | 262 | 37 | B |
| 263 | 38 | B | 264 | 36 | B |
| 265 | 200 | E | 266 | 200 | E |
| 267 | 200 | E | 268 | 35 | B |
| 269 | 35 | B | 270 | 25 | B |
| 271 | 25 | B | 272 | 25 | B |
| 273 | 200 | C | 274 | 128 | D |
| 275 | 25 | E | 276 | 36 | B |
| 277 | 34 | B | 278 | 35 | B |
| 279 | 25 | B | 280 | 35 | B |
| 281 | 35 | A | 282 | 200 | C |
| 283 | 200 | E | 284 | 200 | E |
| 285 | 200 | B | 286 | 35 | B |
| 287 | 36 | B | 288 | 38 | E |
| 289 | 200 | A | 290 | 25 | D |
| 291 | 25 | B | 292 | 85 | C |
| 293 | 35 | A | 294 | 25 | B |
| 295 | 25 | B | 296 | 25 | D |
| 297 | 35 | B | 298 | 35 | E |
| 299 | 34 | E | 300 | 200 | A |
| 301 | 25 | B | 302 | 38 | A |
| 303 | 39 | B | 304 | 40 | B |
| 305 | 28 | A | 306 | 29 | A |
| 307 | 30 | B | 308 | NT | |
| 309 | 100 | D | 310 | 200 | D |
| 311 | 200 | E | 312 | 200 | E |

NT = Not Tested

The present invention will be illustrated by the following Examples which are given by way of example only. The final product of each of the Examples was characterised by elemental analyses.

EXAMPLE 1

A solution of delta-valerolactam (24 g) in dry benzene (100 ml) was cooled to 10° C. in ice-water and treated with freshly distilled phosphorus oxychloride (22.2 ml) under nitrogen over a period of 10-15 minutes. The initial white solid formed changed to a clear yellow oil over 3 hours. A solution of 4-(2-aminophenyl)morpholine (36 g) in dry benzene (150 ml) was added and the mixture heated at 65° C. with stirring for 32 hours. The benzene layer was decanted, the oil washed twice with benzene (2×40 ml), ether (100 ml) was added and the mixture cooled in ice treated with 10% aqueous sodium hydroxide solution to alkaline pH, with stirring. The aqueous layer was extracted with ether (2×100 ml) and the combined ether extracts washed with water, brine and dried. The solution was filtered and the solvent removed to give a thick oil which solidified on trituration with hexane. The crude solid was crystallised from hot hexane to yield 4-[2-(2-piperidinylideneamino)phenyl]morpholine (m.p. 89°-90° C.).

EXAMPLE 2

A solution of the product of Example 1 (10.2 g) in dry methanol (30 ml) was treated with fumaric acid (4.6 g). The resulting solid was filtered and crystallised from methanol to yield 4-[2-(2-piperidinylideneamino)phenyl]morpholine fumarate as a colourless crystalline solid [m.p. 210° C. (dec)].

EXAMPLES 3 to 35

In a similar manner to that described above in Example 1 the compounds listed in Table I were prepared by the reaction of an aminophenyl compound of formula VII in which $NR_1R_2$ is morpholino (A grammes in B ml benzene) with a compound of formula VIII (C grammes in D ml benzene) in the presence of phosphorus oxychloride (E ml) for F hours at a temperature in the range 60°-70° C.

Notes to Table I (1) Product recrystallised from hexane.

(2) The product was purified by chromatography on an alumina column using a 1:1 mixture of dichloromethane and hexane as eluant.

(3) Product isolated as its hydroiodide salt which was recrystallised from a 1:1 mixture of methanol and ether.

(4) Coupling reaction performed at ambient temperature.

(5) Product recrystallised from ether.

(6) The compound of formula VIII was dissolved in a mixture of benzene (60 ml) and acetonitrile (40 ml).

(7) The product was purified by chromatography on an alumina column using the following eluants sequentially:—hexane, a 1:9 mixture of dichloromethane and hexane, a 3:7 mixture of dichloromethane and hexane, a 1:1 mixture of dichloromethane and hexane and dichloromethane.

(8) The product was isolated as its monofumarate salt which was recrystallised from 1:1 mixture of methanol and ether.

(9) The product was isolated as its monohydroiodide salt which was recrystallised from a 2:3 mixture of methanol and ether.

(10) Coupling reaction performed at ambient temperature for 24 hours and at 70° C. for 8 hours.

(11) Product isolated as its fumarate salt which was recrystallised from propan-2-ol.

(12) Product isolated as its sesquifumarate salt which was recrystallised from a 1:1 mixture of methanol and ether.

(13) The compound of formula VIII was dissolved in acetonitrile (120 ml).

(14) The product was purified by chromatography on an alumina column using a 99:1 mixture of dichloromethane and methanol as eluant. The product was recrystallised from a 1:1 mixture of dimethoxyethane and hexane.

TABLE I

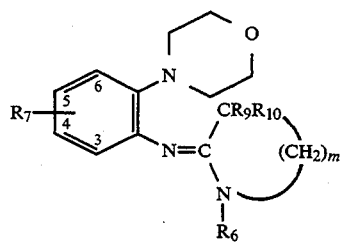

| Ex. | A | B | C | D | E | F | m | R7 | R9 | R10 | R6 | mp(°C.) | Notes |
|---|---|---|---|---|---|---|---|---|---|---|---|---|---|
| 3 | 17.8 | 75 | 16.4 | 100 | 13.3 | 6 | 3 | H | H | H | Me | 130 | (1) |
| 4 | 5.3 | 20 | 5.7 | 40 | 4.1 | 4 | 3 | H | H | H | Et | 92–93 | (1) |
| 5 | 5.4 | 25 | 6.3 | 50 | 4.1 | 2 | 3 | H | H | H | i-Pr | 104–105 | (1) |
| 6 | 5 | 25 | 4 | 25 | 3.3 | 40 | 4 | H | H | H | H | 96–98 | (1)(2) |
| 7 | 5.4 | 30 | 7.5 | 50 | 5.5 | 6 | 4 | H | H | H | Me | 79–80 | (1) |
| 8 | 10 | 25 | 12.7 | 50 | 9 | 6 | 5 | H | H | H | H | 231–232 | (3) |
| 9 | 3.6 | 10 | 2 | 20 | 2.4 | 6 | 2 | H | H | H | H | 143 | (1) |
| 10 | 10.7 | 60 | 7.2 | 120 | 7.2 | 8 | 2 | H | H | H | Me | 89–90 | (1) |
| 11 | 3.6 | 10 | 2.8 | 20 | 2.4 | 6 | 2 | H | Me | H | Me | 105–107 | (1)(4) |
| 12 | 3.6 | 10 | 3.2 | 30 | 2.4 | 14 | 2 | H | Me | Me | Me | 72–75 | (1) |
| 13 | 4.5 | 10 | 3.5 | 25 | 3 | 5 | 2 | H | H | H | Et | 94–96 | (1) |
| 14 | 3.6 | 25 | 4.3 | 50 | 2.7 | 5 | 2 | H | H | H | $CH_2CH_2OMe$ | 140–142 | (7)(9) |
| 15 | 7.1 | 80 | 10 | 40 | 5.5 | 8 | 2 | H | H | H | cyclohexyl | 110–112 | (1) |
| 16 | 3.5 | 10 | 3.4 | 30 | 2.4 | 5 | 2 | H | Me | Me | Et | 72–74 | (1) |
| 17 | 3.6 | 30 | 3.8 | 15 | 2.4 |   | 2 | H | Et | Et | Me | 190 | (10)(11) |
| 18 | 3.4 | 15 | 3.3 | 25 | 2.4 | 12 | 2 | H | i-Pr | H | Me | 70 | (1) |
| 19 | 2.5 | 30 | 1.9 | 60 | 1.4 | 10 | 3 | H | Me | H | Me | 184 | (12) |
| 20 | 6.8 | 30 | 8 | 50 | 7.3 | 5.5 | 3 | 3-Me | H | H | H | 167–168 | (1) |
| 21 | 3.1 | 25 | 2.7 | 25 | 2.2 | 4 | 3 | 3-Me | H | H | Me | 110–111 | (1) |
| 22 | 6.8 | 30 | 8 | 50 | 7.3 | 4.5 | 3 | 4-Me | H | H | H | 114 | (1) |
| 23 | 3.8 | 25 | 2.7 | 25 | 2.2 | 4 | 3 | 4-Me | H | H | Me | 108–109 | (1) |
| 24 | 6 | 30 | 6.3 | 50 | 5.8 | 10 | 3 | 5-Me | H | H | H | 119 | (1) |
| 25 | 2.5 | 10 | 3 | 20 | 2.7 | 10 | 3 | 6-Me | H | H | H | 98 | (1) |
| 26 | 4.1 | 20 | 4 | 30 | 3.7 | 5 | 3 | 4-Et | H | H | H | 204–205 | (7)(8) |
| 27 | 3 | 10 | 3 | 20 | 2.7 | 5 | 3 | 3-Cl | H | H | H | 166–167 | (5) |
| 28 | 5 | 40 | 5.25 | 30 | 3.4 | 8 | 3 | 4-Cl | H | H | H | 109–110 | (1) |
| 29 | 4.2 | 25 | 2.7 | 25 | 2.2 | 4 | 3 | 4-Cl | H | H | Me | 108–109 | (1) |
| 30 | 6.3 | 25 | 6 | 50 | 5.5 | 4.5 | 3 | 5-Cl | H | H | H | 140–141 | (1) |
| 31 | 6.3 | 20 | 6 | 40 | 5.8 | 4 | 3 | 6-Cl | H | H | H | 115–116 | (1) |
| 32 | 5 | 50 | 6 | 30 | 5.6 | 5 | 3 | 4-F | H | H | H | 82–83 | (1) |
| 33 | 3.7 | 25 | 2.7 | 25 | 2.2 | 4 | 3 | 4-F | H | H | Me | 110–111 | (1) |
| 34 | 3.1 | 20 | 3 | 30 | 2.7 | 5 | 3 | 4-OMe | H | H | H | 103–104 | (1) |
| 35 | 4.6 |   | 4 | 40 | 3.6 | 4 | 3 | 4-COOMe | H | H | H | 112–114 | (1)(6) |
| 36 | 5.1 |   | 8 | 60 | 2.2 | 3 | 3 | 4-$SO_2Me$ | H | H | H | 151–152 | (13)(14) |
| 37 | 6.3 | 30 | 6.8 | 40 | 3.4 | 7 | 3 | H | H | H | $CH_2CH_2OAc$ | 66–67 | (1) |

EXAMPLE 38

In a similar manner to that described in Examples 1 and 2, 1-methyl-3-(2-methoxyethyl)-2-piperidone (2.56 g) in benzene (30 ml) was reacted with 4-(2-aminophenyl)morpholine (2.49 g) in benzene (30 ml) in the presence of phosphorus oxychloride (1.37 ml) for 12 hours at 70° C. The resulting product was 4-{2-[1-methyl-3-(2-methoxyethyl)-2-piperidinylideneamino]-phenyl}morpholine sesquifumarate (m.p. 174° C.) which was recrystallised from a 1:1 mixture of methanol and ether.

EXAMPLE 39

In a similar manner to that described in Example 1, 1-benzyl-3-methyl-2-pyrrolidone (14.17 g) in benzene (80 ml) was reacted with 4-(2-aminophenyl)morpholine (8.9 g) in benzene (30 ml) in the presence of phosphorus oxychloride (6.86 ml) for 24 hours at 70° C. to give 4-[2-(1-benzyl-3-methyl-2-pyrrolidinylideneamino)-phenyl]morpholine (m.p. 96°–97° C.) which was recrystallised from hexane.

The recrystallised product (2 g) from the previous paragraph was heated at reflux with cyclohexene (6 ml), 10% Pd/C (1.5 g) and methanol (100 ml) for 4 hours to give 4-[2-(3-methyl-2-pyrrolidinylideneamino)phenyl]-morpholine as an oil. This oil (1 g) was dissolved in methanol (20 ml) and a solution of fumaric acid (0.47 g) in methanol was added to yield 4-[2-(3-methyl-2-pyrrolidinylideneamino)phenyl[morpholine fumarate (m.p. 185° C.) which was recrystallised from an 1:1 mixture of methanol and ether.

EXAMPLES 40–62

In a similar manner to that described in Example 1 the compounds listed in Table II were prepared by the reaction of an aminophenyl compound of formula VII (A grammes in B ml benzene) with an amide of formula $R_3.CO.NR_5R_6$ (C grammes in D ml benzene) in the presence of phosphorus oxychloride (E ml) for F hours at a temperature in the range 60°–70° C.

Notes to Table II

Notes (1) and (8) has the meaning given in respect of Table I

(15) The product was isolated as its monofumarate salt which was recrystallised from methanol.

(16) Coupling reaction performed at 80° C.

(17) Coupling reaction performed at 75° C.

(18) Product obtained as a monohydrate.

(19) Product recrystallised twice from n-pentane.

(20) The product was obtained as an oil, the boiling point of which was not determined. The oil was purified by chromatography on an alumina column using the following eluants sequentially:—hexane, a 1:1 mixture of dichloromethane and hexane and dichloromethane.

EXAMPLES 64–75

In a similar manner to that described in Example 1 the compounds listed in Table III were prepared by the reaction of an aminophenyl compound of formula VII in which $NR_1R_2$ is 1-pyrrolidinyl (A grammes in B ml benzene) with a compound of formula VIII (C grammes in D ml benzene) in the presence of phosphorus oxychloride (E ml) for F hours at a temperature in the range of 60°–70° C.

TABLE II

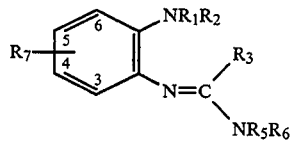

| Ex. | A | B | C | D | E | F | $NR_1R_2$ | $R_3$ | $R_5$ | $R_6$ | $R_7$ | mp(°C.) | Notes |
|---|---|---|---|---|---|---|---|---|---|---|---|---|---|
| 40 | 7.1 | 30 | 7.3 | 50 | 9.1 | 6 | morpholino | Me | H | Me | H | 132–133 | (1) |
| 41 | 6.3 | 35 | 4 | 25 | 3.5 | 10 | morpholino | Me | H | Pr | H | 78–79 | (1) |
| 42 | 7.2 | 35 | 5.1 | 25 | 4 | 9 | morpholino | Me | H | n-Bu | H | 178–179 | (15) |
| 43 | 7.2 | 35 | 5.7 | 25 | 4 | 9 | morpholino | Me | H | n-$C_5H_{11}$ | H | 163–164 | (15) |
| 44 | 10.8 | 40 | 10 | 50 | 6.3 | 18 | morpholino | Me | H | $(CH_2)_2OAc$ | H | 185–186 | (15) |
| 45 | 3.5 | 20 | 2.5 | 20 | 2.3 | 8 | morpholino | Me | Me | Me | H | 68–70 | (1) |
| 46 | 3.5 | 20 | 3 | 20 | 2.3 | 40 | morpholino | Me | Et | Et | H | 166–168 | (8) |
| 47 | 8.9 | 30 | 6.5 | 70 | 6.9 | 12 | morpholino | Et | H | Me | H | 70 | (8) |
| 48 | 5.3 | 30 | 4 | 20 | 3.7 | 5 | morpholino | Et | H | Et | H | 105–107 | (1)(16) |
| 49 | 8.9 | 30 | 7.6 | 70 | 6.9 | 12 | morpholino | Et | Me | Me | H | 170 | (8)(17)(18) |
| 50 | 8.9 | 30 | 7.6 | 75 | 6.9 | 45 | morpholino | Pr | H | Me | H | 180 | (8) |
| 51 | 5.3 | 30 | 4.5 | 20 | 3.7 | 3 | morpholino | Pr | H | Et | H | 75–77 | (16)(19) |
| 52 | 8.9 | 30 | 8.6 | 75 | 6.9 | 45 | morpholino | Pr | Me | Me | H | 135–137 | (8) |
| 53 | 8.9 | 30 | 7.6 | 70 | 6.9 | 12 | morpholino | i-Pr | H | Me | H | 220 | (8)(17) |
| 54 | 8.9 | 30 | 8.6 | 70 | 6.9 | 12 | morpholino | i-Pr | Me | Me | H | 156–160 | (8)(17) |
| 55 | 7.2 | 30 | 5.1 | 35 | 4 | 16 | morpholino | Bu | H | Me | H | 168–169 | (17) |
| 56 | 8.9 | 30 | 10.7 | 80 | 6.9 | 12 | morpholino | Bu | Me | Me | H | 121–122 | (8) |
| 57 | 5.3 | 30 | 5.2 | 40 | 4.1 | 8 | morpholino | —$CMe_3$ | H | Me | H | 128–129 | (1) |
| 58 | 5 | 20 | 5.5 | 20 | 4 | 14 | morpholino | —$CMe_3$ | Me | Me | H | | (20) |
| 59 | 8.9 | 50 | 9.7 | 100 | 6.9 | 10 | morpholino | pentyl | H | Me | H | 134–135 | (8) |
| 60 | 8.1 | 50 | 7 | 80 | 6.4 | 8 | 1-pyrrolidinyl | Pr | H | Me | H | 135–137 | (8) |
| 61 | 3.7 | 20 | 3.9 | 30 | 3.1 | 8 | 1-pyrrolidinyl | —$CMe_3$ | H | Me | H | 193–194 | (8) |
| 62 | 5 | 30 | 4.3 | 25 | 2.6 | 9 | morpholino | cyclohexyl | H | Me | H | 93–94 | (1) |

EXAMPLE 63

A mixture of N-methylpivalamide (11.5 g) in benzene (120 ml) and phosphorus oxychloride (9.2 ml) was stirred at room temperature for 3 days. A solution of 1-(2-aminophenyl)piperidine (14 g) in benzene (80 ml) was added and the mixture heated at 65°–70° C. for four days to give N-methyl-N'-(2-piperidinophenyl)-pivalamidine (m.p. 78° C.) which was recrystallised from hexane. The product was obtained as a 0.25 hydrate.

Notes to Table III

Notes (1), (4) and (8) have the meaning given in respect of Table I.

(21) The product was isolated as its monofumarate salt which was recrystallised from a 1:2 mixture of methanol and ether.

(22) The product was isolated as its monofumarate salt which was recrystallised from a 1:3 mixture of methanol and ether.

TABLE III

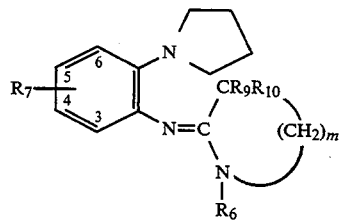

| Ex. | A | B | C | D | E | F | m | $R_7$ | $R_9$ | $R_{10}$ | $R_6$ | mp(°C.) | Notes |
|---|---|---|---|---|---|---|---|---|---|---|---|---|---|
| 64 | 3.2 | 20 | 3 | 20 | 2.8 | 6 | 3 | H | H | H | H | 82–84 | (1) |
| 65 | 3 | 25 | 2.7 | 25 | 2.2 | 5 | 3 | H | H | H | Me | 99–101 | (1) |
| 66 | 4.9 | 20 | 5.7 | 30 | 4.1 | 7 | 3 | H | H | H | Et | 143–144 | (21) |
| 67 | 4 | 25 | 2.7 | 25 | 2.2 | 6 | 3 | 4-Cl | H | H | Me | 77–78 | (1) |
| 68 | 3.5 | 25 | 4 | 25 | 3.3 | 14 | 3 | 3-Me | H | H | Me | 92–93 | (1) |

TABLE III-continued

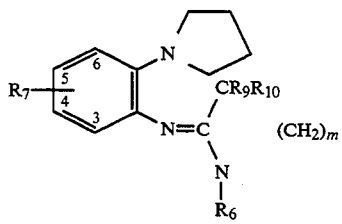

| Ex. | A | B | C | D | E | F | m | R7 | R9 | R10 | R6 | mp(°C.) | Notes |
|---|---|---|---|---|---|---|---|---|---|---|---|---|---|
| 69 | 4 | 25 | 3 | 25 | 2.7 | 8 | 2 | H | H | H | Me | 157–158 | (8) |
| 70 | 4.8 | 25 | 4 | 30 | 3.3 | 8 | 2 | H | Me | H | Me | 152–154 | (22) |
| 71 | 4.8 | 20 | 5.7 | 30 | 4.1 | 8 | 4 | H | H | H | Me | 159–160 | (21) |
| 72 | 8.8 | 90 | 10 | 60 | 9.2 | 8 | 3 | 4-Me | H | H | H | 112–113 | (1) |
| 73 | 1.8 | 30 | 2 | 20 | 1.8 | 24 | 3 | 4-Cl | H | H | H | 138–139 | (1) |
| 74 | 8.8 | 60 | 10 | 60 | 9.2 | 5 | 3 | 3-Me | H | H | H | 113–115 | (1) |
| 75 | 4 | 30 | 4.5 | 30 | 4.2 | 14 | 3 | 6-Me | H | H | H | 83–85 | (1)(4) |

EXAMPLES 76–91

In a similar manner to that described in Example 1 the compounds listed in Table IV were prepared by the reaction of an aminophenyl compound of formula VII (A grammes in B ml benzene) with a 2-piperidone (C grammes in D ml benzene) in the presence of phosphorus oxychloride (E ml) for F hours at a temperature in the range 60°–70° C.

(27) Product was purified by column chromatography on an alumina column using a 49:1 mixture of dichloromethane and methanol as eluant. The product was isolated as its dihydroiodide salt which was recrystallised from a 1:1 mixture of ethanol and ether.

(28) Coupling reaction performed at 90°–100° C.

TABLE IV

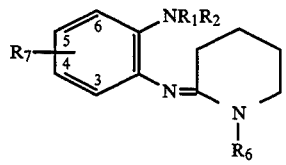

| Ex. | A | B | C | D | E | F | NR1R2 | R7 | R6 | mp(°C.) | Notes |
|---|---|---|---|---|---|---|---|---|---|---|---|
| 76 | 3.5 | 10 | 2.4 | 20 | 2.4 | 5 | thiamorpholino | H | H | 215–217 | (8) |
| 77 | 14 | 40 | 16 | 120 | 15.2 | 12 | piperidino | H | H | 70–72 | (1) |
| 78 | 3.4 | 25 | 2.7 | 25 | 2.2 | 8 | piperidino | H | Me | 87–89 | (1)(23) |
| 79 | 2.8 | 25 | 3 | 30 | 2.7 | 5 | 1-hexahydroazepinyl | H | H | 152–153 | (18) |
| 80 | 5 | 25 | 5 | 50 | 47 | 4 | 2,6-dimethylmorpholino | H | H | 132–135 | (1) |
| 81 | 7.6 | 40 | 8 | 60 | 7.3 | 7 | 4-methylpiperidino | H | H | 145–146 | (24) |
| 82 | 5 | 25 | 6 | 50 | 5.5 | 7 | 1-(1,2,5,6-tetrahydro)pyridyl | H | H | 62 | (1) |
| 83 | 5.3 | 15 | 6 | 30 | 6 | 24 | 2-methyl-1-pyrrolidinyl | H | H | 71 | (1) |
| 84 | 2.8 | 40 | 3 | 20 | 2.7 | 4 | 2-isoindolinyl | H | H | 124–125 | (25) |
| 85 | 3.7 | 25 | 2.6 | 25 | 2.2 | 6 | thiamorpholino | H | Me | 124–125 | (1) |
| 86 | 4.2 | 60 | 4 | 40 | 3.6 | 5 | thiamorpholino | 4-Me | H | 150–151 | (26) |
| 87 | 7.2 | 30 | 8 | 40 | 7.3 | 7 | N(Me)CH2CH2OMe | H | H | 135–136 | (27) |
| 88 | 5.4 | 30 | 8 | 40 | 7.3 | 5 | NMe2 | H | H | 175–176 | (8) |
| 89 | 4.2 | 20 | 4.6 | 40 | 4.3 | 4 | N(allyl)2 | H | H | 62–63 | (1) |
| 90 | 6.1 | 25 | 4.5 | 50 | 4.2 | 14 | N(Me)cyclohexyl | H | H | 183–185 | (11)(28) |
| 91 | 4.2 | 25 | 2.7 | 25 | 2.2 | 8 | N(CH2CH2OMe)2 | H | Me | 129–130 | (21) |

Notes to Table IV

Note (1), (8), (11) and (21) have the meaning given for Tables I and III

(23) Coupling reaction performed at 75°–80° C.

(24) Product isolated as its monofumarate salt which was recrystallised from methanol.

(25) Product was recrystallised from a 1:2 mixture of dimethoxyethane and hexane.

(26) Product recrystallised from hexane and then a mixture of dimethoxyethane and hexane.

EXAMPLES 92–101

In a similar manner to that described in Example 1, the compounds listed in Table V were prepared by the reaction of an aminophenyl compound of formula VII (A grammes in B ml benzene) with a methyl-substituted-2-pyrrolidinone (C grammes in D ml benzene) in the presence of phosphorus oxychloride (E ml) for F hours at a temperature in the range 60°–70° C.

Notes to Table V

Notes (1) and (4) has the meaning given for Table I

(29) Product isolated as its dihydroiodide salt which was recrystallised from a 1:1 mixture of methanol and ether.

(30) Coupling reaction performed at ambient temperature for F hours.

(31) Product isolated as its dihydroiodide salt which was recrystallised from a 1:3 mixture of ethanol and ether.

EXAMPLE 106

Powdered anhydrous aluminium chloride (12 g) was added portion-wise to a stirred slurry of 4-(2-aminophenyl)morpholine (5.34 g) and n-butyronitrile (6 g) at 40°–50° C. The mixture was then heated at 160°–170° C. for 6 hours, allowed to cool and then digested with 40% aqueous sodium hydroxide solution. The solution was

TABLE V

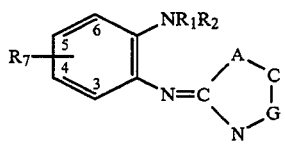

| Ex. | A | B | C | D | E | F | $NR_1R_2$ | A | G | $R_6$ | $R_7$ | mp(°C.) | Notes |
|---|---|---|---|---|---|---|---|---|---|---|---|---|---|
| 92 | 2.5 | 20 | 2 | 20 | 1.5 | 4 | thiamorpholino | $CMe_2$ | $CH_2$ | Me | H | 120–122 | (1) |
| 93 | 3.6 | 20 | 3.2 | 20 | 2.4 | 17 | piperidino | $CMe_2$ | $CH_2$ | Me | H | 62–63 | (1) |
| 94 | 4.7 | 10 | 3.9 | 30 | 3 | 6 | 4-methyl-1-piperazinyl | $CMe_2$ | $CH_2$ | Me | H | 280 | (29) |
| 95 | 4.8 | 20 | 4.6 | 40 | 2.8 | 8 | 1-pyrrolidinyl | $CMe_2$ | $CH_2$ | Me | H | 85–86 | (1) |
| 96 | 8 | 80 | 7.2 | 70 | 5.2 | 20 | morpholino | $CMe_2$ | $CH_2$ | Me | 4-Me | 182–183 | (11) |
| 97 | 6 | 10 | 4.2 | 20 | 7.4 | 4 | piperidino | $CH_2$ | $CH_2$ | Me | H | 65–66 | (1)(4)(30) |
| 98 | 3.5 | 20 | 2.8 | 20 | 2.4 | 5 | piperidino | CHMe | $CH_2$ | Me | H | 75–76 | (1)(4)(30) |
| 99 | 7.1 | 40 | 6.8 | 40 | 5.5 | 18 | morpholino | $CH_2$ | $CMe_2$ | H | H | 130–131 | (1) |
| 100 | 7.1 | 50 | 6.1 | 25 | 4.4 | 4 | morpholino | $CH_2$ | $CMe_2$ | Me | H | 63–64 | (1) |
| 101 | 4.4 | 10 | 3.1 | 20 | 2.4 | 20 | $N(CH_2CH_2OMe)_2$ | $CMe_2$ | $CH_2$ | Me | H | 178 | (31) |

EXAMPLE 102

A mixture of 4-(2-aminophenyl)morpholine (5.3 g), acetonitrile (4.52 ml) and anhydrous aluminium chloride (12 g) was heated at 160°–170° C. for 4 hours to yield N-(2-morpholinophenyl)acetamidine (m.p. 140°–141° C.) which was recrystallised from hexane.

EXAMPLE 103

A mixture of 4-(2-amino-4-methylphenyl)morpholine (5.76 g), acetonitrile (3.5 g) and anhydrous aluminium chloride (12 g) was heated at 160°–170° C. for 5 hours to yield N-(5-methyl-2-morpholinophenyl)acetamidine (m.p. 121° C.) which was recrystallised from hexane.

EXAMPLE 104

A mixture of 4-(2-aminophenyl)morpholine (5.34 g), propionitrile (4.7 g) and anhydrous aluminium chloride (12 g) was heated at 160°–170° C. for six hours to yield N-(2-morpholinophenyl)propionamidine (m.p. 114° C.) which was recrystallised from hexane.

EXAMPLE 105

A mixture of 4-(2-aminophenyl)morpholine hydrochloride (7.5 g) and n-butyronitrile (20 ml) was heated at 170° C. in a sealed stainless steel pressure vessel for 60 hours. Excess n-butyronitrile was removed and the residue dissolved in water, basified with 10% aqueous sodium hydroxide solution to pH 12 and extracted with dichloromethane. The extract was washed with water and then brine, dried and the solvent removed. The residue was purified by chromatography on a neutral alumina column. Elution with a 1:1 mixture of dichloromethane and hexane removed unreacted starting material and then elution with a 1:99 mixture of methanol and dichloromethane yielded a solid which was dissolved in methanol (10 ml) and treated with fumaric acid (0.4 g) to give N-(2-morpholinophenyl)butyramidine monofumarate (m.p. 168°–170° C.) which was recrystallised from a 1:2 mixture of methanol and ether.

extracted with ether and the extract washed with water and brine and dried. Removal of the solvent gave a residue which was crystallised from a 1:1 mixture of ethylacetate and hexane to give N-(2-morpholinophenyl)butyramidine (m.p. 131°) which was converted into its monofumarate salt (m.p. 173° C.) which was recrystallised from propan-2-ol.

EXAMPLE 107

A mixture of 4-(2-aminophenyl)morpholine hydrochloride (10 g) and isobutyronitrile (60 ml) was heated at 165° C. for 26 hours in a sealed stainless steel pressure vessel to yield N-(2-morpholinophenyl)isobutyramidine (m.p. 140°–141° C.) which was recrystallised from hexane.

EXAMPLE 108

A mixture of 4-(2-aminophenyl)morpholine (5.34 g), isobutyronitrile (6 g) and anhydrous aluminium chloride (12 g) was heated at 160°–170° C. for 6 hours to give N-(2-morpholinophenyl)isobutyramidine (m.p. 138° C.) which was recrystallised from a 1:1 mixture of ethylacetate and hexane.

EXAMPLE 109

A mixture of 5-methylthio-2-morpholinoaniline (1.8 g), isobutyronitrile (1.66 g) and anhydrous aluminium chloride (3.2 g) was heated at 140° C. for 2 hours to give N-(5-methylthio-2-morpholinophenyl) isobutyramidine (m.p. 155° C.) which was recrystallised from hexane.

EXAMPLE 110

A mixture of 5-fluoro-2-morpholinoaniline (1.96 g) isobutyronitrile (2 g) and anhydrous aluminium chloride was heated at 150° C. for four hours to give N-(5-fluoro-2-morpholinophenyl) isobutyramidine (m.p. 142° C.) which was recrystallised from hexane and converted into its fumarate salt (m.p. 172° C.) which was recrystallised from a 1:1 mixture of methanol and ether.

EXAMPLE 111

A mixture of 4-(2-aminophenyl)morpholine hydrochloride (6.5 g) and valeronitrile (35 ml) were heated at 160°–165° C. under nitrogen for 25 hours and then cooled. The mixture was treated with aqueous sodium hydroxide and the basified mixture was extracted with dichloromethane. The solvent was removed by evaporation and the residue distilled under a pressure of 50 mm Hg to remove half the unreacted valeronitrile. A solid separated on cooling which was separated by filtration, washed with hexane (50 ml) and recrystallised from hexane to give N-(2-morpholinophenyl)valeramidine. (m.p. 135°–136° C.).

EXAMPLE 112

A mixture of 4-(2-aminophenyl)morpholine (3.56 g), pivalonitrile (5 g) and anhydrous aluminium chloride (8 g) was heated at 160°–170° C. for six hours to yield N-(2-morpholinophenyl)pivalamidine (m.p. 126° C.) which was recrystallised from hexane and converted into its monofumarate salt (m.p. 211° C.) which was recrystallised from methanol.

EXAMPLES 113–125

In a similar manner to that described in Example 2, the compounds prepared in the Examples listed below were converted into their fumarate salts which were recrystallised from the solvents given below:

| Ex. | Starting Example | Recrystallisation solvent | mp of fumarate salt (°C.) |
|---|---|---|---|
| 113 | 20 | methanol | 212 |
| 114 | 22 | methanol | 229–230 |
| 115 | 32 | methanol | 213 |
| 116 | 34 | methanol | 180(dec) |
| 117 | 64 | methanol | 197(dec) |
| 118 | 72 | methanol | 188 |
| 119 | 73 | methanol:ether(1:2) | 208–210 |
| 120 | 99 | methanol:ether(1:2) | 204–205 |
| 121 | 100 | methanol | 117–118 |
| 122 | 74 | methanol:ether(1:2) | 179–180 |
| 123 | 102 | methanol:ether(1:1) | 189 |
| 124 | 107 | methanol:ether(1:1) | 162–163 |
| 125 | 111 | isopropanol | 156–158 |

EXAMPLE 126

The product of Example 1 (2.6 g) was reacted at room temperature with excess acrylonitrile (5 ml). The product was recrystallised from ethylacetate to give 4-{2-[1-(2-cyanoethyl)-2-piperidinylideneamino]-phenyl}morpholine. (m.p. 148° C.).

EXAMPLE 127

A mixture of 3-morpholinone (4 g) in dry acetonitrile (40 ml), 4-(2-aminophenyl)morpholine (3.6 g) in dry acetonitrile (20 ml) and phosphorous oxychloride (3.6 ml) was heated for 40 hours at 65°–70° C. to give oil which was purified by column chromatography on neutral alumina (72 g) using (a) hexane, (b) dichloromethane:hexane (1:1) and (c) dichloromethane as eluant. The resulting oil was treated with a saturated solution of hydrogen chloride in methanol (25 ml) to give a pale yellow solid which was recrystallised from a 1:1 mixture of methanol and ether to give 4-[2-(3-morpholinylideneamino)phenyl]-morpholine hydrochloride (m.p. 262°–263° C.).

EXAMPLE 128

A mixture of 2-piperidone (3.6 g) in benzene (30 ml), 4-(2-aminobenzyl)morpholine (5.7 g) in benzene (20 ml) and phosphorus oxychloride (3.6 ml) was heated at 65°–70° C. for 48 hours to yield 4-[2-(2-piperidinylideneamino)benzyl]morpholine (m.p. 108°–110° C.) which was recrystallised from hexane.

EXAMPLE 129

A mixture of 2-piperidone (6 g) in benzene (50 ml), 4-(2-amino-4-chlorobenzyl)morpholine (6.8 g) in benzene (50 ml) and phosphorus oxychloride (5.5 ml) was heated at 60°–65° C. for 5 hours to give 4-[4-chloro-2-(2-piperidinylideneamino)benzyl]morpholine (m.p. 121°–122° C.) which was recrystallised from hexane.

EXAMPLE 130

A mixture of 1-methyl-2-pyrrolidone (4.8 g) in benzene (20 ml), 4-(2-aminobenzyl)morpholine (7.6 g) in benzene (50 ml) and phosphorus oxychloride (4.8 ml) was heated at 65°–70° C. for 18 hours to yield an oil which was dissolved in methanol (30 ml). Treatment with 57% hydroiodic acid (10.1 ml) gave 4-[2-(1-methyl-2-pyrrolidinylideneamino)benzyl]morpholine dihydroiodide (m.p. 230°–232° C.) which was recrystallised from ethanol.

EXAMPLE 131

A mixture of 1,3,3-trimethyl-2-pyrrolidinone (3 g) in benzene (20 ml), 4-(2-aminobenzyl)morpholine (3.8 g) in benzene (10 ml) and phosphorus oxychloride (2.1 ml) was allowed to stand at room temperature for 28 hours and then heated at 60°–65° C. for 14 hours to yield an oil (2.9 g) which was dissolved in methanol (15 ml). Treatment with 57% hydroiodic acid (2.8 ml) gave 4-[2-(1,3,3-trimethyl-2-pyrrolidinylideneamino)benzyl]morpholine dihydroiodide (m.p. 256°–258° C.) which was recrystallised from a 1:1 mixture of ethanol and ether.

EXAMPLE 132

A mixture of N-methylpivalamide (6.2 g) in benzene (50 ml), 4-(2-aminobenzyl)morpholine (9 g) in benzene (40 ml) and phosphorus oxychloride (5 ml) was heated at 80°–85° C. for 12 hours to yield a solid which was dissolved in methanol (25 ml) and treated with fumaric acid (1.4 g) to give N-methyl-N'-(2-morpholinomethylphenyl)pivalamidine monofumarate (m.p. 167°–168° C.) which was recrystallised from propan-2-ol.

EXAMPLE 133

A mixture of 1,3-dimethyl-2-imidazolidinone (7 g) in benzene (45 ml), phosphorus oxychloride (6 ml) and 4-(2-aminophenyl)morpholine (8.5 g) in benzene (30 ml) was heated for 30 hours at 65°–70° C. The product was recrystallised from hexane to give 4-[2-(1,3-dimethyl-2-imidazolidinylideneamino)phenyl]morpholine (m.p. 133°–134° C.).

EXAMPLES 134 to 154

In a similar manner to that described in Example 133 the compounds listed in Table VI were prepared by the reaction of an aminophenyl compound of formula VII (A grammes in B ml benzene) with a compound of formula VIII (C grammes in D ml benzene) in the presence of phosphorus oxychloride (E ml) for F hours at a temperature in the range 65°–70° C.

Notes to Table VI

(32) Product recrystallised from hexane.
(33) Coupling reaction performed at 90°-95° C.
(34) Coupling reaction performed at 70°-75° C.
(35) Coupling reaction performed at 60°-65° C.
(36) The product was isolated as its fumarate salt which was recrystallised from a 2:1 mixture of isopropanol and ether.
(37) Coupling reaction performed at 75°-80° C.
(38) The product was isolated as its monofumarate salt which was recrystallised from a 1:2 mixture of methanol and ether.
(39) The product was isolated as its monofumarate salt which was recrystallised from a 1:3 mixture of methanol and ether.
(40) Coupling reaction performed at 80°-85° C.
(41) The product was purified by column chromatography on an alumina column using dichloromethane as eluant.
(42) coupling reaction performed at 80°-85° C. for 48 hours and at 90°-95° C. for 14 hours. The product was purified by column chromatography on an alumina column using a 99:1 mixture of dichloromethane and methanol as eluant.
(43) The product was isolated as its sesquifumarate salt which which was recrystallised from a 1:2 mixture of methanol and ether.

A mixture of 1-(2-hydroxyethyl)-2-imidazolidinone (2.28 g), benzoic anhydride (4.5 g), triethylamine (2.4 g), 4-dimethylaminopyridine (0.1 g) and 1,2-dimethoxyethane (20 ml) was stirred at room temperature for 8 hours. Saturated sodium bicarbonate solution (15 ml) was added and the mixture extracted with dichloromethane (100 ml). The extract was washed with water, brine and then dried and filtered. The solvent was removed to give 1-(2-benzoyloxyethyl)-2-imidazolidinone (m.p. 130°-132° C.) which was recrystallised from ethylacetate.

A mixture of 1-(2-benzoyloxyethyl)-2-imidazolidinone (2.3 g) and methyl-4-toluenesulphonate (2 g) was heated at 90°-95° C. for 48 hours. The reaction mixture was then cooled to room temperature, treated with saturated sodium bicarbonate solution (10 ml) and extracted with ethyl acetate (6×20 ml). The extract was washed with water and brine and then dried and filtered. The solvent was removed to give an oily residue (2 g) which was purified by column chromatography on silica gel (80 g, 100-200 mesh) using a 1:1 mixture of ethylacetate and hexane as eluant to give 1-(2-benzoyloxyethyl)-3-methyl-2-imidazolidinone as an oil.

In a similar manner to that described in Example 133, 1-(2-benzoyloxyethyl)-3-methyl-2-imidazolidone (8.8 g) in benzene (30 ml) was reacted with 4-(2-aminophenyl)-morpholine (5.2 g) in benzene (20 ml) in the presence of phosphorus oxychloride (3.3 ml) for 35 hours at 80°-85°

TABLE VI

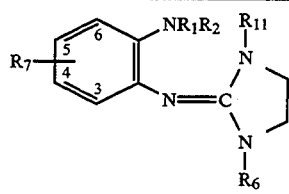

| Ex. | A | B | C | D | E | F | $NR_1R_2$ | $R_6$ | $R_{11}$ | $R_7$ | mp(°C.) | Notes |
|---|---|---|---|---|---|---|---|---|---|---|---|---|
| 134 | 3.8 | 25 | 2.7 | 40 | 2.1 | 21 | morpholino | Me | Me | 4-F | 115-117 | (32) |
| 135 | 9.8 | 25 | 12.6 | 10 | 7.3 | 50 | morpholino | Me | Me | 3-Me | 85-86 | (32) |
| 136 | 2.9 | 30 | 2.6 | 30 | 2.1 | 23 | morpholino | Me | Me | 4-Me | 105-106 | (32)(33) |
| 137 | 5 | 25 | 4.2 | 35 | 3.7 | 35 | morpholino | Me | Me | 5-Me | 109-110 | (32)(34) |
| 138 | 8.5 | 40 | 9.1 | 60 | 7.3 | 18 | morpholino | Me | Me | 4-Cl | 103-104 | (32) |
| 139 | 4 | 40 | 2.7 | 30 | 2.2 | 23 | morpholino | Me | Me | 4-OMe | 79-80 | (32) |
| 140 | 3.5 | 30 | 2.5 | 30 | 2.3 | 6 | morpholino | Me | Me | 4,5-(OMe)$_2$ | 117-118 | (32)(35) |
| 141 | 3.2 | 20 | 2.7 | 30 | 2.2 | 28 | 1-pyrrolidinyl | Me | Me | H | 162-163 | (36) |
| 142 | 5.2 | 30 | 5.1 | 30 | 4.1 | 70 | 1-pyrrolidinyl | Me | Me | 3-Me | 75-76 | (32) |
| 143 | 8.8 | 60 | 8.5 | 50 | 6.8 | 10 | piperidino | Me | Me | H | 61 | (32) |
| 144 | 5.8 | 50 | 5.1 | 60 | 4 | 26 | thiamorpholino | Me | Me | H | 96-98 | (32) |
| 145 | 8.2 | 80 | 6.8 | 40 | 5.4 | 14 | 2,6-dimethyl-morpholino | Me | Me | H | 86-86 | (32)(37) |
| 146 | 6.3 | 30 | 6.8 | 40 | 5.4 | 28 | NEt$_2$ | Me | Me | H | 164-165 | (38)(37) |
| 147 | 3.6 | 60 | 3.4 | 40 | 2.7 | 90 | 2-methyl-1-pyrrolidinyl | Me | Me | H | 183-184 | (39)(40) |
| 148 | 5.3 | 25 | 4.3 | 25 | 3.4 | 80 | morpholino | Me | Me | 3-Cl | 86-88 | (32)(33)(41) |
| 149 | 4.8 | 40 | 5.1 | 40 | 4.8 | 24 | 1-pyrrolidinyl | Me | Me | 4-Me | 165-167 | (38)(40) |
| 150 | 8.9 | 50 | 6.8 | 50 | 5.4 | 12 | N(CH$_2$CH$_2$OMe)$_2$ | Me | Me | H | 105-106 | (38)(37) |
| 151 | 5.2 | 40 | 6.4 | 30 | 4.3 | 48 | morpholino | Et | Et | H | 154-155 | (42)(38) |
| 152 | 7.6 | 30 | 6.8 | 30 | 5.5 | 14 | morpholino | Me | Me | 6-Me | 106-108 | (40)(32) |
| 153 | 7.1 | 60 | 7.6 | 80 | 5.6 | 70 | morpholino | Et | Et | H | 75-76 | (40)(32) |
| 154 | 4.4 | 20 | 5.9 | 50 | 4.4 | 60 | morpholino | Bu | Me | H | 135-136 | (40)(41)(43) |

EXAMPLE 155

A mixture of N-(2-hydroxyethyl)ethylenediamine (31.2 g), urea (23.4 g) and water (3 ml) was heated at 130° C. for 3 hours and at 210° C. for 8 hours and then distilled directly from the reaction mixture to give 1-(2-hydroxyethyl)-2-imidazolidinone (30 g) as an oil [(b.p. 150°-160° C. (0.2 mm)] which solidified to give a solid (m.p. 50-51).

C. to yield an oil. The oil was dissolved in methanol (10 ml) and treated with fumaric acid (1.8 g). The solvent was removed by evaporation and the residue washed with ether and then dissolved in water. The aqueous solution was basified with aqueous sodium carbonate solution to pH 9-10 and extracted with ether to yield an oil which was purified by chromatography on an alumina column using dichloromethane as eluant. The purified base (0.8 g) in methanol (10 ml) was treated with fumaric acid (0.23 g) to give 4-{2-[1-(2-benzoyloxyethyl)-3-methyl-2-imidazolidinylideneamino]phenyl}morpholine monofumarate (m.p. 132°–133° C.) which was recrystallised from a 1:2 mixture of methanol and ether.

EXAMPLE 156

Reaction of tetramethylurea (10.4 g, 10.7 ml) in dry benzene (80 ml) with 4-(2-aminophenyl)morpholine (10.2 g) in dry benzene (100 ml) in the presence of phosphorus oxychloride (8.3 ml) for 30 hours at 65°–70° C. gave an oil which was purified by column chromotography on a neutral alumina column (100 g) eluted with hexane to give as an oil. A solution of this base (2.5 g) in methanol (10 ml) was treated with 57% hydroiodic acid (1.3 ml) to give 2-(2-morpholinophenyl)-1,1,3,3-tetramethylguanidine hydroiodide as a pale yellow crystalline solid (m.p. 215°–216° C.) which was recrystallised from a 2:3 mixture of methanol and ether.

EXAMPLE 157

Reaction of 3-ethyl-1,1,3-trimethylurea (6.57 g) in benzene (70 ml) with 4-(2-aminophenyl)morpholine (6 g) in benzene (30 ml) in the presence of phosphorus oxychloride (4.71 ml) for 45 hours at 65°–70° C. gave 1-ethyl-2-(2-morpholinophenyl)-1,3,3-trimethylguanidine (bp. 140° C. at 0.2 mm Hg).

EXAMPLE 158

Reaction of 3-allyl-1,1,3-trimethylurea (7.17 g) in benzene (50 ml) with 4-(2-aminophenyl)morpholine (6 g) in benzene (30 ml) in the presence of phosphorus oxychloride (4.71 ml) for 45 hours at 70° C. gave 1-allyl-2-(2-morpholinophenyl)-1,3,3-trimethylguanidine (bp. 148°–150° C. at 0.2 mm Hg).

EXAMPLE 159

Reaction of 3-n-butyl-1,1,3-trimethylurea (7 g) in benzene (60 ml) with 4-(2-aminophenyl)morpholine (7.2 g) in benzene (30 ml) in the presence of phosphorus oxychloride (4 ml) for 18 hours at 80°–85° C. gave 1-n-butyl-2-(2-morpholinophenyl)-1,3,3-trimethyl guanidine (bp. 162°–163° C. at 0.7 mm Hg).

EXAMPLE 160

Reaction of 3-pentyl-1,1,3-trimethylurea (7.5 g) in benzene (80 ml) with 4-(2-aminophenyl)morpholine (6.46 g) in benzene (30 ml) in the presence of phosphorus oxychloride (4.06 ml) for 45 hours at 70° C. gave 1-pentyl-2-(2-morpholinophenyl)-1,3,3-trimethyl guanidine (b.p. 98° C. at 1.5 mm Hg).

EXAMPLE 161

Reaction of 1-(2-hydroxyethyl)-2-imidazolidinone (13 g) in dry dimethylformamide (125 ml) with sodium hydride (50% suspension in paraffin oil 12 g) at 10° C. for 3 hours was followed by treatment with methyl iodide (35.5 g) over a period of one hour. The mixture was stirred at ambient temperature for 18 hours gave 1-methyl-3-(2-methoxyethyl)-2-imidazolidinone (b.p. 110°–114° C. at 0.4 mm).

Reaction of 1-methyl-3-(2-methoxyethyl)-2-imidazolidinone (11.4 g) in benzene (60 ml) with 4-(2-aminophenyl)morpholine (8.9 g) in benzene (80 ml) in the presence of phosphorus oxychloride (7.2 ml) for 30 hours at 80°–85° C. gave an oil a portion of which (1.8 g) was dissolved in methanol (10 ml) and treated with fumaric acid (0.9 g) to give 4-{2-[1-methyl-3-(2-methoxyethyl)-2-imidazolidinylideneamino]phenyl}morpholine monofumarate (m.p. 127°–129° C.) which was recrystallised from propan-2-ol.

EXAMPLE 162

Reaction of 1-methyl-3-(2-hydroxyethyl)-2-imidazolidinone (13 g) with acetic anhydride (9.2 g) in dichloromethane (60 ml) in the presence of triethylamine (9 g) and 4-dimethylaminopyridine (0.1 g) for 18 hours at ambient temperature gave 1-methyl-3-(2-acetoxyethyl)-2-imidazolidinone as an oil.

Reaction of 1-methyl-3-(2-acetoxyethyl)-2-imidazolidinone (13.4 g) in benzene (80 ml) with 4-(2-aminophenyl)morpholine (10.6 g) in benzene (80 ml) in the presence of phosphorus oxychloride (7 ml) for 30 hours at 80°–85° C. gave 4-{2-[1-methyl-3-(2-acetoxyethyl)-2-imidazolidinylideneamino]phenyl}morpholine.

Reaction of 4-{2-[1-methyl-3-(2-acetoxyethyl)-2-imidazolidinylideneamino]phenyl}morpholine (2.7 g) in dimethylformamide (10 ml) with sodium hydroxide (0.4 g) in water (10 ml) for one hour at 10° C. gave an oil which was dissolved in methanol (10 ml) and treated with fumaric acid (0.4 g) to give 4-{2-[1-methyl-3-(2-hydroxyethyl)-2-imidazolidinylideneamino]phenyl}morpholine (m.p. 129°–131° C.) which was recrystallised from a 1:2 mixture of methanol and ether.

EXAMPLE 163

Reaction of 4-dimethylcarbamoylmorpholine (3.8 g) in benzene (25 ml) with 4-(2-aminophenyl)morpholine (3.5 g) in the presence of phosphorus oxychloride (2.1 ml) for 40 hours at 80°–85° C. gave N,N-dimethyl-N'-(2-morpholinophenyl)morpholine-4-carboxamidine (m.p. 126°–128° C.) which was recrystallised from hexane.

EXAMPLE 164

Reaction of 1-dimethylcarbamoylpiperidine (3.7 g) in benzene (25 ml) with 4-(2-morpholinophenyl)morpholine (3.5 g) in the presence of phosphorus oxychloride for 35 hours at 80°–85° C. gave N,N-dimethyl-N'-(2-morpholinophenyl)piperidine-1-carboxamidine (m.p. 88°–90° C.) which was recrystallised from petroleum ether (b.p. 40°–60° C.)

EXAMPLE 165

Reaction of 4-[2-(1,3-dimethyl-2-imidazolidinylideneamino)phenyl]thiamorpholine (1.5 g prepared as described in Example 144) in methanol (20 ml) and sodium metaperiodate (1.4 g) in water (4 ml) for 4 hours at 10° C. yielded 4-[2-(1,3-dimethyl-2-imidazolidinylideneamino)phenyl]thiamorpholine-1-oxide monohydrate (m.p. 103°–105° C.) which was recrystallised from a 1:1 mixture of 1,2-dimethoxyethane and hexane.

EXAMPLE 166

A solution of 2-morpholinophenyl isothiocyanate (2.3 g) was treated with a saturated solution of ammonia in ethanol (20 ml) and the reaction mixture was stirred at room temperature for 3 hours. The resulting solid was filtered, washed with ethanol and dried to give 1-[2-(4-morpholino)phenyl]thiourea (m.p. 194°–195° C.).

A solution of 1-(2-morpholinophenyl)thiourea (7.2 g) in dry methanol (30 ml) was heated at reflux with methyliodide (4.2 g) for 2 hours. The solvent was removed under reduced pressure and dry ether (15 ml) was added and on scratching gave 2-methyl-1-(2-morpholinophenyl)-2-thiopseudourea hydroiodide (m.p. 151°–152° C.).

A mixture of 2-methyl-1-(2-morpholinophenyl)-2-thiopseudourea hydroiodide (5 g) and ethylenediamine (2.4 g), in dry ethanol (50 ml) was heated at reflux for 6 hours, the solvent removed under reduced pressure to give an oil which was dissolved in dichloromethane (50 ml), cooled, basified with 20% sodium hydroxide and the organic layer was washed successively with water, brine and dried (Na$_2$SO$_4$), filtered and the solvent removed to get a solid (4 g) which on recrystallisation from ethyl acetate gave 4-[2-(2-imidazolidinylideneamino)phenyl]morpholine (m.p. 185°–186° C.).

EXAMPLE 167

A mixture of 2-methyl-1-(2-morpholinophenyl)-2-thiopseudourea hydroiodide (3 g prepared as described in Example 166), N-methylethylenediamine (2 ml) and absolute ethanol (35 ml) was heated under reflux for 8 hours to give a solid which was recrystallised from ethyl acetate to give 4-[2-(1-methyl-2-imidazolidinylideneamino)phenyl]morpholine (m.p. 156° C.).

EXAMPLES 168 to 202

In a similar manner to that described in Example 167, the compounds listed in Table VII were prepared by heating a mixture of a compound of formula XIII in which R$_{14}$ and R$_{15}$ are H, (G grammes), an N-substituted ethylenediamine of formula H$_2$N(CH$_2$)$_2$NHR$_6$ (H grammes) in dry ethanol (I ml) under reflux for J hours.

Note to Table VII

Notes (32), (38), (39) and (41) has the meaning given with respect to earlier Tables.

(44) Product recrystallised from ethylacetate.

(45) Product isolated as its monofumarate salt which was recrystallised from methanol.

(46) The preparation of the compound of formula XIV is given hereinafter as Preparative Procedure A.

(47) Product isolated as its fumarate salt which was recrystallised from a 1:2 mixture of methanol and propan-2-ol.

(48) Product recrystallised from a 1:4 mixture of 1,2-dimethoxyethane and petroleum ether (b.p. 40°–60° C.).

(49) The preparation of the compound of formula XIV is given hereinafter as Preparative Procedure B.

(50) The preparation of the compound of formula XIV is given hereinafter as Preparative Procedure C.

(51) The preparation of the compound of formula XIV is given hereinafter as Preparative Procedure D.

(52) Product recrystallised from a 1:2 mixture of ethylacetate and hexane.

(53) The preparation of the compound of formula XIV is given hereinafter as Preparative Procedure E.

(54) The preparation of the compound of formula XIV is given hereinafter as Preparative Procedure F.

(55) The preparation of the compound of formula XIV is given hereinafter as Preparative Procedure G.

(56) Product was purified by chromatography on an alumina column using the following eluents sequentially:—hexane, a 1:1 mixture of dichloromethane and hexane and then dichloromethane.

(57) The preparation of the compound of formula XIV is given hereinafter as Preparative Procedure H.

(58) Product recrystallised from a 1:1 mixture of ethylacetate and hexane.

TABLE VII

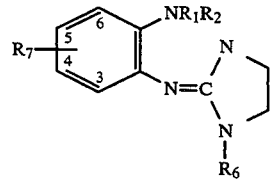

| Ex. | G | H | I | J | NR$_1$R$_2$ | R$_6$ | R$_7$ | mp(°C.) | Notes |
|---|---|---|---|---|---|---|---|---|---|
| 168 | 3.8 | 2.7 | 45 | 8 | morpholino | Et | H | 107–109 | (32) |
| 169 | 2.8 | 2.6 | 35 | 10 | morpholino | Pr | H | 131–132 | (32) |
| 170 | 3.8 | 3 | 45 | 14 | morpholino | i-Pr | H | 121–122 | (32) |
| 171 | 5.7 | 5.2 | 65 | 7 | morpholino | Bu | H | 88–89 | (32) |
| 172 | 3.8 | 3.5 | 45 | 12 | morpholino | i-Bu | H | 136–138 | (32) |
| 173 | 7.5 | 7.8 | 90 | 14 | morpholino | pentyl | H | 72–74 | (32) |
| 174 | 3.8 | 3 | 50 | 8 | morpholino | allyl | H | 126–128 | (32) |
| 175 | 3.8 | 3.1 | 45 | 25 | morpholino | CH$_2$CH$_2$OH | H | 131–132 | (44) |
| 176 | 7.9 | 6.2 | 90 | 150 | morpholino | CH$_2$CH$_2$OH | 3-Me | 198–199 | (45)(46) |
| 177 | 3.8 | 3.8 | 45 | 9 | morpholino | CH$_2$CH$_2$OMe | H | 74–75 | (32) |
| 178 | 3.8 | 4.2 | 40 | 24 | morpholino | cyclohexyl | H | 189–189 | (44) |
| 179 | 5.7 | 6.75 | 70 | 12 | morpholino | CH$_2$Ph | H | 96–97 | (32) |
| 180 | 7.6 | 9.8 | 90 | 8 | morpholino | CH$_2$CH$_2$Ph | H | 106–108 | (32) |
| 181 | 11.4 | 8.3 | 150 | 24 | morpholino | CH$_2$CH$_2$NMe$_2$ | H | 151 | (47) |
| 182 | 5.7 | 6 | 70 | 24 | morpholino | CH$_2$CHOHCH$_2$OH | H | 144–145 | (44) |
| 183 | 3.8 | 3.4 | 45 | 18 | morpholino | CH$_2$C(Me)=CH$_2$ | H | 141–143 | (48) |
| 184 | 4.2 | 2.4 | 45 | 8 | N(CH$_2$CH$_2$OMe)$_2$ | Me | H | 140–141 | (39)(49) |
| 185 | 3.0 | 2.2 | 30 | 40 | N(CH$_2$CH$_2$OMe)$_2$ | CH$_2$CH$_2$OH | H | 110–111 | (38)(49) |
| 186 | 7.9 | 4.4 | 90 | 8 | thiamorpholino | Me | H | 115–117 | (32)(50) |
| 187 | 5.4 | 3.3 | 70 | 10 | 1-pyrrolidinyl | Me | H | 117–118 | (32)(51) |
| 188 | 3.9 | 3.5 | 45 | 8 | thiamorpholino | Bu | H | 106–108 | (32)(50) |
| 189 | 7.8 | 4.4 | 90 | 75 | morpholino | Me | 3-Me | 120–121 | (52)(46) |
| 190 | 9.8 | 5.9 | 115 | 12 | morpholino | Me | 4-Me | 122–123 | (32)(53) |
| 191 | 7.2 | 6.4 | 90 | 24 | 1-pyrrolidinyl | CH$_2$CH$_2$OH | H | 166–167 | (38)(51) |
| 192 | 3.7 | 3.1 | 45 | 32 | 2-methyl-1-pyrrolidinyl | CH$_2$CH$_2$OH | H | 81 | (32)(54) |

TABLE VII-continued

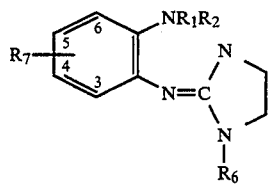

| Ex. | G | H | I | J | NR₁R₂ | R₆ | R₇ | mp(°C.) | Notes |
|---|---|---|---|---|---|---|---|---|---|
| 193 | 5.9 | 5.2 | 75 | 12 | morpholino | Bu | 4-Me | 114-116 | (32) |
| 194 | 7.5 | 3.6 | 150 | 24 | piperidino | H | H | 163 | (38)(55) |
| 195 | 7.5 | 5.5 | 90 | 14 | piperidino | Me | H | 75-76 | (41)(32)(55) |
| 196 | 5.9 | 3.4 | 70 | 70 | piperidino | Me | 3-Me | 86-87 | (56)(32)(57) |
| 197 | 2.8 | 2.2 | 40 | 24 | thiamorpholino | CH₂CH₂OH | H | 99-101 | (58)(50) |
| 198 | 3.7 | 3.1 | 45 | 18 | piperidino | CH₂CH₂OH | H | 105-107 | (32)(55) |
| 199 | 5.6 | 5.3 | 65 | 39 | morpholino | (CH₂)₃OH | H | 139-140 | (44) |
| 200 | 5.9 | 3.4 | 70 | 70 | morpholino | CH₂CH(OH)Me | H | 147-148 | (44) |
| 201 | 7.6 | 8 | 90 | 23 | morpholino | CH₂CH(OH)Et | H | 112-113 | (56) |
| 202 | 3.8 | 3.9 | 45 | 14 | morpholino | CH₂C(OH)Me₂ | H | 132-133 | (44) |

Preparative Procedure A

Reaction of 6-methyl-2-morpholinoaniline (9.6 g) in dioxan (25 ml) and water (100 ml) with thiophosgene (5.7 ml) at 0° C. for 30 minutes and at room temperature for 3 hours gave 6-methyl-2-morpholinophenyl isothiocyanate as an oil.

Reaction of 6-methyl-2-morpholinophenyl isothiocyanate (8.8 g) with 33% alcoholic ammonia solution (60 ml) at room temperature for 5 hours gave 1-(6-methyl-2-morpholinophenyl)thiourea (9 g) as a pale yellow solid, m.p. 199° C. which was recrystallised from a 1:1 mixture of ethylacetate and hexane.

A mixture of 1-(6-methyl-2-morpholinophenyl)thiourea (9 g) and methyl iodide (2.5 ml) in dry acetone (100 ml) was heated at reflux at 90°-95° C. for 2.5 hours to give 2-methyl-1-(6-methyl-2-morpholinophenyl)-2-thiopseudourea hydroiodide.

Preparative Procedure B

A solution of N,N-bis(2-methoxyethyl)benzene-1,2-diamine (7.5 g) in dioxane (10 ml) was added to a mixture of thiophosgene (4 ml) and water (60 ml) which had been cooled to 0° C. The temperature of the mixture was allowed to rise to ambient and the mixture was stirred for 4 hours. Ice water (50 ml) was added and the mixture extracted with ether (3×20 ml). The extract was washed with water (50 ml) and brine (50 ml), dried and evaporated to give a residue which was heated at 45° C. under vacuum (100 mm/Hg) to give 2-[bis(2-methoxyethyl)amino]phenyl isothiocyanate as an oil.

A saturated solution of ammonia in ethanol (40 ml) was added over 40 minutes to a mixture of 2-[bis(2-methoxyethyl)amino]phenyl isothiocyanate (7.5 g) and ethanol (10 ml) which had been cooled to 10° C. The mixture was stirred at 0° C. for 8 hours and then stirred without cooling for 16 hours. The solvent was then removed by evaporation and the residue purified by chromatography on a silica column eluted with a 1:4 mixture of ethyl acetate and hexane and then a 1:1 mixture of ethyl acetate and hexane to give 1-{2-[bis(2-methoxyethyl)amino]phenyl}thiourea (m.p. 118°-119° C.).

A mixture of 1-{2-[bis(2-methoxyethyl)amino]phenyl}thiourea (5 g), methyl iodide (1.4 ml) and acetone (25 ml) was heated at 40° C. for 2 hours. Removal of the solvent gave a residue which was triturated with ether to give 2-methyl-1-{2-[bis(2-methoxyethyl)amino]phenyl}-2-thiopseudourea hydroiodide (m.p. 111°-112° C.).

Preparative Procedure C

A solution of 2-thiamorpholinoaniline (14.6 g) in dioxane (10 ml) was added over 15 minutes to a mixture of thiophosgene (8.77 ml) and water (120 ml) which had been cooled to 0° C. The mixture was stirred and its temperature was allowed to rise to ambient. The mixture was then stirred for 4 hours and ice/water (200 ml) was added. The mixture was extracted with ether (2×100 ml) and the extracts washed with water (50 ml) and then brine (100 ml) and the solvent removed by evaporation to give a residue which was heated at 40°-45° C. under vacuum (100 mm/hg) for two hours to give 2-thiamorpholinophenyl isothiocyanate (m.p. 55°-56° C.).

25% Aqueous ammonia solution (100 ml) was added to a mixture of 2-thiamorpholinophenyl isothiocyanate (14 g) and ethanol (40 ml) at 10° C. The mixture was stirred at 30° C. for 24 hours and then cooled to 10° C. 1-(2-thiamorpholinophenyl)thiourea was collected by filtration, washed with water (100 ml) and dried (m.p. 170°-171° C.).

A mixture of 1-(2-thiamorpholinophenyl)thiourea (12.6 g), methyl iodide (7.1 g) and acetone (60 ml) was heated at 90°-95° C. for 2½ hours. The solvent was removed by evaporation and the residue dried under vacuum (5 mm/Hg) to give 2-methyl-1-(2-thiamorpholinophenyl)-2-thiopseudourea hydroiodide (m.p. 176°-177° C.).

Preparative Procedure D

Benzoylisothiocyanate (10 ml) was added over 30 minutes to a mixture of 2-(1-pyrrolidinyl)aniline (10.6 g) and dichloromethane (30 ml). The mixture was then stirred at 30° C. for 4 hours. The solvent was removed by evaporation and the residue dried under vacuum (5 mm/Hg) for 30 minutes and triturated with ether. 3-Benzoyl-1-[2-(1-pyrrolidinyl)phenyl]thiourea was collected by filtration, washed with ether and dried (m.p. 172°-173° C.).

A mixture of 3-benzoyl-1-[2-(1-pyrrolidinyl)phenyl]-thiourea (18.1 g), sodium hydroxide (5 g) and water (50 ml) was heated at 90°-95° C. for 4 hours. Ice and then 50% aqueous hydrochloric acid were added. The mixture was filtered and the filtrate treated with saturated sodium bicarbonate solution to pH 8. 1-[2-(1-Pyrrolidinyl)phenyl]thiourea was collected by filtration, washed with water and dried (m.p. 185°–186° C.).

A mixture of 1-[2-(1-pyrrolidinyl)phenyl]thiourea (12.2 g), acetone (100 ml) and methanol (20 ml) was heated to 90°–95° C. Methyl iodide (8.36 g) was added and the mixture heated under reflux for 3 hours. The solvent was removed by evaporation to give a residue which was dried under vacuum (5 mm/Hg) to give 2-methyl-1-[2-(1-pyrrolidinyl)phenyl]-2-thiopseudourea hydroiodide (m.p. 139°–141° C.).

Preparative Procedure E

Reaction of 5-methyl-2-morpholinoaniline (20 g) in dioxan (80 ml) and water (200 ml) at 0° C. for 30 minutes and at room temperature for 2 hours gave 5-methyl-2-morpholinophenyl isothiocyanate, (m.p. 91°–92° C.).

Reaction of 5-methyl-2-morpholinophenyl isothiocyanate (15 g) with 33% ethanolic ammonia solution for 48 hours at room temperature gave 1-(5-methyl-2-morpholinophenyl)thiourea as a pale yellow solid (m.p. 181°–182° C.).

A mixture of 1-(5-methyl-2-morpholinophenyl)thiourea (14 g), methyl iodide (7.9 g) in methanol (50 ml) was heated at reflux for 2 hours to give 2-methyl-1-(5-methyl-2-morpholinophenyl)-2-thiopseudourea hydroiodide as a pale yellow solid, m.p. 157°–159° C.

Preparative Procedure F

A mixture of 2-methyl-1-(2-aminophenyl)pyrrolidine (9.1 g) and benzoyl isothiocyanate (9.2 g) 7.7 ml) and dichloromethane (100 ml) was stirred at room temperature for 8 hours and left overnight. Removal of the solvent and trituration with ether gave 1-benzoyl-3-[2-methyl-1-pyrrolidinyl)phenyl]thiourea, (m.p. 105°–106° C.).

A mixture of 1-benzoyl-3-[2-(2-methyl-1-pyrrolidinyl)phenyl]thiourea (9 g), sodium hydroxide (1 g, as pellets) and water (10 ml) was heated at 90°–95° C. for 48 hours to give 1-[2-(2-methyl-1-pyrrolidinyl)phenyl]thiourea (m.p. 145°–148° C.) which was purified by column chromatography on silica gel using a 1:1 mixture of ethylacetate and hexane as eluant.

A mixture of 1-[2-(2-methyl-1-pyrrolidinyl)phenyl]thiourea (3.4 g) and methyl iodide (2.1 g) in acetone (60 ml) was heated at 90°–95° C. for 3 hours and the solvent removed to give 2-methyl-1-[2-methyl-1-pyrrolidinyl)phenyl]-2-thiopseudourea hydroiodide (3.7 g) as a thick oil.

Preparative Procedure G

A solution of 2-piperidinoaniline (17.6 g) in dioxane (100 ml) was added over 25 minutes to a mixture of thiophosgene (10.2 ml) and water (200 ml) which had been cooled to 0° C. The temperature of the mixture was allowed to rise to ambient and the mixture was stirred for 4 hours. Ice (200 g) and water (200 ml) were added and the mixture extracted with ether (6×50 ml). The combined extracts were washed with water (100 ml) and brine (100 ml), dried and evaporated to give a residue which purified by chromatography on a silica column eluted with hexane to give 2-piperidinophenyl isothiocyanate as an oil.

25% Aqueous ammonia solution (60 ml) was added to a mixture of 2-piperidinophenyl isothiocyanate (12 g) and ethanol (25 ml) which had been cooled to 10° C. The mixture was stirred at 30° C. for 24 hours and then cooled to 10° C. 1-(2-Piperidinophenyl)thiourea was collected by filtration, washed with water and dried (m.p. 143°–145° C.).

A mixture of 1-(2-piperidinophenyl)thiourea (10.1 g), methyl iodide (5.35 g) and methanol (50 ml) was heated at 50°–55° C. for 2 hours. The solvent was removed by evaporation and the residue dried under vacuum (5 mm/Hg) to give 2-methyl-1-(2-piperidinophenyl)-2-thiopseudourea hydroiodide (m.p. 160°–162° C.).

Preparative Procedure H

Reaction of 6-methyl-2-piperidinoaniline (6.4 g) in dioxan (20 ml) and water (65 ml) with thiophosgene (5.7 g) at 0° C. for 30 minutes and at room temperature for 2 hours gave 6-methyl-2-piperidinophenyl isothiocyanate as an oil.

Reaction of 6-methyl-2-piperidinophenyl isothiocyanate (6.8 g) with 25% aqueous ammonia solution (65 ml) in ethanol (20 ml) for 8 hours at room temperature gave 1-(6-methyl-2-piperidinophenyl) thiourea as a pale yellow solid (m.p. 197°–198° C.).

A mixture of 1-(6-methyl-2-piperidinophenyl)thiourea (7 g) and methyl iodide (4.38 g) in dry methanol (100 ml) was heated under reflux for 3 hours to give 2-methyl-1-(6-methyl-2-piperidinophenyl)-2-thiopseudourea hydroiodide as a pale yellow solid, (m.p. 204°–205° C.).

EXAMPLE 203

A mixture of 2-methyl-1-(2-morpholinophenyl)-2-thiopseudourea hydroiodide (3.8 g prepared as described in Example 166), 2-methylethylenediamine (2.2 g) and ethanol (45 ml) was heated under reflux for 8 hours to give a solid which was recrystallised from ethyl acetate to give 4-[2-(4-methyl-2-imidazolidinylideneamino)-phenyl]morpholine (m.p. 173°–174° C.).

EXAMPLE 204

A mixture of 2-methyl-1-(2-morpholinophenyl)-2-thiopseudourea hydroiodide (7.6 g prepared as described in Example 166), 1,2-dimethylethylenediamine (5.3 g) and ethanol (90 ml) was heated under reflux for 70 hours to give a solid which was recrystallised from ethylacetate to give 4-[2-(4,5-dimethyl-2-imidazolidinylideneamino)phenyl]morpholine (m.p. 142°–143° C.).

EXAMPLE 205

Ethylene oxide generated from 2-chloroethanol (36 g) and potassium hydroxide pellets (20 g) in methanol (60 ml) was reacted with 1,2-dimethylethylenediamine (22.6 g) in methanol (50 ml) at −15° C. to give N-(2-hydroxyethyl)-1,2-dimethylethylenediamine as a colourless liquid (b.p. 89°–91° C. at 1 mmHg).

A mixture of 2-methyl-1-(2-morpholinophenyl)-2-thiopseudourea (12.5 g) and N-(2-hydroxyethyl)-1,2-dimethylethylenediamine (8 g) in dry ethanol (150 ml) was heated under reflux at 90°–95° C. for 6 days to give a dark brown oil which was purified by column chromatography on neutral alumina (250 g) using a 1:9 mixture of dichloromethane and hexane to give 4-{2-[4,5-dimethyl-1-(2-hydroxyethyl)-2-imidazolidinylideneamino]phenyl}morpholine as a colourless solid (m.p. 108°–109° C.) which was recrystallised from hexane.

EXAMPLE 206

A mixture of 2-methyl-1-(2-morpholinophenyl)-2-thiopseudourea hydroiodide (3.8 g prepared as described in Example 166), N'-isopropyl-2-methyl-1,2-propanediamine (3.95 g) and ethanol (45 ml) was heated under reflux for 28 hours to yield an oil which was purified by column chromatography on a neutral alumina column using dichloromethane as eluant. The resultant oil (1.5 g) was dissolved in methanol (10 ml) and fumaric acid (0.5 g) was added to give 4-[2-(1-isopropyl-4,4-dimethyl-2-imidazolidinylidenamino)phenyl]-morpholine monofumarate (mp 206°–208° C.) which was recrystallised from a 1:3 mixture of methanol and ether.

EXAMPLE 207

A mixture of 2-methyl-1-(2-morpholinophenyl)-2-thiopseudourea hydroiodide (3.8 g prepared as described in Example 166), 3-methylaminopropylamine (2.6 g) and absolute ethanol (40 ml) was heated under reflux for 6 hours to give a solid which was recrystallised from ether to give 4-[2-(1-methylperhydropyrimidin-2-ylideneamino)phenyl]morpholine (m.p. 138°–139° C.).

EXAMPLE 208

A mixture of 2-methyl-1-(2-morpholinophenyl)-2-thiopseudourea hydroiodide (7.6 g) and 1,4-diaminobutane (5.3 g) in ethanol (150 ml) was heated under reflux for 60 hours to give a white solid (m.p. 135° C.) which was recrystallised from ethyl acetate. The solid (2.7 g) was dissolved in methanol (20 ml) and treated with fumaric acid to give 2-(2-morpholinophenylimino)-1,3-diazocycloheptane fumarate (m.p. 220°–222° C.) which was recrystallised from a 1:1 mixture of methanol and ether.

EXAMPLE 209

A mixture of 2-methyl-1-(2-morpholinophenyl)-2-thiopseudourea hydroiodide (1 g), dimethylamine (1 ml of a 33% solution in ethanol) and ethanol (2 ml) was kept at ambient temperature for 48 days. The mixture was then cooled in an ice bath. The resulting solid was separated by filtration, treated with dilute aqueous sodium hydroxide solution (5 ml) and the resulting mixture extracted with dichloromethane (2×50 ml). The extract was washed with brine, dried and the solvent removed by evaporation to give 1,1-dimethyl-2-(2-morpholinophenyl)guanidine (m.p. 143°–144° C.) which was recrystallised from hexane.

EXAMPLE 210

A solution of 4-(2-aminophenyl)morpholine (5.3 g) in dichloromethane (25 ml) was treated with methyl isothiocyanate (3.2 g) and the mixture stirred at room temperature for 36 hours to yield 1-(2-morpholinophenyl)-3-methylthiourea (m.p. 115°–116° C.) which was recrystallised from a 4:1 mixture of ethyl acetate and hexane.

A mixture of 1-(2-morpholinophenyl)-3-methylthiourea (5 g) and methyliodide (2.8 g) in acetone (30 ml) was heated at reflux for 4 hours to yield 2-methyl-1-(2-morpholinophenyl)-3-methyl-2-thiopseudourea hydroiodide (m.p. 163°–164° C.) which was recrystallised from a 1:3 mixture of methanol and ether.

A mixture of 2-methyl-1-(2-morpholinophenyl)-3-methyl-2-thiopseudourea hydroiodide (3.9 g) and 33% methylamine in solution in absolute ethanol (40 ml) was heated for 28 hours at 50°–55° C. to yield 1,3-dimethyl-2-(2-morpholinophenyl)guanidine which was recrystallised from hexane (m.p. 137°–138° C.).

EXAMPLE 211

A mixture of 2-methyl-1-(2-morpholinophenyl)-3-methyl-2-thiopseudourea hydroiodide (3.9 g prepared as described in Example 210) and dimethylamine (25 ml of a 33% solution in ethanol) was kept at ambient temperature for 25 days. Removal of the solvent gave a residue which was purified by chromatography on an alumina column using a 1:49 mixture of methanol and dichloromethane as eluant. The resulting solid was dissolved in methanol and treated with fumaric acid to give 1,3,3-trimethyl-2-(2-morpholinophenyl)guanidine monofumarate (m.p. 192°–194° C.) which was recrystallised from a 1:2 mixture of methanol and ether.

EXAMPLE 212

Reaction of 2-morpholinophenyl isothiocyanate (3.3 g) with ethylamine generated from ethylamine hydrochloride (12.18 g) and sodium methoxide [generated from sodium (3.5 g) and methanol (100 ml)] gave 1-ethyl-3-(2-morphilinophenyl)thiourea (m.p. 118°–120° C.) which was recrystallised from a 1:1 mixture of ethylacetate and hexane.

A mixture of 1-ethyl-3-(2-morpholinophenyl) thiourea (3.2 g) and methyliodide (2 g) in acetone (25 ml) was heated at reflux for 4 hours to yield 2-methyl-3-ethyl-1-(2-morpholinophenyl)-2-thiopseudourea hydroiodide as a pale yellow solid (m.p. 170°–172° C.) which was recrystallised from acetone.

A mixture of 2-methyl-3-ethyl-1-(2-morpholinophenyl)-2-thiopseudourea hydroiodide (6 g) and 33% methylamine in absolute ethanol solution (250 ml) was heated initially for 24 hours at 45° C. and then left at room temperature for 14 days to yield 1-ethyl-2-(2-morpholinophenyl)-3-methylguanidine as a colourless solid (m.p. 118°–119° C.) which was recrystallised from hexane.

EXAMPLE 213

Sodium (23 g) was added to ethanol (300 ml) and the resulting solution of sodium ethoxide was reacted with ethylamine hydrochloride to give a solution of ethylamine which was stirred at room temperature for 30 days with 2-methyl-3-ethyl-1-(2-morpholinophenyl)-2-thiopseudourea hydroiodide (6 g prepared as described in Example 212) to yield 1,3-diethyl-2-(2-morpholinophenyl)guanidine (m.p. 101°–102° C.) which was recrystallised from hexane.

EXAMPLE 214

Reaction of 4-{2-[1-(2-hydroxyethyl)-2-imidazolidinylideneamino[phenyl}morpholine (3 g prepared as described in Example 175) in dichloromethane (20 ml) with acetic anhydride (0.86 g) yielded 4-{2-[1-(2-acetyloxyethyl)-2-imidazolidinylideneamino]phenyl}morpholine (m.p. 89°–91° C.) which was recrystallised from hexane.

EXAMPLE 215

Reaction of 4-{2-[1-(2-hydroxyethyl)-2-imidazolidinylideneamino]phenyl}morpholine (2.9 g prepared as described in Example 175) in dichloromethane (60 ml) with benzoic anhydride (2.4 g) in the presence of dry triethylamine (2 ml) and 4-dimethylaminopyridine (50 mg) gave an oil which was purified by chromatography on an alumina column using dichloromethane as eluant to give 4-{2-[1-(2-benzoyloxyethyl)-2-imidazolidinylideneaino]phenyl}morpholine (m.p. 92°–94° C.) which was recrystallised from a 1:1 mixture of ethyl acetate and hexane.

EXAMPLE 216

A solution of 4-(2-aminophenyl)morpholine (5.8 g) in dichloromethane (60 ml) was treated with n-butyl isothiocyanate (5 g) and mixture stirred at room temperature for 4 days to yield 1-(n-butyl)-3-(2-morpholinophenyl)thiourea as a pale yellow solid (m.p. 105° C.).

A mixture of 1-(n-butyl)-3-(2-morpholinophenyl)thiourea (5.8 g) and methyliodide (3.1 g) in acetone (25 ml) was heated at reflux for 4 hours to yield 2-methyl-3-(n-butyl)-1-(2-morpholinophenyl)-2-thiopseudourea hydroiodide as a colourless solid m.p. 154°–156° C.

A mixture of 2-methyl-3-(n-butyl)-1-(2-morpholinophenyl)-2-thiopseudourea hydroiodide (4.0 g) and 33% methylamine in absolute ethanol solution (200 ml) was heated initially for 24 hours at 45° and then left at room temperature for 21 days to yield 1-(n-butyl)-2-(2-morpholinophenyl)-3-methylguanidine as an oil; a solution of which in methanol (25 ml) on treatment with fumaric acid (0.7 g) gave a colourless solid which was recrystallised from a 1:1 mixture of methanol and ether to give 1-(n-butyl)-2-(2-morpholinophenyl)-3-methylguanidine monofumarate (m.p. 170°–172° C.).

EXAMPLE 217

A mixture of 2-methyl-1-(2-piperidino)phenyl]-2-thiopseudourea hydroiodide (7.5 g prepared as described in Preparative Procedure G), 2-methoxyethylamine (2 ml) and ethanol (40 ml was stirred at ambient temperature for 20 days. Removal of the solvent gave a residue which was dissolved in methanol and treated with fumaric acid to give 1-(2-methoxyethyl)-2-(2-piperidinophenyl)guanidine hemifumarate (m.p. 218°–220° C.) which was recrystallised from a 1:2 mixture of methanol and ether.

EXAMPLE 218

A mixture of 2-methyl-1-(2-morpholinophenyl)-2-thiopseudourea hydroiodide (1.7 g) prepared as described in Example 166, 2-methylthioethylamine (1.8 g) and ethanol (25 ml) was heated at 90°–95° C. for 22 hours to give 1-(2-methylthioethyl)-2-(2-morpholinophenyl)-guanidine (m.p. 115°–116° C.) which was recrystallised from hexane.

EXAMPLE 219

A mixture of 2-methyl-1-(2-morpholinophenyl)-2-thiopseudourea hydroiodide (7.6 g), 2-methoxyethylamine (2 ml) and ethanol (45 ml) was stirred at ambient temperature for 14 days to give 1-(2-methoxyethyl)-2-(2-morpholinophenyl)guanidine (m.p. 125°–128° C.) which was recrystallised from 1,2-dimethoxyethane and converted into its fumarate salt (m.p. 136°–138° C.) which was recrystallised from a 1:2 mixture of methanol and ether.

EXAMPLE 220

A mixture of 2-methyl-1-(2-morpholinophenyl)-3-methyl-2-thiopseudourea hydroiodide (7.8 g prepared as described in Example 210), n-propylamine (1.3 g) and ethanol (50 ml) was stirred at ambient temperature for 45 days to yield an oil which was purified by chromatography on a neutral alumina column using a 1:99 mixture of methanol and dichloromethane as eluent. The resulting oil was dissolved in methanol and treated with fumaric acid to give 1-(n-propyl)-2-morpholinophenyl)-3-methylguanidine monofumarate (m.p. 187°–188° C.) which was recrystallised from a 1:2 mixture of methanol and ether.

EXAMPLE 221

A mixture of 2-methyl-1-(2-morpholinophenyl)-3-methyl-2-thiopseudourea hydroiodide (3.9 g prepared as described in Example 210), 2-methoxyethylamine (0.82 g) and ethanol (25 ml) was stored at ambient temperature for three months to yield an oil which was dissolved in methanol and treated with fumaric acid to give 1-methyl-2-(2-morpholinophenyl)-3-(2-methoxyethyl)guanidine monofumarate (m.p. 158°–160° C.) which was recrystallised from a 1:2 mixture of methanol and ether.

EXAMPLE 222

A mixture of 2-methyl-1-(2-morpholinophenyl)-3-methyl-2-thiopseudourea hydriodide (7.86 g prepared as described in Example 210), cyclopentylamine (2.9 g), anhydrous sodium carbonate (6.36 g) and ethanol (100 ml) was heated in a stainless steel pressure vessel in an oil bath at 110° C. for 24 hours. The reaction mixture was cooled, filtered and the solvent was partially removed. The residue was poured into ice and the resulting mixture extracted with dichloromethane. The extract was dried, filtered and the solvent removed to give a residue which was treated with fumaric acid to give 1-cyclopentyl-2-(2-morpholinophenyl)-3-methylguanidine monofumarate (m.p. 220° C.) which was recrystallised from a 1:1 mixture of methanol and ether.

EXAMPLE 223

A mixture of 2-methyl-1-(2-morpholinophenyl)-3-methyl-2-thiopseudourea hydriodide (3.9 g prepared as described in Example 210), pyrrolidine (1 ml) and ethanol (40 ml) was heated under reflux for two weeks to yield an oil which was purified by chromatography on a neutra alumina column eluted with a 1:1 mixture of dichloromethane and hexane and then a 1:9 mixture of methanol and dichloromethane to give N-methyl-N'-(2-morpholinophenyl)pyrrolidine-1-carboxamidine which was converted into its monofumarate salt (m.p. 168°–171° C.) which was recrystallised from propan-2ol.

EXAMPLE 224

A mixture of 2-methyl-1-(2-morpholinophenyl)-3-ethyl-2-thiopseudourea hydroiodide (10 g prepared as described in Example 212), n-butylamine (2.7 g) and t-butanol (75 ml) was heated at 90°–95° C. for 172 hours to yield 1-(n-butyl)-2-(2-morpholinophenyl)-3-ethylguanidine which was converted into its monofumarate salt (m.p. 159°–160° ) which was recrystallised from a 1:2 mixture of methanol and ether.

EXAMPLE 225

Reaction of 5-chloro-2-morpholinoaniline (2.8 g) (2.8 g) with n-butyl isothiocyanate (1.5 g) in ethanol (20 ml) at room temperature for 60 days yielded 1-(n-butyl)-3-(5-chloro-2-morpholinophenyl)thiourea (m.p. 150°–152° C.).

A mixture of 1-(n-butyl)-3-(5-chloro-2-morpholinophenyl)thiourea (2.6 g), methyl iodide (1.4 g) and acetone (20 ml) was heated under reflux for 3 hours to give 2-methyl-1-(5-chloro-2-morpholinophenyl)-3-(n-butyl)-2-thiopseudourea hydroiodide (m.p. 130°–132° C.).

A mixture of 2-methyl-1-(5-chloro-2-morpholinophenyl)-3-(n-butyl)-2-thiopseudourea hydroiodide (3.4 g) and a 33% ethanolic solution of methylamine (10 ml) were stored at ambient temperature in a sealed container for 8 months to yield 1,3-dimethyl-2-(5-chloro-2-morpholinophenyl)guanidine (m.p. 145°–146° C.) which was recrystallised from hexane. In this reaction the butylamino and the methylthio group of the starting material are replaced by a methylamino group.

EXAMPLE 226

Reaction of 1-(2-aminophenyl)pyrrolidine (10 g) with methyl isothiocyanate (6.3 g) in dichloromethane (45 ml) at room temperature for 4 days gave 1-methyl-3-[2-(1-pyrrolidinyl)phenyl]thiourea (m.p. 125°–126° C.).

A mixture of 1-methyl-3-[2-(1-pyrrolidinyl)phenyl]thiourea (18.5 g) and methyl iodide (12.3 g) and acetone (100 ml) was heated under reflux for 2.5 hours to give 2-methyl-1-[2-(1-pyrrolidinyl)phenyl]-3-methyl-2-thiopseudourea hydroiodide (m.p. 161°–162° C.).

A mixture of 2-methyl-1-[2-(1-pyrrolidinyl)phenyl]-3-methyl-2-thiopseudourea hydroiodide (14.7 g), allylamine (4.45 g) and ethanol (65 ml) was stored at ambient temperature for 50 days and was then heated under reflux for 20 hours to give an oil which was treated with fumaric acid to give 1-allyl-2-[2-(1-pyrrolidinyl)phenyl]-3-methylguanidine monofumarate (m.p. 162°–163° C.) which was recrystallised from a 1:2 mixture of methanol and ether.

EXAMPLE 227

A solution of 4-(2-amino-4-methylphenyl)morpholine (5.7 g) in dichloromethane (30 ml) was treated with methylisothiocyanate (2.8 g) and the reaction mixture kept at room temperature for 6 days to yield 1-methyl-3-(5-methyl-2-morpholinophenyl)thiourea as a colourless solid (m.p. 107° C.).

A mixture of 1-methyl-3-(5-methyl-2-morpholinophenyl)thiourea (6.4 g) and methyl iodide (3.8 g) in acetone (60 ml) was heated at reflux for 4 hours to give 2-methyl-1-(5-methyl-2-morpholinophenyl)-3-methyl-2-thiopseudourea hydroiodide as a pale yellow solid (m.p. 160°–161° C.).

A mixture of 2-methyl-1-(5-methyl-2-morpholinophenyl)-3-methyl-2-thiopseudourea hydroiodide (6 g) and 33% methylamine in absolute ethanol solution (250 ml) was kept at room temperature for 21 days to yield 1,3-dimethyl-2-(5-methyl-2-morpholinophenyl)guanidine as an oil which was dissolved in methanol (60 ml) and treated with fumaric acid (1.7 g) to give 1,3-dimethyl-2-(5-methyl-2-morpholinophenyl)guanidine fumarate (1.2 g) as a colourless solid which was recrystallised from a 1:1 mixture of methanol and ether (m.p. 201°–202° C.).

EXAMPLE 228

A mixture of 2-methyl-1-(5-methyl-2-morpholinophenyl)-3-methyl-2-thiopseudourea hydroiodide (8.4 g prepared as described in Example 227), N-(2-hydroxyethyl)ethylenediamine (6.8 ml) and ethanol (80 ml)) was heated under reflux for 30 hours to give an oil which was treated with fumaric acid in methanol to give 4-{2-[1-(2-hydroxyethyl)-2-imidazolidinylideneamino]-4-methylphenyl}morpholine sesquifumarate (m.p. 135°–136° C.).

EXAMPLE 229

A mixture of 2-methyl-1-(2-morpholinophenyl)-3-methyl-2-thiopseudourea (4 g prepared from the hydroiodide salt described in Example 210), potassium hydroxide (1.7 g), n-pentylamine (2.1 g), lead acetate trihydrate (5.8 g) and ethanol (20 ml) were heated at 90°–95° C. for 40 minutes to yield an oil which was extracted with hexane to give 1-methyl-2-(2-morpholinophenyl)-3-(n-pentyl)guanidine which was converted into its monofumarate salt (m.p. 148°–149° C.) which was recrystallised from a 3:5 mixture of methanol and ether.

EXAMPLE 230

A mixture of 2-methyl-1-(5-methyl-2-morpholinophenyl)-3-methyl-2-thiopseudourea hydroiodide (12.2 g prepared as described in Example 227), n-butylamine (2.4 g) and ethanol (80 ml) was stored at ambient temperature for 4 months. Lead acetate trihydrate (9 g) was then added and the mixture heated under reflux for one hour to yield 1-(n-butyl)-2-(5-methyl-2-morpholinophenyl)-3-methylguanidine which was converted into its monofumarate salt (m.p. 150° C.) which was recrystallised from a 1:2 mixture of methanol and ether.

EXAMPLE 231

Reaction of 6-methyl-2-morpholinoaniline (8.75 g) with methyl isothiocyanate (4.7 g) in dichloromethane (50 ml) at room temperature for four days yielded N-methyl-N'-(6-methyl-2-morpholinophenyl)thiourea (m.p. 182°–183° C.).

A mixture of N-methyl-N'-(6-methyl-2-morpholinophenyl)thiourea (11.5 g), methyl iodide (6.75 g) and acetone (100 ml) was heated under reflux for 2.5 hours to give 2-methyl-1-(6-methyl-2-morpholinophenyl)-3-methyl-2-thiopseudourea hydroiodide (m.p. 187°–188° C.).

A mixture of 2-methyl-1-(6-methyl-2-morpholinophenyl)-3-methyl-2-thiopseudourea hydroiodide (17.8 g), n-butylamine (6.4 g) and ethanol (60 ml) was stored at ambient temperature for 60 days. Potassium hydroxide (2.2 g) and then lead acetate trihydrate (7.6 g) were added and the mixture was heated under reflux for 5 hours to yield 1-(n-butyl)-2-(6-methyl-2-morpholinophenyl)-3-methylguanidine which was converted into its monofumarate salt (m.p. 203°–204° C.) which was recrystallised from a 1:2 mixture of methanol and ether.

EXAMPLE 232

Reaction of N-(2-morpholinophenyl) isothiocyanate (4 g) in ethanol (10 ml) with 33% ethanolic dimethylamine solution (15 ml) at 15° C. for four hours gave 1,1-dimethyl-3-(2-morpholinophenyl)thiourea (m.p. 150°–152° C.).

A mixture of 1,1-dimethyl-3-(2-morpholinophenyl)thiourea (7.5 g), methyl iodide (1.7 ml) and acetone was heated under reflux for 2 hours to give 2-methyl-1-(2-morpholinophenyl)-3,3-dimethyl-2-thiopseudourea (m.p. 162°–163° C.).

A mixture of 2-methyl-1-(2-morpholinophenyl)-3,3-dimethyl-2-thiopseudourea hydroiodide (2 g), a saturated ethanolic ammonia solution (10 ml) and pyridine (10 ml) was heated at 90°–95° C. for 19 hours in a sealed stainless steel pressure vessel. Pyridine was removed by evaporation under reduced pressure and the residue suspended in water. 1,1-Dimethyl-2-(morpholinophenyl)guanidine (m.p. 142°–143° C.) was collected by filtration, washed with water, dried and recrystallised from hexane.

EXAMPLE 233

A mixture of 2-methyl-1-(2-morpholinophenyl)-2-thiopseudourea hydroidide (3.8 g), a 33% ethanolic solution of dimethylamine (5 ml) and pyridine (25 ml) was heated at 80° C. for 6 hours. Pyridine was removed by evaporation under reduced pressure and the residue treated with a mixture of ice and water to give 1,1-dimethyl-2-(2-morpholinophenyl)guanidine (m.p. 142°–144° C.) which was recrystallised from hexane.

EXAMPLE 234

A mixture of 2-methyl-1-(2-morpholinophenyl)-2-thiopseudourea hydroidide (3.8 g), a 33% ethanolic solution of dimethylamine (5 ml) and triethylamine (25 ml) was heated at 80° C. for 8 hours. Triethylamine was removed by evaporation under reduced pressure and the residue treated with a mixture of ice and water to give 1,1-dimethyl-2-(2-morpholinophenyl)guanidine (m.p. 141°–143° C.) which was recrystallised from hexane.

EXAMPLES 235 TO 241

The compounds of formula I listed in Table VIII were prepared by heating a mixture of a thiourea of formula XVI in which $R_{14}$ is methyl and $R_{15}$ is H (A g), potassium hydroxide (B g), an amine of formula $H_2NR_6$ (C g), lead acetate trihydrate (D g) and ethanol (E ml) at 90°–95° C. for F hours to yield an oil which is dissolved in methanol and treated with fumaric acid to give the monofumarate salt of the compounds of formula I. The melting point of the monofumarate salt is given in the column headed "m.p." and the solvent from which the salt was recrystallised is identified by the following Notes.

Notes to Table VIII

(59) Salt recrystallised from methanol.

(60) The thiourea starting material was prepared by the reaction of 4-(2-amino-4-fluorophenyl)morpholine (6 g) with methyl isothiocyanate (2.6 g) in dichloromethane (50 ml) at room temperature for 25 days to give 1-methyl-3-(5-fluoro-2-morpholinophenyl)thiourea (m.p. 145°–148° C.).

(61) The free base was purified by chromatography on a neutral alumina column using dichloromethane as eluent.

(62) The thiourea starting material was prepared by the reaction of 4-(2-amino-4-methylthiophenyl)morpholine (9.5 g) with methyl isothiocyanate (3.1 g) in dichloromethane (100 ml) at room temperature for 30 days to give 1-methyl-3-(5-methylthio-2-morpholinophenyl)thiourea (m.p. 132°–133° C.).

(63) Salt recrystallised from a 1:2 mixture of methanol and ether.

(64) Salt recrystallised from propan-2-ol.

TABLE VIII

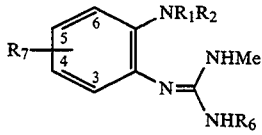

| Ex | A | B | C | D | E | F | $NR_1R_2$ | $R_6$ | $R_7$ | mp(°C.) | Notes |
|---|---|---|---|---|---|---|---|---|---|---|---|
| 235 | 5.4 | 2.2 | 2.2 | 7.4 | 40 | 2 | morpholino | n-Bu | 4-F | 212(dec) | (59)(60) |
| 236 | 5.9 | 2.24 | 2.2 | 7.6 | 60 | 1.5 | morpholino | n-Bu | 4-SMe | 120–122 | (61)(62)(63) |
| 237 | 5 | 2.2 | 2.9 | 7.6 | 50 | 2 | morpholino | i-Bu | H | 157–158 | (64) |
| 238 | 2.5 | 1.1 | 1 | 3.7 | 20 | 2 | morpholino | s-Bu | H | 170(dec) | (63) |
| 239 | 5 | 2.2 | 2.93 | 7.6 | 50 | 3.5 | morpholino | t-Bu | H | 182–184 | (63) |
| 240 | 5 | 2.2 | 2.3 | 7.6 | 50 | 4.5 | morpholino | allyl | H | 189–190 | (63) |
| 241 | 3.9 | 1.64 | 2.1 | 5.5 | 50 | 2.5 | thiamorpholino | n-Bu | H | 162–163 | (59) |

EXAMPLE 242

Reaction of 2-morpholino-5-trifluoromethylaniline (12 g) with thiophosgene (8.6 g) in dioxan (30 ml) and water (100 ml) at 0° C. for 30 minutes and then at room temperature for 2 hours yielded a residue which was extracted with dichloromethane to give 2-morpholino-5-trifluoromethylphenyl isothiocyanate as a yellow oil.

Reaction of 2-morpholino-5-trifluoromethylphenyl isothiocyanate (12 g) in ethanol (20 ml) with 33% ethanolic ammonia solution (50 ml) at room temperature for 2 hours gave 1-(2-morpholino-5-trifluoromethylphenyl)thiourea (m.p. 196°–197° C.).

A mixture of 1-(2-morpholino-5-trifluoromethylphenyl)thiourea (6.1 g), potassium hydroxide (2.2 g), a 33% ethanolic solution of dimethylamine (5.6 ml), lead acetate trihydrate (7.5 g) and ethanol (40 ml) was heated at 90°–95° C. for 2 hours to yield 1,1-dimethyl-2-(2-morpholino-5-trifluoromethylphenyl)guanidine (m.p. 132°–135° C.) which was recrystallised from ethylacetate and converted into its fumarate salt (m.p. 228°–230° C.) which was recrystallised from a 1:2 mixture of methanol and ether.

EXAMPLE 243

Reaction of 5-cyano-2-morpholinoaniline (2 g) with thiophosgene (1.15 ml) in dioxan (2 ml) and water (25 ml) at 0° C. for 30 minutes and then at room temperature for 2 hours yielded a residue which was extracted with dichloromethane to give 5-cyano-2-morpholinophenyl isothiocyanate as an oil.

Reaction of 5-cyano-2-morpholinophenyl isothiocyanate (2.5 g) in ethanol (10 ml) with 25% aqueous ammonia solution (1 ml) at room temperature for 3 hours gave 1-(5-cyano-2-morpholinophenyl)thiourea (m.p. 193°–194° C.).

A mixture of 1-(5-cyano-2-morpholinophenyl)thiourea (5.2 g), potassium carbonate (8.3 g), a 33% ethanolic solution of dimethylamine (15 ml), lead acetate trihydrate and ethanol (25 ml) was heated under reflux for 3 hours to yield 1,1-dimethyl-2-(5-cyano-2-morpholinophenyl)guanidine (m.p. 125°–127° C.) which was converted into its monofumarate salt [m.p. 223°–225° C. (dec)] which was recrystallised from methanol.

EXAMPLE 244

A mixture of 1,1-dimethyl-3-(2-morpholinophenyl)-thiourea (2.65 g prepared as described in Example 232), n-propylamine (1.6 ml), lead acetate trihydrate (3.8 g), potassium hydroxide (1.2 g) and ethanol (25 ml) was heated under reflux for 4 hours. A further amount of n-propylamine (1.6 ml) was added and the mixture heated under reflux for a further 8 hours. The reaction mixture yielded a residue which was extracted with ether. The extract was decolourised with charcoal, filtered and the solvent removed to leave a sticky solid which was dissolved in methanol (10 ml) and treated with fumaric acid to give 1,3-di-(n-propyl)-2-(2-morpholinophenyl)guanidine hemifumarate (m.p. 212°–214° C.) which was recrystallised from a 1:2 mixture of methanol and ether.

EXAMPLE 245

A mixture of 1,1-dimethyl-3-(2-morpholinophenyl) thiourea (2.65 g prepared as described in Example 232), lead acetate trihydrate (3.8 g), saturated ethanolic ammonia solution (25 ml), potassium hydroxide (1.12 g) and ethanol (20 ml) where heated at 90°–95° C. is a sealed stainless steel pressure vessel for 5 hours. The reaction mixture was filtered and the solid collected washed with ethanol. The washings were added to the filtrate and the volume reduced by evaporation. Ice was added and the resulting solid was collected by filtration, washed with water and dried to give 1,1-dimethyl-2-(2-morpholinophenyl)guanidine (m.p. 141°–142° C.) which was recrystallised from hexane.

EXAMPLES 246 TO 269

Reaction of a compound of formula VII in the form of its hydrochloride salt (K grammes) and a compound of formula NC—NR$_5$R$_6$ (L grammes) in m-cresol (M ml) was heated at 90°–95° C. for N hours to give the compounds identified in Table IX.

Notes to Table IX

Notes (32), (38), (44) and (45) have the meaning given hereinbefore.

(65) Reaction performed at 110° C.

(66) The product was isolated as its monofumarate salt which was recrystallised from a 1:1 mixture of methanol and ether.

(67) Reaction performed at 90°–95° C. for 8 hours and then at 115°–120° C. for 4 hours.

(68) Reaction performed at 120°–125° C.

(69) The reaction mixture was heated at 90°–95° C. for 9 hours and then at 120° C. for 21 hours.

(70) The reaction mixture yielded an oil which was extracted with boiling hexane to yield the free base which was converted into its monofumarate salt which was recrystallised from a 1:3 mixture of methanol and ether.

(71) The reaction mixture yielded an oil which was extracted with hexane to yield the free base as an oil which was purified by chromatography on a neutral alumina column using the following eluents sequentially:—hexane, a 1:1 mixture of dichloromethane and hexane, dichloromethane and a 1:99 mixture of methanol and dichloromethane to give the base which was converted into its monofumarate salt which was recrystallised from 2:7 mixture of methanol and ether.

TABLE IX

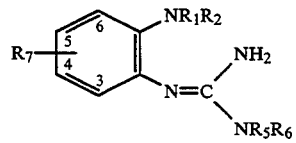

| Ex | K | L | M | N | NR$_1$R$_2$ | R$_5$ | R$_6$ | R$_7$ | mp(°C.) | Notes |
|---|---|---|---|---|---|---|---|---|---|---|
| 246 | 6.4 | 1.8 | 25 | 3.5 | morpholino | H | H | H | 189 | (44) |
| 247 | 19.2 | 9.45 | 80 | 5 | morpholino | Me | Me | H | 215–216 | (45) |
| 248 | 7.4 | 5.5 | 25 | 5.5 | morpholino | Me | Me | 4-Me | 122–123 | (32) |
| 249 | 10.8 | 5 | 45 | 10 | morpholino | Me | Me | 3-Me | 230–231 | (45)(65) |
| 250 | 7.3 | 3.54 | 50 | 42 | morpholino | Me | Me | 5-Cl | 152 | (44) |
| 251 | 7.2 | 3.54 | 50 | 50 | morpholino | Me | Me | 6-Cl | 190–192 | (45) |
| 252 | 6.3 | 2.7 | 25 | 18 | morpholino | Me | Me | 4-OMe | 220 | (45) |
| 253 | 6.8 | 4.25 | 40 | 18 | morpholino | Me | Me | 4-SMe | 220(dec) | (45) |
| 254 | 5.7 | 2.93 | 25 | 6 | morpholino | Me | Me | 5-Me | 225–226 | (45) |
| 255 | 4.9 | 2.1 | 25 | 9 | morpholino | Me | Me | 4-Et | 217–218 | (45) |
| 256 | 5.4 | 5.4 | 40 | 20 | morpholino | Me | Me | 4-CH$_2$SMe | 198–200 | (38) |
| 257 | 8.6 | 5.9 | 30 | 15 | morpholino | Et | Et | H | 193–194 | (45) |
| 258 | 8.6 | 6.7 | 40 | 8 | morpholino | Me | Bu | H | 187–188 | (45) |
| 259 | 8.1 | 8.8 | 50 | — | morpholino | (CH$_2$)$_2$OMe | (CH$_2$)$_2$OMe | H | 160–162 | (66)(67) |
| 260 | 6.5 | 5 | 20 | 7 | morpholino | —(CH$_2$)$_2$O(CH$_2$)$_2$— | | H | 202–203 | (45) |
| 261 | 10.2 | 6.8 | 40 | 12 | morpholino | —(CH$_2$)$_4$— | | H | 237–238 | (45) |
| 262 | 10.6 | 5.25 | 30 | 16 | piperidino | Me | Me | H | 189–190 | (68)(45) |
| 263 | 8.2 | 4.3 | 40 | | pyrrolidinyl | Me | Me | H | 201–202 | (45)(69) |
| 264 | 4.6 | 2.1 | 25 | 1 | thiamorpholino | Me | Me | H | 209–210 | (45) |
| 265 | 4.5 | 2.3 | 50 | 6 | NMe$_2$ | Me | Me | H | 188 | (70) |
| 266 | 4.33 | 1.75 | 10 | 8 | N(Me)CH$_2$CH$_2$OMe | Me | Me | H | 162–163 | (71) |
| 267 | 11.38 | 3.52 | 20 | 8 | 4-methyl-1-piperazinyl | Me | Me | H | 205–206 | (38) |
| 268 | 7 | 5.5 | 25 | 10 | piperidino | —(CH$_2$)$_2$O(CH$_2$)$_2$— | | H | 208–209 | (68)(45) |
| 269 | 7.5 | 5.8 | 25 | 13 | morpholino | —(CH$_2$)$_5$— | | H | 216–217 | (45) |

EXAMPLE 270

A mixture of 4-(2-aminophenyl)morpholine hydrochloride (2.1 g) and N,N-dimethylcyanamide (7 ml) was heated under nitrogen at 165°–170° C. for 12 hours. The reaction mixture was cooled to 10° C. and the precipitate collected by filtration, washed with ether and stirred with 40% aqueous sodium hydroxide solution.

The resulting mixture was extracted with dichloromethane and the extract washed with brine and dried. Removal of the solvent yielded a residue which was recrystallised from hexane to give 1,1-dimethyl-2 (2-morpholinophenyl)guanidine (m.p. 144°–145° C.).

EXAMPLE 271

A mixture of 4-(2-amino-4-methoxycarbonylphenyl)-morpholine (2.7 g), N,N-dimethyl cyanamide (1 g) and m-cresol (15 ml) was heated at 90°–95° C. for 10 hours. Ice was added and the reaction mixture acidified to pH 4 by the addition of 2N hydrochloric acid and the resultant mixture extracted with ether. The aqueous layer was cooled, basified to pH 8 by the addition of solid sodium bicarbonate and then extracted with dichloromethane. The extract was dried and the solvent removed to yield an oily residue which was purified by chromatography on a neutral alumina column eluted with a 1:99 mixture of methanol and dichloromethane to give 1,1-dimethyl-2-(5-methoxycarbonyl-2-morpholinophenylguanidine (m.p. 152°–154° C.).

EXAMPLE 272

1-(2-morpholinophenyl)thiourea (10.6 g) was suspended in boiling water (80 ml) and a solution of potassium hydroxide (25.2 g) in hot water (70 ml) was added. The mixture was heated to 90° C. and aliquot portions of a hot solution of lead acetate trihydrate (17.5 g) in water (80 ml) added and the mixture heated under reflux for 10 minutes and cooled to ambient temperature. The mixture was filtered and the filtrate acidified with acetic acid to pH 6. The solid which formed was separated by filtration, washed with water and recrystallised from ethylacetate to give N-(2-morpholinophenyl)-cyanamide (m.p. 175°–176° C.).

N-(2-morpholinophenyl)cyanamide (2 g) was heated under reflux with a 33% solution of dimethylamine in ethanol (15 ml) for 4 hours. The mixture was then cooled and the solvent removed by evaporation to give a residue which was suspended in 20% aqueous sodium hydroxide solution. The suspension was extracted with dichloromethane (3×25 ml) and the extracts were washed with water, and then brine, dried and evaporated to give 1,1-dimethyl-2-(2-morpholinophenyl) guanidine (m.p. 142°–143° C.) which was recrystallised from hexane.

EXAMPLES 273–285

In a similar manner to that described in Example 272, N-(2-morpholinophenyl)cyanamide (P g) was heated under reflux with an amine of formula $HNR_5R_6$ (Q g) and ethanol (R ml) for T hours to give the compounds listed in Table X.

Notes to Table X

Notes (32), (38), (44) and (45) have the meaning given hereinbefore

(72) A 33% ethanolic solution of methylamine (25 ml) was used as reactant.

(73) Reaction performed at 90°–95° C.

(74) Product isolated as its monofumarate salt which was recrystallised from a 2:3 mixture of methanol and ether.

(75) Product recrystallised from a 1:1 mixture of hexane and ethyl acetate.

(76) Reaction performed at ambient temperature for 2 hours and then at 90°–95° C. for 20 minutes.

(77) Product recrystallised from a 3:7 mixture of ethylacetate and hexane.

(78) Reaction performed at ambient temperature for 4 hours and then heated under reflux for 4 hours.

TABLE X

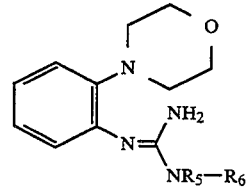

| Ex | P | Q | R | T | $R_5$ | $R_6$ | mp(°C.) | Notes |
|---|---|---|---|---|---|---|---|---|
| 273 | 2.5 | | | 2 | H | Me | 171–172 | (72)(73)(74) |
| 274 | 2 | 1.3 | 15 | 1 | H | Et | 103–105 | (75) |
| 275 | 2 | 2.2 | 15 | 3 | H | Bu | 114–116 | (44)(73) |
| 276 | 2 | 3.4 | 20 | | Me | Et | 130–132 | (76)(32) |
| 277 | 4 | 5 | 25 | 1 | Me | $CH_2CH_2SMe$ | 230(dec) | (45)(73) |
| 278 | 3 | 4.6 | 30 | 1.25 | Me | $CH_2CH_2OMe$ | 192–193 | (38) |
| 279 | 2 | 2.2 | 10 | 1.5 | Me | allyl | 125 | (73)(77) |
| 280 | 4 | 6.2 | 30 | 1.5 | Et | $CH_2CH_2OMe$ | 168–170 | (38) |
| 281 | 4 | 2.5 | 25 | 2 | allyl | allyl | 188–190 | (73)(38) |
| 282 | 5 | 5 | 50 | 2 | —$(CH_2)_2NMe(CH_2)_2$— | | 146–147 | (32) |
| 283 | 2 | 1.7 | 20 | 6 | —$CH_2CHMeOCHMeCH_2$— | | 175–177 | (44) |
| 284 | 4 | 4.1 | 40 | 3 | —$(CH_2)_2CHMe(CH_2)_2$— | | 133–135 | (32) |
| 285 | 3 | 22 | 40 | | —$(CH_2)_2S(CH_2)_2$— | | 148–150 | (32)(78) |

EXAMPLE 286

Reaction of 4-(2-amino-4-chlorophenyl)morpholine (8.5 g) with thiophosgene (4.6 ml) in dioxan (25 ml) and water (100 ml) for 30 minutes at 0° C. and for 3 hours at room temperature gave 5-chloro-2-morpholinophenyl isothiocyanate as a pale yellow solid (m.p. 86°–87° C.).

Reaction of 5-chloro-2-morpholinophenyl isothiocyanate (10 g) with 33% alcoholic ammonia solution (60 ml) at room temperature for 14 hours gave 1-(5-chloro-2-morpholinophenyl)thiourea as a yellow solid (m.p. 174°–175° C.).

A mixture of 1-(5-chloro-2-morpholinophenyl) thiourea (5.97 g) suspended in water (40 ml), lead acetate trihydrate (8.75 g) in water (40 ml) and potassium hydroxide (12.6 g) in water (35 ml) was heated under reflux for 15 minutes to give N-(5-chloro-2-morpholinophenyl)cyanamide as a white solid (m.p. 305°-308° C.).

In a similar manner to that described in Example 272, N-(5-chloro-2-morpholinophenyl)cyanamide (2.3 g) in ethanol (10 ml) and a 33% ethanolic solution of dimethylamine (6 ml) were heated under reflux for 4 hours to give 1,1-dimethyl-2-(5-chloro-2-morpholinophenyl)guanidine (m.p. 135°-138° C.) which was recrystallised from hexane and then was converted into its monofumarate salt (m.p. 223°-225° C.) which was recrystallised from methanol.

EXAMPLE 287

A mixture of 5-fluoro-2-morpholino aniline (6 g) and thiophosgene (5.2 g) in dioxan (20 ml) and water (40 ml) was stirred at 0° C. for 15 minutes and at room temperature for one hour to yield a residue which was extracted with dichloromethane to give an oil which was purified by chromatography on a silica gel column (mesh 100-200) using a 1:9 mixture of ethylacetate and hexane as eluant to give 5-fluoro-2-morpholinophenyl isothiocyanate as an oil.

Reaction of 5-fluoro-2-morpholinophenyl isothiocyanate (5.8 g) with 33% ethanolic ammonia solution (30 ml) at room temperature for 3 hours gave 1-(5-fluoro-2-morpholinophenyl)thiourea as a white solid (m.p. 195-196).

A mixture of 1-(5-fluoro-2-morpholinophenyl)thiourea (5.1 g) suspended in water (36.5 ml), lead acetate trihydrate (7.95 g) in water (36 ml) and potassium hydroxide (11.45 g) in water (32 ml) was heated under reflux for 25 minutes to give N-(5-fluoro-2-morpholinophenyl)cyanamide as a white solid (m.p. 168°-170° C.).

In a similar manner to that described in Example 286, N-(5-fluoro-2-morpholinophenyl)cyanamide (2.2 g) in ethanol (10 ml) and a 33% ethanolic solution of dimethylamine (6 ml) was heated under reflux for 20 minutes to give 1,1-dimethyl-2-(5-fluoro-2-morpholinophenyl)guanidine (m.p. 137°-138° C.) which was recrystallised from hexane and converted into its fumarate salt (m.p. 222°-224° C.) which was recrystallised from methanol.

EXAMPLE 288

Reaction of 3-methyl-2-morpholinoaniline (9.4 g) with thiophosgene (6 ml) in dioxane (50 ml) and water (200 ml) at 0° C. for 30 minutes and at room temperature for 2 hours gave a product which was extracted with dichloromethane to give 3-methyl-2-morpholinophenyl isothiocyanate as a red oil.

Reaction of 3-methyl-2-morpholinophenyl isothiocyanate (8 g) in ethanol (5 ml) with a saturated solution of ammonia in ethanol (60 ml) at room temperature for 4 hours gave 1-(3-methyl-2-morpholinophenyl)thiourea (m.p. 178°-179° C.).

A mixture of 1-(3-methyl-2-morpholinophenyl)thiourea (6 g) suspended in water (40 ml), lead acetate trihydrate (9 g) in water (40 ml), potassium hydroxide (13.5 g) in water (35 ml) was heated at 90°-95° C. for 1 hour to give N-(3-methyl-2-morpholinophenyl)cyanamide (m.p. 137°-138° C.) which was recrystallised from ethyl acetate.

In a similar manner to that described in Example 286, N-(3-methyl-2-morpholinophenyl)cyanamide (2.5 g) in ethanol (8 ml) and a 33% ethanolic solution of dimethylamine (3.5 ml) were heated under reflux for 1 hour. A further amount of the 33% ethanolic solution of dimethylamine (3.5 ml) was added and the mixture heated under reflux for a further hour to give 1,1-dimethyl-2-(3-methyl-2-morpholinophenyl)guanidine (m.p. 100° C.) which was recrystallised from hexane and converted into its monofumarate salt (m.p. 180° C.) which was recrystallised from a 1:1 mixture of methanol and ether.

EXAMPLE 289

Reaction of 4-methoxy-2-morpholinoaniline (4.7 g) and thiophosgene (2.9 ml) in dioxan (25 ml) and water (75 ml) for 30 minutes at 0° C. and 3 hours at room temperature yielded a residue which was extracted with dichloromethane to give 4-methoxy-2-morpholinophenyl isothiocyanate as an oil.

Reaction of 4-methoxy-2-morpholinophenyl isothiocyanate (4.1 g) with a saturated solution of ammonia in ethanol (30 ml) for 24 hours at room temperature gave 1-(4-methoxy-2-morpholinophenyl)thiourea (m.p. 175° C.).

A mixture of 1-(4-methoxy-2-morpholinophenyl)thiourea (3.8 g) suspended in water (26 ml), lead acetate trihydrate (5.7 g) in water (26 ml) and potassium hydroxide (8.4 g) in water (24 ml) was heated at 90°-95° C. for 30 minutes to give N-(4-methoxy-2-morpholinophenyl)cyanamide.

A mixture of N-(4-methoxy-2-morpholinophenyl)cyanamide (1.9 g) and 33% ethanolic dimethylamine solution (2.5 ml) was heated under reflux for 15 minutes to give 1,1-dimethyl-2-(4-methoxy-2-morpholinophenyl)guanidine (m.p. 135° C.) which was recrystallised from hexane.

EXAMPLE 290

A mixture of 5-isobutyl-2-morpholinoaniline hydrochloride (4.1 g), N,N-dimethylcyanamide (1.77 g) and m-cresol (15 ml) was heated at 90°-95° C. for 6 hours to yield a residue which was extracted with hot hexane, decolourised with charcoal and purified by chromatography on an alumina column eluted with a 2:98 mixture of methanol and dichloromethane. The resulting product was crystallised from a 1:3 mixture of ethylacetate and hexane. The initial precipitate was removed by filtration and the filtrate evaporated to dryness to give a residue which was recrystallised from a 1:3 mixture of ethylacetate and hexane to give 1,1-dimethyl-2-(5-isobutyl-2-morpholinophenyl)guanidine.

EXAMPLE 291

Sodium chlorite (5.6 g), cuprous chloride (0.2 g), cupric chloride dihydrate (0.34 g) were added to a solution of sodium carbonate (3.75 g) in water (25 ml). The mixture was cooled to 20° C. and a solution of N-(2-morpholinophenyl)thiourea (6 g) in dichloromethane (45 ml) was added over 15 minutes. The temperature was raised to 40° C. and maintained at this level for 4.5 hours. Water (100 ml) and dichloromethane (200 ml) were added and the mixture stirred for ten minutes. The organic layer was separated and the aqueous layer washed with dichloromethane. The combined organic layer was washed with brine and dried. Removal of the solvent gave a residue which was stirred with 20% aqueous sodium hydroxide solution (100 ml) and heated on a steam bath and then filtered. The filtrate was washed with ether, acidified to pH 4 with acetic acid and extracted with dichloromethane. The extract was washed with brine, dried and the solvent removed to give a residue which was purified by chromatography on a silica column which was eluted with hexane to which ethylacetate (up to 30%) was added progressively to raise the polarity. N-(2-morpholinophenyl)cyanamide (m.p. 175°–176° C.).

A mixture of N-(2-morpholinophenyl)cyanamide (1.5 g) and a 33% ethanolic solution of dimethylamine (12 ml) was heated under reflux for 4 hours. Removal of solvent gave a residue to which was added dichloromethane (100 ml) and brine (50 ml). The mixture was stirred for 5 minutes and the organic layer separated and dried. Removal of the solvent gave 1,1-dimethyl-2-(2-morpholinophenyl)guanidine (m.p. 144°–145° C.) which was recrystallised from hexane.

EXAMPLE 292

1,1-dimethyl-2-(5-methylthio-2-morpholinophenyl)guanidine in the form of its free base (1.3 g) obtained from the product of Example 253, sodium metaperiodate (1 g), methanol (10 ml) and water (4 ml) were stored at ambient temperature for 20 hours to yield 1,1-dimethyl-2-(5-methylsulphinyl-2-morpholinophenyl)guanidine (m.p. 160°–161° C.) which was recrystallised from ethyl acetate.

EXAMPLE 293

A solution of 1-methyl-2-(2-morpholinophenyl)thiourea (6.2 g) in dichloromethane (30 ml) was added over 15 minutes to a stirred mixture of aqueous sodium carbonate solution (3.75 g in 25 ml), sodium chlorite (5.6 g), cuprous chloride (0.2 g), cupric chloride dihydrate (0.34 g) and benzyltrimethylammonium chloride (0.6 g). The resulting mixture was stirred for 2 hours and then sodium chlorite (2.4 g) and benzyltrimethylammonium chloride (0.4 g) were added and the mixture stirred for 1½ hours. Dichloromethane (200 ml) and water (50 ml) were added and the aqueous layer extracted with dichloromethane (2×100 ml). The extracts were combined, washed with brine, dried and filtered. Removal of the solvent gave a residue which was purified by chromatography on a silica gel column using hexane and then a 1:4 mixture of ethyl acetate and hexane as eluant to give N-methyl-N'-(2-morpholinophenyl)carbodiimide (m.p. 67°–68° C.).

A mixture of N-methyl-N'-(2-morpholinophenyl)carbodiimide (1 g), n-butylamine (0.5 g) and t-butanol (5 ml) was heated at 90°–95° C. for four hours. The solvent was removed by evaporation and the residue dissolved in dichloromethane (100 ml) and the resulting solution was washed with water, dried and filtered. Removal of the solvent gave 1-(n-butyl)-2-(2-morpholinophenyl)-3-methylguanidine which was converted into its monofumarate salt (m.p. 178°–179° C.).

EXAMPLE 294 TO 300

In a similar manner to that described in Example 2 the products of the Examples set out below were converted into their fumarate salts which were recrystallised from the solvent shown:

| Example | Starting Example | Recrystallisation Solvent | M.P. of fumarate Salt (°C.) |
|---------|------------------|---------------------------|------------------------------|
| 294 | 133 | 1:2 methanol:ether | 173–175 |
| 295 | 134 | 1:2 methanol:ether | 183–184 |
| 296 | 167 | 2:1 methanol:ether | 192–193 |
| 297 | 175 | 1:1 methanol:ether | 159–160 |
| 298 | 200 | propan-2-ol | 142–143 |
| 299 | 201 | 1:1 methanol:ether | 151–152 |
| 300 | 204 | 1:2 methanol:ether | 170–171 |

EXAMPLE 301

A mixture of 2-morpholinoaniline hydrochloride (19.2 g), m-cresol (80 ml) and dimethylcyanamide (9.45 g) was heated at 100° C. for five hours, cooled and added to a mixture of 40% aqueous sodium hydroxide solution (300 ml) and ice (300 g). Water (300 ml) was added and the resulting solid separated by filtration, washed with water and dissolved in dichloromethane. The solution was dried and the solvent removed to give a residue which was recrystallised from hexane to give 1,1-dimethyl-2-(2-morpholinophenyl)guanidine (m.p. 142°–143° C.).

EXAMPLE 303–304

Reaction of the products of Examples 175, 248 and 300 in the form of its free base respectively in methanol with L(+) tartaric acid gave the following compounds which were recrystallised from methanol.
- 301  4-{2-[1-(2-hydroxyethyl)-2-imidazolidinylideneamino]phenyl}morpholine monotartrate (m.p. 147°–148° C.).
- 303  1,1-dimethyl-2-(5-methyl-2-morpholinophenyl)guanidine monotartrate (m.p. 183°–184° C.).
- 304  1,1-dimethyl-2-(2-morpholinophenyl)guanidine monotartrate (m.p. 184°–185° C.).

EXAMPLES 305 and 306

Methanol and acetylchloride were reacted for 30 minutes to give hydrogen chloride which was reacted with the products of Example 248 and 301 respectively to give the products identified below. The products were recrystallised from the solvents given in parenthesis.
- 305  1,1-dimethyl-2-(5-methyl-2-morpholinophenyl)guanidine monohydrochloride (m.p. 161°–162° C.) (a 1:1 mixture of isopropanol and ether).
- 306  1,1-dimethyl-2-(2-morpholinophenyl)guanidine monohydrochloride (m.p. 200°–201° C.) (isopropanol).

EXAMPLE 307

Reaction of the product of Example 301 in acetone with concentrated sulphuric acid gave 1,1-dimethyl-2-(2-morpholinophenyl)guanidine hemisulphate (m.p. 234°–235° C.) which was recrystallised from a 1:1 mixture of methanol and ether.

EXAMPLE 308

Reaction of pamoic acid with the product of Example 301 in pyridine yielded 1,1-dimethyl-2-(2-morpholinophenyl)guanidine hemipamoate (m.p. 158°–160° C.).

EXAMPLE 309

A mixture of 1,3-dimethyl-2-imidazolidinone (4.6 g) in benzene (40 ml), 4-(2-aminobenzyl)morpholine (3.8 g) in benzene (20 ml) and phosphorus oxychloride (3.6 ml) was heated at 65°–70° C. for 20 hours to yield 4-[2-(1,3-dimethyl-2-imidazolidinylideneamino)benzyl]morpholine (m.p. 56°–58° C.) which was recrystallised from hexane.

EXAMPLE 310

A mixture of 1,3-dimethyl-2-imidazolidinone (10.95 g) in benzene (100 ml), 4-(2-amino-4-chlorobenzyl)morpholine (13.6 g) in benzene (50 ml) and phosphorus oxychloride (8.8 ml) was heated at 60°–65° C. for 8 hours to yield an oil which was purified by column chromatography on an alumina column using hexane, a 9:1 mixture of hexane and dichloromethane, a 1:1 mixture of hexane and dichloromethane and then dichloromethane as eluant. The resulting product (3.2 g) was dissolved in methanol (50 ml) and treated with fumaric acid (1.2 g) to yield 4-[4-chloro-2-(1,3-dimethyl-2-imidazolidinylideneamino)benzyl]morpholine monofumarate (m.p. 169°-170° C.) which was recrystallised from a 1:1 mixture of methanol and ether.

EXAMPLE 311

A mixture of 4-(2-aminobenzyl)morpholine dihydrochloride (10.6 g) and N,N-dimethylcyanamide (4.2 g) in m-cresol (40 ml) was heated at 90°-95° C. for 13 hours to yield a solid (m.p. 120°-121° C.) a portion of which (2 g) was dissolved in methanol (15 ml). Treatment with fumaric acid (0.9 g) gave N,N-dimethyl-N'-[2-morpholinomethylphenyl)guanidine monofumarate (m.p. 164°-165° C.) which was recrystallised from propan-2-ol.

EXAMPLE 312

A mixture of 4-(2-aminobenzyl)morpholine dihydrochloride (6.8 g), 4-cyanomorpholine (4.3 g) and m-cresol was heated at 90°-95° C. for 12 hours to yield N-(2-morpholinomethylphenyl)morpholine-4-carboxamidine (m.p. 118°-119° C.) which was recrystallised from hexane and then converted into its difumarate salt (m.p. 166°-167° C.) which was recrystallised from propan-2-ol.

EXAMPLE 313

The use of the compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

|  | Parts by weight |
|---|---|
| Active compound prepared as in Example 1 | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

I claim:

1. A compound of formula I

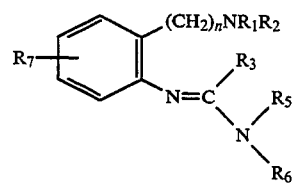

or a pharmaceutically acceptable salt thereof
in which n=0 or 1;
in which $R_1$ and $R_2$ together with the nitrogen atom to which they are attached form an optionally substituted heterocyclic ring of formula II

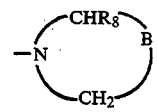

in which $R_8$ represents H or an alkyl group containing 1 to 3 carbon atoms and B represents a group selected from —(CH$_2$)$_2$—, —CHMeCH$_2$—, o-phenylene, —(CH$_2$)$_3$—, —CH$_2$CHMeCH$_2$—, —(CH$_2$)$_4$—, —CH$_2$OCH$_2$—, —CHMeOCHMe—, —CH$_2$SCH$_2$—, —CH$_2$S(O)CH$_2$—, —CH$_2$NMeCH$_2$— or —CH=CHCH$_2$—;
$R_3$ is a straight or branched alkyl group containing 1 to 7 carbon atoms or a cycloalkyl group containing 3 to 7 carbon atoms or a group of formula III

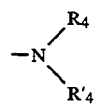

in which $R_4$ and $R'_4$, which are the same or different, are H or an alkyl group containing 1 to 4 carbon atoms;
$R_5$ and $R_6$ together with the nitrogen atom to which they are attached form a heterocyclic ring of formula VI

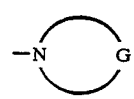

in which G represents a group selected from —(CH$_2$)$_4$—,   —(CH$_2$)$_5$—,   —(CH$_2$)$_2$O(CH$_2$)$_2$—, —(CH$_2$)$_2$S(CH$_2$)$_2$—, —(CH$_2$)$_2$NMe(CH$_2$)$_2$—, —(CH$_2$)$_2$CHMe(CH$_2$)$_2$— or —CH$_2$CHMeOCH-MeCH$_2$—; and R$_7$ represents H or one or more optional substituents selected from halo, alkyl groups containing 1 to 4 carbon atoms optionally substituted by methylthio, alkoxy groups containing 1 to 3 carbon atoms, alkylthio groups containing 1 to 3 carbon atoms, alkylsulphinyl groups containing 1 to 3 carbon atoms, alkylsulphonyl groups containing 1 to 3 carbon atoms, alkoxycarbonyl groups containing a total of 2 or 3 carbon atoms, trifluoromethyl or cyano.

2. A compound of formula I as claimed in claim 1 in which n=0, the group NR$_1$R$_2$ is a heterocyclic ring represented by formula II, R$_8$ represents H or methyl and B represents a group selected from —(CH$_2$)$_2$—, —CHMeCH$_2$—, —phenylene, —(CH$_2$)$_3$—, —CH$_2$CH-MeCH$_2$—, —(CH$_2$)$_4$—, —CH$_2$OCH$_2$—, —CH-MeOCHMe—, —CH$_2$SCH$_2$—, —CH$_2$S(O)CH$_2$—, —CH$_2$NMeCH$_2$— or —CH=CHCH$_2$—.

3. A compound of formula I as claimed in claim 2 in which the group NR$_1$R$_2$ is 1-pyrrolidinyl, 2-methyl-1-pyrrolidinyl, piperidino, 4-methylpiperidino, 1-hexahydroazepinyl, morpholino, 2,6-dimethylmorpholino, thiamorpholino, thiamorpholino-1-oxide, 2-isoindolinyl, 4-methyl-1-piperazinyl or 1-(1,2,5,6-tetrahydro)-pyridyl.

4. A compound of formula I as claimed in claim 1 in which n=1 and the group NR$_1$R$_2$ is morpholino or thiamorpholino.

5. A compound of formula I as claimed in claim 1 in which R$_3$ is methyl, ethyl, propyl, isopropyl, butyl, t-butyl, pentyl, cyclohexyl, amino, methylamino, dimethylamino or ethylamino.

6. A compound of formula I as claimed in claim 1 in which the group NR$_5$R$_6$ is 1-pyrrolidinyl, piperidino, 4-methylpiperidino, morpholino, 2,6-dimethylmorpholino, thiamorpholino or 4-methyl-1-piperazinyl.

7. A compound of formula I as claimed in claim 1 in which the group —N=C(R$_3$)NR$_5$R$_6$ is:
N,N—(3-oxapentamethylene)guanidino,
1,1-dimethyl-3,3-(3-oxapentamethylene)guanidino,
N,N-(2,4-dimethyl-3-oxapentamethylene)guanidino,
N,N-(3-thiapentamethylene)guanidino,
N,N-(3-methylpentamethylene)guanidino,
N,N-(N-methyl-3-azapentamethylene)guanidino,
N-methyl-N',N'-tetramethyleneguanidine,
N,N-pentamethyleneguanidino, or
1,1-dimethyl-3,3-pentamethyleneguanidino.

8. A compound of formula I as claimed in claim 1 in which R$_7$ represents H or one or more substituents selected from fluoro, chloro, methyl, ethyl, isobutyl, methylthio-methyl, methoxy, dimethoxy, methoxycarbonyl, methylthio, methylsulphinyl, methylsulphonyl, trifluoromethyl or cyano.

9. A compound of formula I as claimed in claim 1 in which n=0, —NR$_1$R$_2$ is morpholino, thiamorpholino, piperidino or 1-pyrrolidinyl, R$_3$ is —NH$_2$, R$_5$ and R$_6$ together with the nitrogen atom to which they are attached form a heterocyclic ring of formula VI and R$_7$ is H, fluoro, chloro, methyl, ethyl, methylthio-methyl or methylthio.

10. A compound of formula I as claimed in claim 9 in which the group —NR$_5$R$_6$ is morpholino or thiamorpholino and R$_7$ is H, fluoro, chloro, methyl, ethyl, methylthiomethyl or methylthio.

11. A compound of formula I as claimed in claim 1 selected from:
N-(2-morpholinophenyl)morpholine-4-carboxamidine,
N-(2-morpholinophenyl)thiamorpholine-4-carboxamidine and pharmaceutically acceptable salts thereof.

12. A pharmaceutical composition comprising a therapeutically effective amount of a compound of formula I

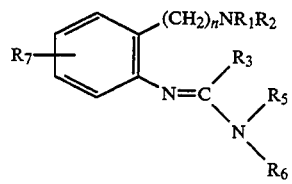

or a pharmaceutically acceptable salt thereof
in which n=0 or 1;
in which R$_1$ and R$_2$ together with the nitrogen atom to which they are attached form an optionally substituted heterocyclic ring of formula II

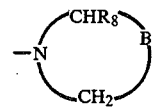

in which R$_8$ represents H or an alkyl group containing 1 to 3 carbon atoms and B represents a group selected from —(CH$_2$)$_2$—, —CHMeCH$_2$—, o-phenylene, —(CH$_2$)$_3$—, —CH$_2$CHMeCH$_2$—, —(CH$_2$)$_4$—, —CH$_2$OCH$_2$—, —CHMeOCHMe—, —CH$_2$SCH$_2$—, —CH$_2$S(O)CH$_2$—, —CH$_2$NMeCH$_2$— or —CH=CHCH$_2$—;

R$_3$ is a straight or branched alkyl group containing 1 to 7 carbon atoms or a cycloalkyl group containing 3 to 7 carbon atoms or a group of formula III

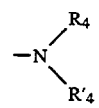

in which R$_4$ and R'$_4$, which are the same or different, are H or an alkyl group containing 1 to 4 carbon atoms;

R$_5$ and R$_6$ together with the nitrogen atom to which they are attached form a heterocyclic ring of formula VI

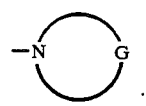

in which G represents a group selected from —(CH$_2$)$_4$—, —(CH$_2$)$_5$—, —(CH$_2$)$_2$O(CH$_2$)$_2$—, —(CH$_2$)$_2$S(CH$_2$)$_2$—, —(CH$_2$)$_2$NMe(CH$_2$)$_2$—, —(CH$_2$)$_2$CHMe(CH$_2$)$_2$— or —CH$_2$CHMeOCH-MeCH$_2$—; and R$_7$ represents H or one or more optional substituents selected from halo, alkyl groups containing 1 to 4 carbon atoms optionally substituted by methylthio, alkoxy groups containing 1 to 3 carbon atoms, alkylthio groups containing 1 to 3 carbon atoms, alkylsulphinyl groups containing 1 to 3 carbon atoms, alkylsulphonyl groups containing 1 to 3 carbon atoms, alkoxycarbonyl groups containing a total of 2 or 3 carbon atoms, trifluoromethyl or cyano.

13. A pharmaceutical composition as claimed in claim 12 in which n=0, the group $NR_1R_2$ is a heterocyclic ring represented by formula II, $R_8$ represents H or methyl and B represents a group selected from —(CH$_2$)$_2$—, —CHMeCH$_2$—, o-phenylene, —(CH$_2$)$_3$—, —CH$_2$CHMeCH$_2$—, —(CH$_2$)$_4$—, —CH$_2$OCH$_2$—, —CHMeOCHMe—, —CH$_2$SCH$_2$—, —CH$_2$S(O)CH$_2$—, —CH$_2$NMeCH$_2$— or —CH=CHCH$_2$—.

14. A pharmaceutical composition as claimed in claim 13 in which the group $NR_1R_2$ is 1-pyrrolidinyl, 2-methyl-1-pyrrolidinyl, piperidino, 4-methyl-piperidino, 1-hexahydroazepinyl, morpholino, 2,6-dimethylmorpholino, thiamorpholino, thiamorpholino-1-oxide, 2-isoindolinyl, 4-methyl-1-piperazinyl or 1-(1,2,5,6-tetrahydro)pyridyl.

15. A pharmaceutical composition as claimed in claim 12 in which n=1 and the group $NR_1R_2$ is morpholino or thiamorpholino.

16. A pharmaceutical composition as claimed in claim 12 in which $R_3$ is methyl, ethyl, propyl, isopropyl, butyl, t-butyl, pentyl, cyclohexyl, amino, methylamino, dimethylamino or ethylamino.

17. A pharmaceutical composition as claimed in claim 12 in which the group $NR_5R_6$ is 1-pyrrolidinyl, piperidino, 4-methylpiperidino, morpholino, 2,6-dimethylmorpholino, thiamorpholino or 4-methyl-1-piperazinyl.

18. A pharmaceutical composition as claimed in claim 12 in which the group $-N=C(R_3)NR_5R_6$ is:
N,N-(3-oxapentamethylene)guanidino,
1,1-dimethyl-3,3-(3-oxapentamethylene)guanidino,
N,N-(2,4-dimethyl-3-oxapentamethylene)guanidino,
N,N-(3-thiapentamethylene)guanidino,
N,N-(3-methylpentamethylene)guanidino,
N,N-(N-methyl-3-azapentamethylene)guanidino,
N-methyl-N',N'-tetramethyleneguanidine,
N,N-pentamethyleneguanidino, or
1,1-dimethyl-3,3-pentamethyleneguanidino.

19. A pharmaceutical composition as claimed in claim 12 in which $R_7$ represents H or one or more substituents selected from fluoro, chloro, methyl, ethyl, isobutyl, methylthiomethyl, methoxy, dimethoxy, methoxycarbonyl, methylthio, methylsulphinyl, methylsulphonyl, tri-fluoromethyl or cyano.

20. A pharmaceutical composition as claimed in claim 12 in which n=0, —$NR_1R_2$ is morpholino, thiamorpholino, piperidino or 1-pyrrolidinyl, $R_3$ is —$NH_2$, $R_5$ and $R_6$ together with the nitrogen atom to which they are attached form a heterocyclic ring of formula VI and $R_7$ is H, fluoro, chloro, methyl, ethyl, methylthiomethyl or methylthio.

21. A pharmaceutical composition as claimed in claim 20 in which the group —$NR_5R_6$ is morpholino or thiamorpholino and $R_7$ is H, fluoro, chloro, methyl, ethyl, methylthiomethyl or methylthio.

22. A pharmaceutical composition as claimed in claim 12 wherein the compound of formula I is selected from:
N-(2-morpholinophenyl)morpholine-4-carboxamidine, N-(2-morpholinophenyl)thiamorpholine-4-carboxamidine and pharmaceutically acceptable salts thereof.

23. A method of treating hyperglycemia comprising administering to a subject in need thereof, a therapeutically effective amount of a compound of formula I

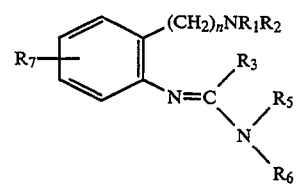

or a pharmaceutically acceptable salt thereof
in which n=0 or 1;
in which $R_1$ and $R_2$ together with the nitrogen atom to which they are attached form an optionally substituted heterocyclic ring of formula II

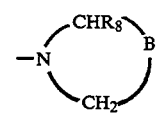

in which $R_8$ represents H or an alkyl group containing 1 to 3 carbon atoms and B represents a group selected from —(CH$_2$)$_2$—, —CHMeCH$_2$—, o-phenylene, —(CH$_2$)$_3$—, —CH$_2$CHMeCH$_2$—, —(CH$_2$)$_4$—, —CH$_2$OCH$_2$—, —CHMeOCHMe—, —CH$_2$SCH$_2$—, —CH$_2$S(O)CH$_2$—, —CH$_2$NMeCH$_2$— or —CH=CHCH$_2$—;

$R_3$ is a straight or branched alkyl group containing 1 to 7 carbon atoms or a cycloalkyl group containing 3 to 7 carbon atoms or a group of formula III

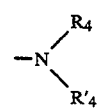

in which $R_4$ and $R'_4$, which are the same or different, are H or an alkyl group containing 1 to 4 carbon atoms;

$R_5$ and $R_6$ together with the nitrogen atom to which they are attached form a heterocyclic ring of formula VI

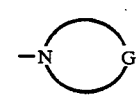

in which G represents a group selected from —(CH$_2$)$_4$—, —(CH$_2$)$_5$—, —(CH$_2$)$_2$O(CH$_2$)$_2$—, —(CH$_2$)$_2$S(CH$_2$)$_2$—, —(CH$_2$)$_2$NMe(CH$_2$)$_2$—, —(CH$_2$)$_2$CHMe(CH$_2$)$_2$— or —CH$_2$CHMeOCHMeCH$_2$—; and $R_7$ represents H or one or more optional substituents selected from halo, alkyl groups containing 1 to 4 carbon atoms optionally substituted by methylthio, alkoxy groups containing 1 to 3 carbon atoms, alkylthio groups containing 1 to 3 carbon atoms, alkylsulphinyl groups containing 1 to 3 carbon atoms, alkylsulphonyl groups containing 1 to 3 carbon atoms, alkoxycarbonyl groups containing a total of 2 or 3 carbon atoms, trifluoromethyl or cyano.

24. A method as claimed in claim 23 in which n=0, the group $NR_1R_2$ is a heterocyclic ring represented by formula II, $R_8$ represents H or methyl and B represents a group selected from $-(CH_2)_2-$, $-CHMeCH_2-$, o—phenylene, $-(CH_2)_3-$, $-CH_2CHMeCH_2-$, $-(CH_2)_4-$, $-CH_2OCH_2-$, $-CHMeOCHMe-$, $-CH_2SCH_2-$, $-CH_2S(O)CH_2-$, $-CH_2NMeCH_2-$ or $-CH=CHCH_2-$.

25. A method as claimed in claim 24 in which the group $NR_1R_2$ is 1-pyrrolidinyl, 2-methyl-1-pyrrolidinyl, piperidino, 4-methyl-piperidino, 1-hexa-hydroazepinyl, morpholino, 2,6-dimethylmorpholino, thiamorpholino, thiamorpholino-1-oxide, 2-isoindolinyl, 4-methyl-1-piperazinyl or 1-(1,2,5,6-tetrahydro)-pyridyl.

26. A method as claimed in claim 23 in which n=1 and the group $NR_1R_2$ is morpholino or thiamorpholino.

27. A method as claimed in claim 23 in which $R_3$ is methyl, ethyl, propyl, isopropyl, butyl, -butyl, pentyl, cyclohexyl, amino, methylamino, dimethylamino or ethylamino.

28. A method as claimed in claim 23 in which the group $NR_5R_6$ is 1-pyrrolidinyl, piperidino, 4-methyl-piperidino, morpholino, 2,6-dimethylmorpholino, thiamorpholino or 4-methyl-1-piperazinyl.

29. A method as claimed in claim 23 in which the group $-N=C(R_3)NR_5R_6$ is:
N,N-(3-oxapentamethylene)guanidino,
1,1-dimethyl-3,3-(3-oxapentamethylene)guanidino,
N,N-(2,4-dimethyl-3-oxapentamethylene)guanidino,
N,N-(3-thiapentamethylene)guanidino,
N,N-(3-methylpentamethylene)guanidino,
N,N-(N-methyl-3-azapentamethylene)guanidino,
N-methyl-N',N'-tetramethyleneguanidine,
N,N-pentamethyleneguanidino, or
1,1-dimethyl-3,3-pentamethyleneguanidino.

30. A method as claimed in claim 23 in which $R_7$ represents H or one or more substituents selected from fluoro, chloro, methyl, ethyl, isobutyl, methylthiomethyl, methoxy, dimethoxy, methoxycarbonyl, methylthio, methylsulphinyl, methylsulphonyl, trifluoromethyl or cyano.

31. A method as claimed in claim 23 in which n=0, $-NR_1R_2$ is morpholino, thiamorpholino, piperidino or 1-pyrrolidinyl, $R_3$ is $-NH_2$, $R_5$ and $R_6$ together with the nitrogen atom to which they are attached form a heterocyclic ring of formula VI and $R_7$ is H, fluoro, chloro, methyl, ethyl, methylthiomethyl or methylthio.

32. A method as claimed in claim 31 in which the group $-NR_5R_6$ is morpholino or thiamorpholino and $R_7$ is H, fluoro, chloro, methyl, ethyl, methylthiomethyl or methylthio.

33. A method as claimed in claim 23 in which the compound of formula I is selected from:
N-(2-morpholinophenyl)morpholine-4-carboxamidine,
N-(2-morpholinophenyl)thiamorpholine-4-carboxamidine and pharmaceutically acceptable salts thereof.

* * * * *